United States Patent
Takamuro et al.

(10) Patent No.: US 8,314,247 B2
(45) Date of Patent: Nov. 20, 2012

(54) HYDRAZONE DERIVATIVE

(75) Inventors: Iwao Takamuro, Osaka (JP); Kazutoshi Sugawara, Tsuruoka (JP); Hiroshi Sugama, Osaka (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 321 days.

(21) Appl. No.: 12/522,663

(22) PCT Filed: Jan. 9, 2008

(86) PCT No.: PCT/JP2008/050466
§ 371 (c)(1),
(2), (4) Date: Jul. 9, 2009

(87) PCT Pub. No.: WO2008/084872
PCT Pub. Date: Jul. 17, 2008

(65) Prior Publication Data
US 2010/0099662 A1   Apr. 22, 2010

(30) Foreign Application Priority Data

Jan. 10, 2007  (JP) ................ 2007-002159

(51) Int. Cl.
*A61K 31/427* (2006.01)
*C07D 417/12* (2006.01)
*C07D 417/14* (2006.01)

(52) U.S. Cl. ........ 548/128; 540/544; 540/575; 540/603; 544/58.2; 544/60; 544/133; 544/329; 544/367; 546/114; 546/279.1; 548/139; 548/181; 548/195; 514/211.03; 514/211.08; 514/211.15; 514/217.03; 514/217.11; 514/218; 514/227.8; 514/233.8; 514/236.8; 514/254.02; 514/255.05; 514/275; 514/301; 514/326; 514/342; 514/361; 514/363; 514/371

(58) Field of Classification Search .......... None
See application file for complete search history.

(56) References Cited

U.S. PATENT DOCUMENTS

| | | | |
|---|---|---|---|
| 4,207,234 A | 6/1980 | Kamiya et al. | |
| 4,231,927 A | 11/1980 | Monguzzi et al. | |
| 4,386,089 A * | 5/1983 | Konig et al. | 514/192 |
| 4,576,753 A * | 3/1986 | Kamiya et al. | 540/364 |
| 4,647,658 A | 3/1987 | Hamashima et al. | |
| 6,218,418 B1 | 4/2001 | Pevarello et al. | |
| 6,369,232 B1 | 4/2002 | Sidduri | |
| 7,034,049 B1 | 4/2006 | Pevarello et al. | |
| 7,037,929 B1 | 5/2006 | Pevarello et al. | |
| 7,132,425 B2 | 11/2006 | Chen et al. | |
| 7,153,815 B2 * | 12/2006 | Kawata et al. | 504/344 |
| 7,432,287 B2 | 10/2008 | Iino et al. | |
| 7,514,439 B2 * | 4/2009 | Sugawara et al. | 514/254.02 |
| 7,576,108 B2 | 8/2009 | Weichert et al. | |
| 2003/0138416 A1 | 7/2003 | Lau | |
| 2003/0171411 A1 | 9/2003 | Kodra et al. | |
| 2003/0225283 A1 | 12/2003 | Corbett et al. | |
| 2004/0147748 A1 | 7/2004 | Chen et al. | |
| 2004/0181067 A1 | 9/2004 | Fyfe et al. | |
| 2005/0107399 A1 | 5/2005 | Boman et al. | |
| 2005/0282851 A1 | 12/2005 | Bebernitz | |
| 2006/0111353 A1 | 5/2006 | Weichert et al. | |
| 2006/0167053 A1 | 7/2006 | Iino et al. | |
| 2006/0178429 A1 | 8/2006 | Corbett et al. | |
| 2006/0258701 A1 | 11/2006 | Mitsuya et al. | |
| 2007/0078168 A1 | 4/2007 | Caulkett | |
| 2009/0018056 A1 | 1/2009 | Iino et al. | |

FOREIGN PATENT DOCUMENTS

| | | |
|---|---|---|
| CA | 1 135 687 A | 11/1982 |
| CA | 1 161 429 A | 1/1984 |
| DE | 3021373 A1 | 12/1981 |
| DE | 3520514 A1 | 12/1985 |
| EP | 0 004 956 A1 | 10/1979 |
| EP | 1 229 026 A1 | 8/2002 |
| GB | 2 102 423 A | 2/1983 |
| JP | 2001-199971 A | 7/2001 |
| WO | WO-00/26202 A1 | 5/2000 |
| WO | WO-01/12189 A1 | 2/2001 |
| WO | WO 01/55144 * | 8/2001 |
| WO | WO-03-055482 A1 | 7/2003 |
| WO | WO-03/095438 A1 | 11/2003 |
| WO | WO-2004/050645 A1 | 6/2004 |
| WO | WO-2004/052869 A1 | 6/2004 |
| WO | WO-2004/058724 A1 | 7/2004 |

(Continued)

OTHER PUBLICATIONS

Pilkington et al., Chemical Abstracts, 135:152792, 2001.*
Extended European Search Report dated May 13, 2011 for Application No. 08703326.2.

*Primary Examiner* — Laura L. Stockton
(74) *Attorney, Agent, or Firm* — Birch, Stewart, Kolasch & Birch, LLP

(57) ABSTRACT

A hydrazone derivative of formula [I]:

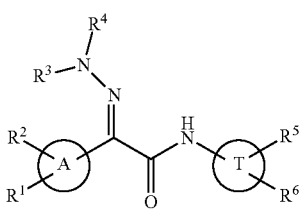

wherein Ring A is aryl or heteroaryl, Ring T is heteroaryl or heterocycle, $R^1$ and $R^2$ are independently hydrogen atom, halogen atom, cycloalkylsulfonyl, etc., $R^3$ and $R^4$ combine each other together with the adjacent nitrogen atom to form substituted or unsubstituted heterocycle, $R^5$ is hydrogen atom, halogen atom, cyano, nitro, tetrazolyl, etc., and $R^6$ is hydrogen atom, etc.;
or a pharmaceutically acceptable salt thereof is useful as a glucokinase activation agent.

31 Claims, No Drawings

FOREIGN PATENT DOCUMENTS

| WO | WO-2004/063179 A1 | 7/2004 |
| WO | WO-2004/063194 A1 | 7/2004 |
| WO | WO-2004/072066 A1 | 8/2004 |
| WO | WO-2004/076420 A1 | 9/2004 |
| WO | WO-2004/081001 A1 | 9/2004 |
| WO | WO-2005/023761 A2 | 3/2005 |
| WO | WO-2005/044801 A1 | 5/2005 |
| WO | WO-2007/007886 A1 | 1/2007 |

* cited by examiner

HYDRAZONE DERIVATIVE

CROSS-REFERENCE TO RELATED APPLICATIONS

The present application is a national phase under 35 U.S.C. §371 of PCT International Application No. PCT/JP2008/050466 which has an International filing date of Jan. 9, 2008, which claims priority to Application No. 2007-002159 filed in Japan on Jan. 10, 2007 under 35 U.S.C. §119.

TECHNICAL FIELD

The present invention relates to a novel hydrazone derivative having an excellent glucokinase activation effect, which is useful as a medicine.

BACKGROUND ART

Glucokinase (GK) is one of four hexokinases found in mammalian animals. Hexokinases catalyze a conversion of glucose into glucose-6-phosphate which is the first step of glucose metabolism. GK is localized mainly in hepatic parenchymal cells and pancreatic β cells, and plays an important role in whole body glucose homeostasis as a rate-controlling enzyme for glucose metabolism in these cells. The hepatic parenchymal and pancreatic forms of the enzyme are different in N-terminal 15 amino-acid sequence depending on the difference of each splicing, but are functionally indistinguishable. Three hexokinases except GK are saturated in enzymatic activity at a glucose concentration below 1 mM, but Km of GK is 8 mM, which is within a physiological range of blood-glucose levels. Therefore, GK-mediated intracellular glucose metabolism is activated as the concentration of blood glucose increases from normal level (5 mM) to postprandial level (10 to 15 mM). A hypothesis that GK functions as a glucose sensor of pancreatic β cells and hepatocyte has been proposed (Nonpatent Document 1). Thereafter, it has been clarified that GK actually plays a definitely important role in whole body glucose homeostasis according to the results of GK genetically-modified animal studies. GK KO mice die soon after birth (Nonpatent Document 2), while both normal and diabetic mice overexpressing GK showed lower glucose level than wild type animals (Nonpatent Document 3).

In maturity-onset diabetes of the young type II (MODY-2), which is one of the genetically determined diabetes, loss of function mutations in GK has been found and it is thought that the low GK activity in MODY-2 results in hyperglycemia (Nonpatent Document 4). On the other hand, families having a GK mutation with increased enzymatic activity have been found and these people have shown hypoglycemia (Nonpatent Document 5). Accordingly, GK is believed to be a glucose sensor and to play an important role in maintenance of glucose homeostasis in human as well. It is expected that a GK activating compound has an insulinotropic action in β cells, an enhancing effect of glucose uptake in liver and an inhibitory effect of hepatic output since such a compound activates a GK sensor system, and hence, it is believed that such a compound is useful for treating, for example, Type 2 diabetes.

Recently, it has been shown that a pancreatic β cell type glucokinase is distributed locally in feeding center (Ventromedial hypothalamus, VMH) in rat brain. About 20% of nerve cells in VMH are referred to as glucose responsive neurons and it has been thought from the past that they play important roles in controlling of body weights. An intracerebral administration of glucose in rat decreases food intake, but on the contrary, rat becomes overeating by an intracerebral administration of a glucose analog glucosamine, which cause a suppression of glucose metabolism. In electrophysiological experiments, glucose responsive neurons in VMH are stimulated when glucose increases from 5 to 20 mM, and their activities are blocked by glucosamine or the like (Nonpatent Document 6). It is thought that a glucose sensor mechanism of VHM is similar to that of pancreatic β cells. Therefore, a GK activating substance has a possibility of ameliorating obesity which is one of the major problems in Type 2 diabetes as well as correcting hyperglycemia.

Accordingly, a compound having a GK activation effect is useful as a therapeutic and/or preventive agent for diabetes, or chronic complication of diabetes such as retinopathy, nephropathy, neuropathy, ischemic heart disease or arteriosclerosis, or even obesity.

The compound having a GK activation effect includes, for example, pyridinecarboxylic acid derivatives (Patent Document 1), 2-pyridine-carboxamide derivatives (Patent Document 2), heteroarylcarbamoyl-benzene derivatives (Patent Document 3), heteroaryl derivatives (Patent Document 4), substituted arylcyclopropylacetamide derivatives (Patent Document 5), 5-substituted pyrazine or pyridine derivatives (Patent Document 6), substituted (thiazol-2-yl)amide or sulfonamide derivatives (Patent Document 7), substituted phenylacetamide derivatives (Patent Document 8) or amide derivatives (Patent Document 9).

[Patent Document 1] WO05/044801
[Patent Document 2] WO04/081001
[Patent Document 3] WO04/076420
[Patent Document 4] WO04/063194
[Patent Document 5] WO04/063179
[Patent Document 6] WO04/052869
[Patent Document 7] WO04/050645
[Patent Document 8] WO03/095438
[Patent Document 9] WO03/055482
[Nonpatent Document 1] American Journal Physiology, 247 (3Pt2), 1984, p. 527-536
[Nonpatent Document 2] Cell, 83, 1995, p. 69-78
[Nonpatent Document 3] Proceedings of the National Academy of Sciences of the U.S.A., 93, 1996, p. 7225-7230
[Nonpatent Document 4] Nature Genetics, 356, 1992, p. 721-722
[Nonpatent Document 5] New England Journal of Medicine, 338, 1998, p. 226-230
[Nonpatent Document 6] Diabetes, 48(9), 1999, p. 1763-72

DISCLOSURE OF INVENTION

The present invention provides a novel compound having an excellent glucokinase activation effect, which is useful for an active ingredient of a medicine for the prophylaxis and/or treatment of diseases involving glucokinase, such as diabetes, complication associated with diabetes, or obesity. According to extensive studies for problems to be solved by the present invention, it has been found that a hydrazone derivative of the following formula has an excellent glucokinase activation effect, and the present invention has been completed.

The present invention includes the following embodiments.

(1) A hydrazone derivative of the general formula [I]:

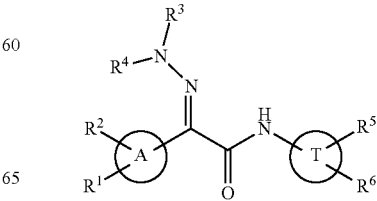

wherein Ring A is aryl or heteroaryl;
Ring T is heteroaryl or heterocycle;
$R^1$ is hydrogen atom, halogen atom, cycloalkylsulfonyl, alkylsulfonyl, alkylsulfinyl, alkylthio, substituted or unsubstituted tetrazolyl, —$COR^{10}$ or —$CR^{12}(OH)R^{10}$;
$R^2$ is hydrogen atom, halogen atom, cycloalkylsulfonyl, substituted or unsubstituted alkylsulfonyl, substituted or unsubstituted alkylthio, nitro, substituted or unsubstituted amino, substituted or unsubstituted aminosulfonyl, substituted or unsubstituted heterocyclyl-thio, substituted or unsubstituted heterocyclyl-sulfinyl, substituted or unsubstituted heterocyclyl-sulfonyl, substituted or unsubstituted heteroarylsulfonyl, alkenyloxy, substituted or unsubstituted alkoxy, substituted or unsubstituted alkylsulfinyl, substituted or unsubstituted heteroaryl, substituted or unsubstituted heteroarylthio, —$COR^{11}$ or —$CR^{13}(OH)R^{11}$;
$R^{10}$ is alkyl, cycloalkyl, heteroaryl or heterocycle;
$R^{11}$ is substituted or unsubstituted alkyl, substituted or unsubstituted cycloalkyl, substituted or unsubstituted heteroaryl or heterocycle;
$R^{12}$ is hydrogen atom or alkyl;
$R^{13}$ is hydrogen atom or alkyl;
$R^3$ and $R^4$ are independently hydrogen atom, substituted or unsubstituted alkyl or substituted or unsubstituted heteroaryl; or $R^3$ and $R^4$ combine each other together with the adjacent nitrogen atom to form substituted or unsubstituted heterocycle;
$R^5$ is hydrogen atom, formyl, halogen atom, oxo, substituted or unsubstituted alkoxy, substituted or unsubstituted aminosulfonyl, substituted or unsubstituted alkylthio, cyano, substituted or unsubstituted heterocyclyl-sulfonyl, nitro, substituted or unsubstituted cycloalkyl, alkoxycarbonyl, alkenyl, alkylsulfonyl, substituted or unsubstituted carbamoyl, substituted or unsubstituted heteroarylthio, substituted or unsubstituted amino, carboxy, substituted or unsubstituted heteroaryl, substituted or unsubstituted alkynyl, substituted or unsubstituted heterocyclyl-carbonyl, substituted or unsubstituted heterocyclyl-oxy, substituted or unsubstituted heterocycle, substituted or unsubstituted heterocyclyl-thio, substituted or unsubstituted cycloalkyloxy, alkanoyl, or substituted or unsubstituted alkyl;
$R^6$ is hydrogen atom, substituted or unsubstituted alkyl, halogen atom, or carboxy;
or a pharmaceutically acceptable salt thereof.
(2) The hydrazone derivative of (1), wherein Ring T is heteroaryl or heterocycle of

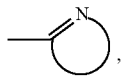

or a pharmaceutically acceptable salt thereof.
(3) The hydrazone derivative of either one of (1) or (2), wherein Ring T is thiazolyl, thiazolopyridinyl, pyridyl, pyrazinyl, benzothiazolyl, quinolyl, thiadiazolyl, pyrazolyl, thiazolopyrazinyl, thiazolopyrimidinyl, cyclohexanothiazolyl or dihydropyrazolopyridinyl, or a pharmaceutically acceptable salt thereof.
(4) The hydrazone derivative of either one of (1) or (2), wherein Ring T is thiazolyl, thiazolopyridinyl, pyridyl, pyrazinyl, benzothiazolyl, thiadiazolyl, thiazolopyrazinyl, thiazolopyrimidinyl, cyclohexanothiazolyl or dihydropyrazolopyridinyl, or a pharmaceutically acceptable salt thereof.
(5) The hydrazone derivative of either one of (1) or (2), wherein Ring T is thiazolyl, thiazolopyridinyl, pyrazinyl, thiadiazolyl, thiazolopyrazinyl or thiazolopyrimidinyl, or a pharmaceutically acceptable salt thereof.
(6) The hydrazone derivative of either one of (1) or (2), wherein Ring T is thiazolyl or thiazolopyridinyl, or a pharmaceutically acceptable salt thereof.
(7) The hydrazone derivative of any one of (1) to (6), wherein Ring A is aryl, or a pharmaceutically acceptable salt thereof.
(8) The hydrazone derivative of any one of (1) to (6), wherein Ring A is phenyl or pyridyl, or a pharmaceutically acceptable salt thereof.
(9) The hydrazone derivative of any one of (1) to (8), wherein $R^1$ is hydrogen atom or halogen atom, or a pharmaceutically acceptable salt thereof.
(10) The hydrazone derivative of any one of (1) to (8), wherein $R^1$ is hydrogen atom, or a pharmaceutically acceptable salt thereof.
(11) The hydrazone derivative of any one of (1) to (10), wherein $R^2$ is cycloalkylsulfonyl, substituted or unsubstituted alkylsulfonyl, substituted or unsubstituted alkylthio, nitro, substituted or unsubstituted amino, substituted or unsubstituted aminosulfonyl, substituted or unsubstituted heterocyclyl-thio, substituted or unsubstituted heterocyclyl-sulfonyl, substituted or unsubstituted heteroarylsulfonyl, substituted or unsubstituted alkylsulfinyl, substituted or unsubstituted heteroaryl, or substituted or unsubstituted heteroarylthio, or a pharmaceutically acceptable salt thereof.
(12) The hydrazone derivative of any one of (1) to (10), wherein $R^2$ is cycloalkylsulfonyl, substituted or unsubstituted alkylsulfonyl, substituted or unsubstituted aminosulfonyl, or substituted or unsubstituted heterocyclyl-sulfonyl, or a pharmaceutically acceptable salt thereof.
(13) The hydrazone derivative of any one of (1) to (10), wherein $R^2$ is cycloalkylsulfonyl, substituted or unsubstituted alkylsulfonyl, or substituted or unsubstituted aminosulfonyl, or a pharmaceutically acceptable salt thereof.
(14) The hydrazone derivative of any one of (1) to (10), wherein $R^2$ is cycloalkylsulfonyl, or substituted or unsubstituted alkylsulfonyl, or a pharmaceutically acceptable salt thereof.
(15) The hydrazone derivative of any one of (1) to (13), wherein the substituent of the "substituted aminosulfonyl" in $R^2$ is substituted or unsubstituted alkyl, cycloalkyl, alkoxy, or substituted or unsubstituted heterocycle, or a pharmaceutically acceptable salt thereof.
(16) The hydrazone derivative of any one of (1) to (14), wherein the substituent of the "substituted alkylsulfonyl" in $R^2$ is alkoxy, or a pharmaceutically acceptable salt thereof.
(17) The hydrazone derivative of any one of (1) to (16), wherein $R^3$ and $R^4$ combine each other together with the adjacent nitrogen atom to form substituted or unsubstituted heterocycle, or a pharmaceutically acceptable salt thereof.
(18) The hydrazone derivative of any one of (1) to (17), wherein the heterocycle in the "substituted or unsubstituted heterocycle which $R^3$ and $R^4$ combine each other together with the adjacent nitrogen atom to form" is pyrrolidine, piperidine, piperazine, morpholine, thiomorpholine, azetidine, homopiperazine, homomorpholine or homothiomorpholine, or a pharmaceutically acceptable salt thereof.
(19) The hydrazone derivative of any one of (1) to (18), wherein the substituent of substituted heterocycle in the "substituted or unsubstituted heterocycle which $R^3$ and $R^4$ combine each other together with the adjacent nitrogen atom to form" is alkyl, alkoxy, hydroxy or oxo, or a pharmaceutically acceptable salt thereof.
(20) The hydrazone derivative of any one of (1) to (19), wherein $R^5$ is hydrogen atom, formyl, halogen atom, oxo, substituted or unsubstituted alkoxy, substituted or unsubstituted aminosulfonyl, substituted or unsubstituted alkylthio, cyano, substituted or unsubstituted heterocyclyl-sulfonyl, nitro, substituted or unsubstituted cycloalkyl, alkoxycarbonyl, alkenyl, substituted or unsubstituted carbamoyl, substituted or unsubstituted heteroarylthio, substituted or unsubstituted amino, substituted or unsubstituted heteroaryl, substituted or unsubstituted alkynyl, substituted or unsubstituted heterocyclyl-oxy, alkanoyl, or substituted or unsubstituted alkyl, or a pharmaceutically acceptable salt thereof.

(21) The hydrazone derivative of any one of (1) to (19), wherein $R^5$ is hydrogen atom, halogen atom, substituted or unsubstituted alkoxy, substituted or unsubstituted alkylthio, cyano, substituted or unsubstituted cycloalkyl, substituted or unsubstituted carbamoyl, substituted or unsubstituted amino, substituted or unsubstituted heterocyclyl-oxy, alkanoyl, or substituted or unsubstituted alkyl, or a pharmaceutically acceptable salt thereof.

(22) The hydrazone derivative of any one of (1) to (19), wherein $R^5$ is halogen atom, substituted or unsubstituted alkoxy, substituted or unsubstituted alkylthio, substituted or unsubstituted amino, substituted or unsubstituted heterocyclyl-oxy, or substituted or unsubstituted alkyl, or a pharmaceutically acceptable salt thereof.

(23) The hydrazone derivative of any one of (1) to (19), wherein $R^5$ is substituted or unsubstituted alkoxy, substituted or unsubstituted amino, substituted or unsubstituted heterocyclyl-oxy, or substituted or unsubstituted alkyl, or a pharmaceutically acceptable salt thereof.

(24) The hydrazone derivative of any one of (1) to (19), wherein $R^5$ is substituted or unsubstituted alkyl, or a pharmaceutically acceptable salt thereof.

(25) The hydrazone derivative of any one of (1) to (24), wherein the substituent of the "substituted alkyl" in $R^5$ is substituted or unsubstituted heterocycle, substituted or unsubstituted amino, substituted or unsubstituted alkoxy, substituted or unsubstituted carbamoyl, hydroxy, trialkylsilyloxy, alkylthio, alkylsulfonyl, substituted or unsubstituted heterocyclyl-oxy, heteroaryl, substituted or unsubstituted hydroxyimino, halogen atom, carboxy, alkoxycarbonyl, or alkanoyloxy, or a pharmaceutically acceptable salt thereof.

(26) The hydrazone derivative of any one of (1) to (19), wherein $R^5$ is substituted or unsubstituted alkoxy, or a pharmaceutically acceptable salt thereof.

(27) The hydrazone derivative of any one of (1) to (19) and (26), wherein the substituent of the "substituted alkoxy" in $R^5$ is amino optionally substituted by 1 or 2 group(s) selected from alkyl or alkoxycarbonyl; alkoxycarbonyl; carbamoyl optionally substituted by mono- or di-alkyl; carboxyl; hydroxy; heterocycle optionally substituted by oxo; trialkylsilyloxy; or alkoxy; or a pharmaceutically acceptable salt thereof.

(28) The hydrazone derivative of any one of (1) to (27), wherein $R^6$ is hydrogen atom, or substituted or unsubstituted alkyl, or a pharmaceutically acceptable salt thereof.

(29) The hydrazone derivative of any one of (1) to (27), wherein $R^6$ is hydrogen atom, or a pharmaceutically acceptable salt thereof.

(30) A medicament comprising the hydrazone derivative of any one of (1) to (29), or a pharmaceutically acceptable salt thereof.

(31) The medicament of (30), which is a glucokinase activating agent.

(32) The medicament of (30), which is a therapeutic and/or preventive agent for diabetes.

(33) The medicament of (30), which is a therapeutic and/or preventive agent for chronic complication associated with diabetes including retinopathy, nephropathy, neuropathy, ischemic heart disease or arteriosclerosis.

(34) The medicament of (30), which is a therapeutic and/or preventive agent for obesity.

The following terms used herein mean as defined below.

The term "halogen atom" includes fluorine atom, chlorine atom, bromine atom or iodine atom, preferably fluorine atom or chlorine atom.

The term "alkyl", which includes "alkyl" moiety in a group bound with other groups such as "alkylthio", "hydroxyalkyl", etc. (the same for other groups defined hereinafter), includes, for example, straight- or branched-chain alkyl of $C_{1-6}$, preferably $C_{1-4}$, specifically methyl, ethyl, propyl, isopropyl, isobutyl, t-butyl, pentyl, hexyl or the like.

The term "alkenyl" includes, for example, straight- or branched-chain alkenyl of $C_{2-6}$, preferably $C_{2-4}$, specifically vinyl, propenyl, isopropenyl, butenyl, pentenyl, hexenyl or the like.

The term "alkynyl" includes, for example, straight- or branched-chain alkynyl of $C_{2-6}$, preferably $C_{2-4}$, specifically acetylenyl, propynyl, butynyl, pentynyl, hexynyl or the like.

The term "alkoxy" includes, for example, straight- or branched-chain alkoxy of $C_{1-6}$, preferably $C_{1-4}$, specifically methoxy, ethoxy, propoxy, isopropoxy, butoxy, t-butoxy, pentyloxy, hexyloxy or the like.

The term "alkanoyl" includes, for example, straight- or branched-chain alkanoyl of $C_{2-7}$, preferably $C_{2-5}$, specifically acetyl, propionyl, butyryl, pentanoyl or the like.

The term "cycloalkyl" includes, for example, cycloalkyl of $C_{3-8}$, preferably $C_{3-6}$, specifically cyclopropyl, cyclobutyl, cyclopentyl, cyclohexyl or cycloheptyl.

The term "aryl" includes 6 to 14-membered, preferably 6 to 10-membered mono-, bi- or tri-cyclic aromatic hydrocarbon, specifically phenyl, naphthyl, phenanthryl, anthryl or the like, particularly phenyl.

The term "heteroaryl" includes 4 to 10-membered, preferably 5 to 9-membered, mono- or bi-cyclic aromatic hydrocarbon wherein 1 to 3 carbon atom(s) is(are) substituted with heteroatoms independently selected from oxygen atom, sulfur atom and nitrogen atom, specifically thienyl, thiazolyl, pyrazolyl, imidazolyl, isoxazolyl, triazolyl, thiadiazolyl, pyridyl, pyrimidinyl, pyrazinyl, quinolyl, benzothiazolyl, thiazolopyridinyl, thiazolopyrazinyl, thiazolopyrimidinyl or the like.

The term "heterocycle" includes 4 to 10-membered, preferably 4 to 9-membered, mono- or bi-cyclic non-aromatic hydrocarbon wherein 1 to 3 carbon atom(s) is(are) substituted with heteroatoms independently selected from oxygen atom, sulfur atom and nitrogen atom, specifically oxetanyl, azetidinyl, pyrrolidinyl, tetrahydrofuryl, dioxolanyl, piperidinyl, piperazinyl, homopiperazinyl, tetrahydropyranyl, thiacyclohexyl, morpholinyl, thiomorpholinyl, cyclohexanothiazolyl, dihydrothiazolopyridinyl, tetrahydrothiazolopyridinyl or the like.

Alternatively, illustrative embodiments of "halogen atom", "alkyl", "alkenyl", "alkynyl", "alkoxy", "alkanoyl", "cycloalkyl", "aryl", "heteroaryl" and "heterocycle" include those specifically described in EXAMPLES.

Each group shown by each symbol of compound [I] is explained as below.

A preferable "aryl" in Ring A includes phenyl.

A preferable "heteroaryl" in Ring A includes thienyl or pyridyl, particularly pyridyl.

In case that Ring A is 6-membered ring, $R^2$ is preferably substituted on 4-position.

The term "heteroaryl" in Ring T includes, for example, 5 to 9-membered mono- or bi-cyclic heteroaryl optionally having 1 to 3 heteroatom(s) independently selected from oxygen atom, sulfur atom and nitrogen atom, specifically thiazolyl, pyrazolyl, thiadiazolyl, pyridyl, pyrazinyl, benzothiazolyl, thiazolopyridinyl, thiazolopyrazinyl, thiazolopyrimidinyl, quinolyl or the like. A preferable one among them is thiazolyl, thiadiazolyl, pyridyl, pyrazinyl, benzothiazolyl, thiazolopyridinyl, thiazolopyrazinyl, thiazolopyrimidinyl, more preferably thiazolyl, thiadiazolyl, pyrazinyl, thiazolopyridinyl, thiazolopyrazinyl, particularly thiazolyl, thiazolopyridinyl, further particularly thiazolyl.

The term "heterocycle" in Ring T includes, for example, 5 to 9-membered mono- or bi-cyclic heterocycle optionally having 1 to 3 heteroatom(s) independently selected from oxygen atom, sulfur atom and nitrogen atom, preferably 9-membered bicyclic heterocycle, specifically cyclohexanothiazolyl, dihydrothiazolopyridinyl, tetrahydro-thiazolopyridinyl or the like.

The term "cycloalkyl" in $R^{10}$ and $R^{11}$ includes, for example, 3 to 4-membered cycloalkyl, specifically cyclopropyl, cyclobutyl, etc., particularly cyclopropyl.

The term "heterocycle" in $R^{10}$ and $R^{11}$ includes, for example, 5 to 9-membered mono- or bi-cyclic heterocycle optionally having 1 to 3 heteroatom(s) independently selected from oxygen atom, sulfur atom and nitrogen atom, preferably 5 to 7-membered monocyclic heterocycle. Specifically, azetidinyl, pyrrolidinyl, tetrahydrofuryl, piperidinyl, piperazinyl, morpholinyl, thiomorpholinyl, oxazepidinyl or perhydro-diazepinyl is preferable.

The term "cycloalkyl" in $R^2$ includes, for example, 3 to 4-membered cycloalkyl, specifically cyclopropyl, cyclobutyl or the like, particularly cyclopropyl.

The term "heterocycle" in $R^2$ includes, for example, 5 to 9-membered mono- or bi-cyclic heterocycle optionally having 1 to 3 heteroatom(s) independently selected from oxygen atom, sulfur atom and nitrogen atom, preferably 5 to 7-membered monocyclic heterocycle. Specifically, azetidinyl, pyrrolidinyl, tetrahydrofuryl, piperidinyl, piperazinyl, morpholinyl, thiomorpholinyl, oxazepidinyl or perhydro-diazepinyl is preferable.

The term "heteroaryl" in $R^3$ and $R^4$ includes, for example, 5 to 9-membered mono- or bi-cyclic heteroaryl optionally having 1 to 3 heteroatom(s) independently selected from oxygen atom, sulfur atom and nitrogen atom, preferably 5 to 6-membered monocyclic heteroaryl optionally having 1 to 3 nitrogen atom(s), specifically pyrazolyl, triazolyl, pyridyl, pyrimidyl or the like, particularly pyrimidyl.

A preferable combination of $R^3$ and $R^4$ includes a combination wherein one is substituted alkyl, or substituted or unsubstituted heteroaryl, and the other is selected from hydrogen atom or alkyl.

The heterocycle in the "substituted or unsubstituted heterocycle which $R^3$ and $R^4$ combine each other together with the adjacent nitrogen atom to form" is preferably 5 to 7-membered heterocycle containing 0 to 1 heteroatom selected from oxygen atom, nitrogen atom or sulfur atom in addition to nitrogen atom. A preferable heterocycle includes pyrrolidine, piperidine, piperazine, morpholine, thiomorpholine, homopiperidine, homopiperazine, homomorpholine, and homothiomorpholine, particularly pyrrolidine, piperidine, piperazine, morpholine or thiomorpholine.

The heterocycle in $R^5$ includes, for example, 4 to 6-membered monocyclic heterocycle. Specifically, azetidinyl, pyrrolidinyl, piperidinyl, piperazinyl, morpholinyl, thiomorpholinyl, etc. is preferable.

Each substituent on each group shown by each symbol of compound [I] means as defined below.

The substituents in "substituted amino", "substituted aminosulfonyl", "substituted aminoalkyl", "substituted amino alkanoyl", "substituted carbamoyl", "substituted carbamoylalkyl", "substituted alkyl", "substituted alkylthio", "substituted alkylsulfinyl", "substituted alkylsulfonyl", "substituted alkoxy", "substituted alkanoyl", "substituted alkynyl", "substituted cycloalkyl", "substituted cycloalkyloxy", "substituted cycloalkylcarbonyl", "substituted cyclo alkylsulfonyl", "substituted aryl", "substituted aryloxy", "substituted arylcarbonyl", "substituted arylcarbonyloxy", "substituted arylsulfonyl", "substituted arylalkylcarbonyl", "substituted heteroaryl", "substituted heteroarylthio", "substituted heteroarylsulfonyl", "substituted heteroarylalkyl", "substituted heterocycle", "substituted heterocyclyl-oxy", "substituted heterocyclyl-carbonyl", "substituted heterocyclyl-thio", "substituted heterocyclyl-sulfinyl", "substituted heterocyclyl-sulfonyl", "substituted hydroxyimino", "substituted phenyl", "substituted pyridyl", "substituted thiazolopyridinyl", "substituted pyrazinyl", "substituted pyrazolyl", "substituted imidazolyl", "substituted thiazolyl", "substituted benzothiazolyl", "substituted quinolyl", "substituted thiadiazolyl", "substituted pyrazolyl", "substituted thiazolopyrazinyl", "substituted thiazolopyrimidinyl", "substituted cyclohexanothiazolyl", "substituted dihydrothiazolopyridinyl", "substituted triazolyl", "substituted pyrimidinyl", "substituted pyrrolidinyl", "substituted tetrahydrofuryl", "substituted thiacyclohexyl", "substituted cyclopentyl", "substituted piperazinyl", "substituted piperazinylsulfonyl", "substituted homopiperazinyl", "substituted piperidinyl", "substituted morpholinyl", "substituted thiomorpholinyl", "substituted perhydrodiazepinyl", and "substituted tetrazolyl" include (1) alkyl optionally substituted with hydroxy, alkoxy, amino, mono- or di-alkylamino, carbamoyl, tetrahydrofuryl or pyridyl, (2) cycloalkyl, (3) hydroxy, (4) alkoxy, (5) cyano, (6) halogen atom, (7) mono- or di-alkylamino, (8) amino optionally substituted with alkanoyl, alkoxyalkanoyl or alkoxycarbonyl, (9) pyridyl, (10) carboxyl, (11) formyl, (12) alkanoyl optionally substituted with mono- or di-alkylamino, hydroxy, alkoxy or alkanoyloxy, (13) cycloalkylcarbonyl, (14) alkoxycarbonyl, (15) oxo, (16) alkylsulfonyl, (17) those specifically indicated in EXAMPLES and REFERENCE EXAMPLES, or the like. The same or different 1 to 3 substituent(s) selected from the above groups may be substituted.

Additionally, each preferable substituent is explained depending on each symbol ($R^1$-$R^5$ and $R^{11}$) of compound [I]. Each group of each symbol may have the same or different 1 to 3 substitutent(s) selected from the groups as defined below.

A preferable substituent of "substituted tetrazolyl" in $R^1$ includes alkyl

A preferable substituent of "substituted alkylsulfonyl" in $R^2$ includes alkoxycarbonyl, alkoxy, cycloalkyl (preferably, cyclopropyl), hydroxy, substituted or unsubstituted amino (substituent(s): 1 or 2 group(s) selected from alkyl or alkanoyl), substituted or unsubstituted heteroaryl (preferably, imidazolyl or triazolyl) (substituent(s): alkyl), alkylsulfonyl, cyano, substituted or unsubstituted heterocycle (preferably, tetrahydrofuryl, tetrahydropyranyl or dihydro-3H-isoindolyl) (substituent(s): oxo or dioxo). More preferable one among them is alkoxy, cycloalkyl (preferably, cyclopropyl), hydroxy, particularly alkoxy.

A preferable substituent of "substituted alkylthio" in $R^2$ includes alkoxy, cycloalkyl, alkoxycarbonyl, hydroxy, cyano, alkylthio, substituted or unsubstituted heterocycle (preferably, tetrahydrofuryl, tetrahydropyranyl or dihydro-3H-isoindolyl) (substituent(s): oxo or dioxo), heteroaryl (preferably, pyridyl). More preferable one among them is alkoxy, cycloalkyl, alkoxycarbonyl, hydroxy, cyano, alkylthio, heteroaryl (preferably, pyridyl).

A preferable substituent of "substituted amino" in $R^2$ includes heteroarylcarbonyl (preferably, pyridylcarbonyl), heteroarylalkanoyl (thienylalkanoyl), cycloalkylcarbonyl, cycloalkylsulfonyl, alkoxy-carbonylcarbonyl, heteroarylsulfonyl, alkylsulfonyl. More preferable one among them is alkoxycarbonylcarbonyl, alkylsulfonyl.

A preferable substituent of the substituted alkyl which is a substituent of "substituted aminosulfonyl" in $R^2$ includes amino optionally substituted with mono- or di-alkyl; carbamoyl optionally substituted with mono- or di-alkyl; hydroxy; alkoxy; heteroaryl optionally substituted with alkyl; cycloalkyl; alkoxycarbonyl; hydroxyalkoxy; heterocycle optionally substituted with alkyl; halogen atom; alkylthio. More preferable one among them is amino optionally substituted with mono- or di-alkyl; carbamoyl optionally substituted with mono- or di-alkyl; hydroxy; alkoxy; cycloalkyl; alkoxycarbonyl; heterocycle optionally substituted with alkyl; halogen atom; particularly hydroxy, alkoxy.

The heterocycle which is a substituent of substituted or unsubstituted alkyl which is a substituent of "substituted aminosulfonyl" in $R^2$ includes 5 to 9-membered mono- or bi-cyclic heterocycle optionally having 1 to 3 heteroatom(s) independently selected from oxygen atom, sulfur atom and nitrogen atom, preferably 5-membered monocyclic heterocycle, particularly tetrahydrofuryl.

A preferable substituent of the substituted heterocycle which is a substituent of "substituted aminosulfonyl" in $R^2$ includes alkyl.

A preferable substituent of "substituted heterocyclyl-thio" in $R^2$ includes hydroxy; alkyl; oxo; alkanoyl; hydroxyalkyl; carbamoyl optionally substituted with mono- or di-alkyl; heteroaryl; aminosulfonyl optionally substituted with mono- or di-alkyl; amino optionally substituted with mono- or di-alkyl; alkylsulfonyl; alkoxy; alkoxyalkyl. More preferable one among them is hydroxy; alkyl; carbamoyl optionally substituted with mono- or di-alkyl; oxo; alkoxy; alkoxyalkyl; particularly alkyl.

A preferable substituent of "substituted heterocyclyl-sulfinyl" in $R^2$ includes hydroxy; alkyl; oxo; alkanoyl; hydroxyalkyl; carbamoyl optionally substituted with mono- or di-alkyl; heteroaryl; aminosulfonyl optionally substituted with mono- or di-alkyl; amino optionally substituted with mono- or di-alkyl; alkylsulfonyl; alkoxy; alkoxyalkyl. More preferable one among them is hydroxy; alkyl; carbamoyl optionally substituted with mono- or di-alkyl; oxo; alkoxy; alkoxyalkyl; particularly alkyl.

A preferable substituent of "substituted heterocyclyl-sulfonyl" in $R^2$ includes hydroxy; alkyl; oxo; alkanoyl; hydroxyalkyl; carbamoyl optionally substituted with mono- or di-alkyl; heteroaryl; aminosulfonyl optionally substituted with mono- or di-alkyl; amino optionally substituted with mono- or di-alkyl; alkylsulfonyl; alkoxy; alkoxyalkyl. More preferable one among them is hydroxy; alkyl; carbamoyl optionally substituted with mono- or di-alkyl; oxo; alkoxy; alkoxyalkyl.

A preferable substituent of "substituted heteroarylsulfonyl" in $R^2$ includes alkyl.

A preferable substituent of "substituted alkoxy" in $R^2$ includes cycloalkyl.

A preferable substituent of "substituted alkylsulfinyl" in $R^2$ includes alkoxycarbonyl, alkoxy, alkoxyalkyl, cycloalkyl (preferably, cyclopropyl), hydroxy, substituted or unsubstituted amino (substituent(s): 1 or 2 group(s) selected from alkyl or alkanoyl), substituted or unsubstituted heteroaryl (preferably, imidazolyl, triazolyl) (substituent(s): alkyl), alkylsulfonyl, cyano, substituted or unsubstituted heterocycle (preferably, tetrahydrofuryl, tetrahydropyranyl, dihydro-3H-isoindolyl) (substituent(s): oxo, dioxo). More preferable one among them is alkoxy, cycloalkyl (preferably, cyclopropyl), hydroxy, particularly hydroxy.

A preferable substituent of "substituted heteroaryl" in $R^2$ includes alkyl.

A preferable substituent of "substituted alkyl" in $R^{11}$ includes alkoxycarbonyl, alkoxy, cycloalkyl (preferably, cyclopropyl), hydroxy, substituted or unsubstituted amino (substituent(s): 1 or 2 group(s) selected from alkyl or alkanoyl), substituted or unsubstituted heteroaryl (preferably, imidazolyl, triazolyl) (substituent(s): alkyl), alkylsulfonyl, cyano, substituted or unsubstituted heterocycle (preferably, tetrahydrofuryl, tetrahydropyranyl, dihydro-3H-isoindolyl) (substituent(s): oxo, dioxo). More preferable one among them is alkoxy, cycloalkyl (preferably, cyclopropyl), hydroxy, dialkylamino, particularly alkoxy.

A preferable substituent of "substituted cycloalkyl" in $R^{11}$ includes hydroxy; alkyl; oxo; alkanoyl; hydroxyalkyl; carbamoyl optionally substituted by mono- or di-alkyl; heteroaryl; aminosulfonyl optionally substituted by mono- or di-alkyl; amino optionally substituted by mono- or di-alkyl; alkylsulfonyl; alkoxy; alkoxyalkyl. More preferable one among them is hydroxy; alkyl; carbamoyl optionally substituted by mono- or di-alkyl; oxo; alkoxy; alkoxyalkyl, particularly alkyl.

A preferable substituent of "substituted heteroaryl" in $R^{11}$ includes hydroxy; alkyl; alkanoyl; hydroxyalkyl; carbamoyl optionally substituted by mono- or di-alkyl; heteroaryl; aminosulfonyl optionally substituted by mono- or di-alkyl; amino optionally substituted by mono- or di-alkyl; alkylsulfonyl; alkoxy; alkoxyalkyl. More preferable one among them is hydroxy; alkyl; carbamoyl optionally substituted by mono- or di-alkyl; alkoxy; alkoxyalkyl, particularly alkyl.

A preferable substituent of "substituted alkyl" in $R^3$ and $R^4$ includes hydroxy, alkoxy, dialkylamino, cycloalkyl, substituted or unsubstituted heterocycle, or substituted or unsubstituted heteroaryl. Particularly preferable one includes substituted or unsubstituted heteroaryl.

The heterocycle of "substituted or unsubstituted heterocycle" which is a substituent of "substituted alkyl" in $R^3$ and $R^4$ includes 4 to 6-membered monocyclic heterocycle optionally having 1 to 3 heteroatom(s) independently selected from oxygen atom, sulfur atom and nitrogen atom, specifically oxetanyl, tetrahydrofuryl, pyrrolidinyl, piperidinyl, tetrahydropyranyl, tetrahydrothiopyranyl. Particularly preferable one is tetrahydropyranyl.

The heteroaryl of "substituted or unsubstituted heteroaryl" which is a substituent of "substituted alkyl" in $R^3$ and $R^4$ includes 5 to 9-membered mono- or bi-cyclic heteroaryl optionally having 1 to 3 heteroatom(s) independently selected from oxygen atom, sulfur atom and nitrogen atom, preferably 5 to 6-membered monocyclic heteroaryl optionally having 1 to 3 nitrogen atom(s), specifically pyrazolyl, imidazolyl, triazolyl, pyridyl or pyrimidyl. Particularly preferable one is pyrimidyl.

A preferable substituent of substituted heterocycle of "substituted or unsubstituted heterocycle which $R^3$ and $R^4$ combine each other together with the adjacent nitrogen atom to form", "substituted heteroaryl" in $R^3$ and $R^4$, and substituted heteroaryl and substituted heterocycle which are substituents of "substituted alkyl" in $R^3$ and $R^4$ includes alkyl, hydroxy, oxo, substituted or unsubstituted amino, and alkoxy. Particularly preferable one includes alkyl, hydroxy, oxo and alkoxy.

A preferable substituent of "substituted alkoxy" in $R^5$ includes substituted or unsubstituted amino (substituent(s): 1 or 2 group(s) selected from alkyl or alkoxycarbonyl); alkoxycarbonyl; carbamoyl optionally substituted by mono- or di-alkyl; carboxyl; hydroxy; substituted or unsubstituted heterocycle (substituent(s): oxo); trialkylsilyloxy; alkoxy. More preferable one among them is amino optionally substituted by mono- or di-alkyl; carbamoyl optionally substituted by mono- or di-alkyl; hydroxy, particularly amino optionally substituted by mono- or di-alkyl; hydroxy.

A preferable substituent of "substituted aminosulfonyl" in $R^5$ includes alkyl. Therefore, said substituent is mono- or di-alkyl, preferably dialkyl.

A preferable substituent of "substituted alkylthio" in $R^5$ includes amino optionally substituted with mono- or di-alkyl; alkoxycarbonylamino; halogen atom; hydroxy; carboxyl; carbamoyl optionally substituted with mono- or di-alkyl; alkoxycarbonyl. More preferable one among them is amino optionally substituted with mono- or di-alkyl; alkoxycarbonylamino; hydroxy; carbamoyl optionally substituted with mono- or di-alkyl; particularly dialkylcarbamoyl.

A preferable substituent of "substituted heterocyclyl-sulfonyl" in $R^5$ includes alkyl.

A preferable substituent of "substituted cycloalkyl" in $R^5$ includes amino optionally substituted with mono- or di-alkyl.

A preferable substituent of "substituted cycloalkyloxy" in $R^5$ includes amino optionally substituted with mono- or di-alkyl.

A preferable substituent of "substituted carbamoyl" in $R^5$ includes substituted or unsubstituted alkyl (substituent(s): 1 or 2 group(s) selected from hydroxy; cycloalkyl; heterocycle; amino optionally substituted with mono- or di-alkyl; heteroaryl), cycloalkyl, heteroaryl. More preferable one among them is substituted or unsubstituted alkyl (substituent(s): 1 or 2 group(s) selected from hydroxy, heterocycle, dialkylamino, heteroaryl), cycloalkyl.

A preferable substituent of "substituted heteroarylthio" in $R^5$ includes alkyl.

A preferable substituent of "substituted amino" in $R^5$ includes alkyl, substituted or unsubstituted aminoalkyl (substituent(s): 1 or 2 group(s) selected from alkyl or alkanoyl), alkanoyl, hydroxyalkyl, alkoxycarbonyl. More preferable one among them is alkyl, and hence, mono- or di-alkyl, particularly di-alkyl.

A preferable substituent of "substituted heteroaryl" in $R^5$ includes alkyl.

A preferable substituent of "substituted alkynyl" in $R^5$ includes hydroxy, amino optionally substituted with mono- or di-alkyl. More preferable one among them is hydroxy, dialkylamino.

A preferable substituent of "substituted heterocyclyl-carbonyl" in $R^5$ includes hydroxy, alkyl, oxo, hydroxyalkyl, alkanoyl. More preferable one among them is hydroxy, alkyl, hydroxyalkyl.

A preferable substituent of "substituted heterocyclyl-oxy" in $R^5$ includes hydroxy, alkyl, oxo, hydroxyalkyl, alkanoyl. More preferable one among them is alkyl, oxo.

A preferable substituent of "substituted heterocycle" in $R^5$ includes hydroxy, alkyl, oxo, hydroxyalkyl, alkanoyl. More preferable one among them is oxo.

A preferable substituent of "substituted heterocyclyl-thio" in $R^5$ includes hydroxy, alkyl, oxo, hydroxyalkyl, alkanoyl. More preferable one is alkyl, alkanoyl.

A preferable substituent of "substituted alkyl" in $R^5$ includes substituted or unsubstituted heterocycle, substituted or unsubstituted amino, substituted or unsubstituted alkoxy, substituted or unsubstituted carbamoyl, hydroxy, trialkylsilyloxy, substituted or unsubstituted alkylthio, substituted or unsubstituted heterocyclyl-oxy, heteroaryl, substituted or unsubstituted hydroxyimino, halogen atom, more preferably substituted or unsubstituted heterocycle, substituted or unsubstituted amino, substituted or unsubstituted alkoxy, hydroxy, substituted or unsubstituted alkylthio, substituted or unsubstituted heterocyclyl-oxy, substituted or unsubstituted hydroxyimino, halogen atom, further preferably substituted or unsubstituted heterocycle, substituted or unsubstituted alkoxy, substituted or unsubstituted heterocyclyl-oxy, particularly substituted or unsubstituted heterocycle, substituted or unsubstituted alkoxy, further particularly substituted or unsubstituted heterocycle.

A preferable substituent of substituted heterocycle which is the substituent of "substituted alkyl" in $R^5$ includes alkyl; oxo; alkoxyalkanoyl; alkanoyl; alkoxy; alkanoylamino; cycloalkylcarbonylamino; tri(halogeno)alkanoylamino; formylamino; alkoxycarbonylamino; hydroxy; cycloalkylcarbonyl; tri(halogeno)alkyl; alkoxycarbonyl; formyl; amino optionally substituted with mono- or di-alkyl; aminosulfonyl optionally substituted with mono- or di-alkyl; alkylsulfonyl; heteroaryl; alkoxycarbonylalkyl; alkanoyloxyalkanoyl; alkoxycarbonylcarbonyl; aminoalkanoyl optionally substituted with mono- or di-alkyl; substituted or unsubstituted carbamoyl (substituent(s): 1 or 2 group(s) selected from alkyl or alkoxy); hydroxyalkanoyl; di(halogeno)alkanoyl; substituted or unsubstituted heterocyclyl-carbonyl (substituent(s): oxo); substituted or unsubstituted hydroxyimino (substituent(s): alkoxycarbonyl); carboxyl; hydroxyalkoxy; alkoxyalkoxy; halogen atom; alkanoyloxy. More preferable one among them is alkyl; oxo; alkoxyalkanoyl; alkanoyl; alkoxy; alkanoylamino; cycloalkylcarbonylamino; tri(halogeno)alkanoylamino; formylamino; alkoxylcarbonylamino; cycloalkylcarbonyl; tri(halogeno)alkyl; alkoxy-carbonyl; formyl; amino optionally substituted with mono- or di-alkyl; aminosulfonyl optionally substituted with mono- or di-alkyl; alkylsulfonyl; heteroaryl; alkoxycarbonylalkyl; alkanoyloxyalkanoyl; alkoxycarbonylcarbonyl; aminoalkanoyl optionally substituted with mono- or di-alkyl; carbamoyl optionally substituted with mono- or di-alkyl; hydroxyalkanoyl; di(halogeno)alkanoyl; substituted or unsubstituted heterocyclyl-carbonyl (substituent(s): oxo); substituted or unsubstituted hydroxyimino (substituent(s): alkoxycarbonyl); more preferably alkyl; oxo; alkoxyalkanoyl; alkanoyl; formyl; amino optionally substituted with mono- or di-alkyl; alkylsulfonyl; alkanoyloxyalkanoyl; aminoalkanoyl optionally substituted with mono- or di-alkyl; hydroxyalkanoyl; more preferably alkyl, alkanoyl, formyl, hydroxyalkanoyl, particularly alkyl, alkanoyl.

A preferable substituent of the substituted amino which is the substituent of "substituted alkyl" in $R^5$ includes alkyl; carbamoylalkyl optionally substituted with mono- or di-alkyl; substituted or unsubstituted aminoalkyl (substituent(s): 1 or 2 group(s) selected from alkyl or alkanoyl); alkoxyalkyl; hydroxyalkyl; alkoxyalkanoyl; heteroaryl; heteroarylalkyl. More preferable one among them is alkyl; carbamoylalkyl optionally substituted with mono- or di-alkyl; aminoalkyl optionally substituted with mono- or di-alkyl; alkoxyalkyl; heteroaryl; particularly alkyl.

A preferable substituent of the substituted alkoxy which is the substituent of "substituted alkyl" in $R^5$ includes hydroxy, alkoxy.

A preferable substituent of the substituted carbamoyl which is the substituent of "substituted alkyl" in $R^5$ includes alkyl, alkoxy.

A preferable substituent of the substituted heterocyclyl-oxy which is the substituent of "substituted alkyl" in $R^5$ includes alkanoyl, alkyl, formyl, cycloalkylcarbonyl, alkoxy-alkanoyl, alkylsulfonyl. More preferable one among them is alkanoyl, alkyl, particularly alkanoyl.

A preferable substituent of the substituted hydroxyimino which is the substituent of "substituted alkyl" in $R^5$ includes alkoxycarbonyl.

The heterocycle of "substituted or unsubstituted heterocycle" which is a substituent of "substituted alkyl" in $R^5$ includes 5 to 9-membered mono- or bi-cyclic heterocycle optionally having 1 to 3 heteroatom(s) independently selected from oxygen atom, sulfur atom and nitrogen atom, preferably 4 to 6-membered monocyclic heterocycle optionally having 1 to 3 nitrogen atom(s), specifically azetidinyl, pyrrolidinyl, piperidinyl, piperazinyl, morpholinyl, thiomorpholinyl, perhydrodiazepinyl, octahydropyrrolo[1,2-a]piperazinyl. More preferable one among them is piperazinyl, morpholinyl, particularly piperazinyl.

The heterocycle of "substituted or unsubstituted heterocyclyl-oxy" which is a substituent of "substituted alkyl" in $R^5$ includes 5 to 9-membered mono- or bi-cyclic heterocycle optionally having 1 to 3 heteroatom(s) independently selected from oxygen atom, sulfur atom and nitrogen atom, preferably 4 to 6-membered monocyclic heterocycle optionally having 1 to 3 nitrogen atom(s), specifically azetidinyl, pyrrolidinyl, piperidinyl, piperazinyl, morpholinyl, thiomorpholinyl, perhydrodiazepinyl, octahydropyrrolo[1,2-a]piperazinyl. More preferable one among them is piperidinyl.

Among compound [I], a preferable compound includes a compound wherein Ring A is phenyl, Ring T is 2-thiazolyl or 2-thiazolopyridyl, $R^1$ is hydrogen atom, $R^2$ is cyclopropylsulfonyl or alkoxyalkylsulfonyl, $R^3$ and $R^4$ combine each other together with the adjacent nitrogen atom to form morpholine or pyrrolidine, $R^5$ is piperazinyl-substituted alkyl optionally substituted by 1 to 3 substituent(s) selected from alkyl, oxo, alkanoyl and alkoxyalkanoyl.

Further preferable compound includes a compound wherein Ring A is phenyl, Ring T is 2-thiazolopyridyl, $R^1$ is hydrogen atom, $R^2$ is cyclopropylsulfonyl or alkoxyalkylsulfonyl, $R^3$ and $R^4$ combine each other together with the adjacent nitrogen atom to form morpholine or pyrrolidine, $R^5$ is alkoxy substituted by amino optionally substituted by 1 or 2 alkyl(s), amino substituted by amino optionally substituted by 1 or 2 alkyl(s), or alkylamino substituted by amino optionally substituted by 1 or 2 alkyl(s).

Among compound [I] of the present invention, further preferable specific compound includes any compounds described in all EXAMPLES or REFERENCE EXAMPLES. Additionally, each specific example of each group (Ring A, T, $R^1$ to $R^6$, $R^{10}$ and $R^{11}$) includes the corresponding compound specifically disclosed in EXAMPLES or REFERENCE EXAMPLES.

Compound [I] of the present invention encompasses a mixture of stereoisomers, or each stereoisomer in the pure or substantively pure form. For example, in case that the compound of the present invention has one or more asymmetric center(s) on any carbon atom, compound [I] may exist in the form of its enantiomer or diastereomer or a mixture thereof. The compound of the present invention encompasses its isomers or a mixture thereof. Also, in case that compound [I] of the present invention contains double bonds, geometric isomers (cis-isomer, trans-isomer) may exist, and in case that compound [I] of the present invention contains unsaturated bonds such as carbonyl, tautomers may exist, but the compound of the present invention encompasses all these isomers or a mixture thereof. A geometric isomer, preferably trans-isomer (E-isomer), may exist in hydrazone moiety of compound [I] of the present invention.

A pharmaceutically acceptable salt of compound [I] includes, for example, an inorganic acid salt such as hydrochloride, sulfate, phosphate or hydrobromide, or an organic acid salt such as acetate, fumarate, oxalate, citrate, methanesulfonate, benzenesulfonate, tosylate or maleate. Also, in case of having a substituent such as carboxyl, said salt includes a salt with a base such as alkali metal salt such as sodium salt or potassium salt, or alkali earth metal salt such as calcium salt. The pharmaceutically acceptable salt of compound [I] of the present invention also includes an intramolecular salt, and compound [I] and its salt may be in the form of a solvate thereof such as hydrate.

Compound [I] of the present invention or a pharmaceutically acceptable salt thereof may be formulated to a pharmaceutical composition comprising a therapeutically effective amount of the compound and a pharmaceutically acceptable carrier. The pharmaceutically acceptable carrier may include diluents, binding agents (syrup, gum acacia, gelatin, sorbit, tragacanth or polyvinylpyrrolidone), excipients (lactose, sucrose, cornstarch, potassium phosphate, sorbit or glycine), lubricants (magnesium stearate, talc, polyethylene glycol or silica), disintegrants (Irish potato starch) and wetting agents (sodium lauryl sulfate), or the like.

Compound [I] of the present invention or a pharmaceutically acceptable salt thereof may be administered orally or parenterally and used in an appropriate pharmaceutical formulation. The appropriate pharmaceutical formulation for oral administration includes, for example, a solid formulation such as a tablet, a granule, a capsule or a powder, or the form of a solution, a suspension or an emulsion. The appropriate pharmaceutical formulation for parenteral administration includes a suppository; an injectable solution or an intravenous fluid preparation using distilled water for injection, saline or glucose aqueous solution; or an inhaler; or the like.

Compound [I] of the present invention or a pharmaceutically acceptable salt thereof, or a pharmaceutical formulation thereof may be combined with one or more other medicine(s) selected from antidiabetic and antihyperglycemic agents. In this case, the concept of the term "combine" includes administering with these other medicines simultaneously or separately with optional interval as well as administering as one pharmaceutical formulation formulated together with these other medicines. These other medicines include sulfonylurea (for example, glyburide, glimepiride, glipiride, glipizide, chlorpropamide, gliclazide, glisoxepide, acetohexamide, glibonuride, tolbutamide, tolazamide, carbutamide, gliquidone, glihexamid, phenbutamide, tolcyclamide or the like), biguanide (for example, metformin, phenformin, buformin or the like), glucagon antagonist (for example, peptidic or nonpeptidic glucagon antagonist), a glucosidase inhibitor (for example, acarbose, miglitol or the like), an insulin sensitizer (for example, troglitazone, rosiglitazone, pioglitazone or the like), an antiobesity agent (for example, sibutramine, orlistat or the like) or the like.

The dose of compound [I] of the present invention or a pharmaceutically acceptable salt thereof depends on methods of administration, ages, body weights or conditions of patients, but usually about 0.01 to about 100 mg/kg per day, preferably about 0.1 to about 10 mg/kg.

Compound [I] of the present invention may be prepared according to the following methods.

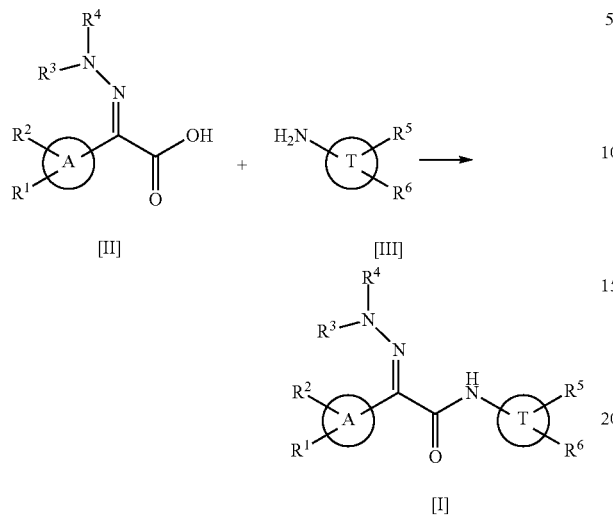

In the above scheme, Ring A, T, $R^1$ to $R^6$ have the same meanings as mentioned above.

The reaction of compound [II] with compound [III] may be carried out in an appropriate solvent in the presence or absence of a condensing agent. As the condensing agent, any of N-ethyl-N'-(3-dimethylaminopropyl)carbodiimide, N,N'-dicyclohexylcarbodiimide, 1-methyl-2-bromopyridinium iodide, N,N'-carbonyldiimidazole, diphenyl phosphoryl azide, benzotriazol-1-yloxytris(dimethylamino)phosphonium hexafluorophosphate, 4-(4,6-dimethoxy[1.3.5]triazin-2-yl)-4-methyl-morpholinium chloride, fluoro-N,N,N',N'-tetramethylformamidinium hexafluorophosphate or the like may be preferably used. As the solvent, any of a single solvent or a mixed solvent of water, methanol, isopropanol, ethanol, methylene chloride, THF, DMF, dimethylacetamide, chloroform or the like may be preferably used. The reaction preferably proceeds at −78° C. to 100° C., more preferably at −25° C. to 25° C. The reaction may be accelerated by adding potassium carbonate, sodium carbonate, sodium bicarbonate or triethylamine, N,N-diisopropylethylamine, N-methylmorpholine, pyridine, N,N-dimethylaminopyridine, picoline, lutidine or the like as a base, and N-hydroxysuccinimide, 3-hydroxy-3,4-dihydro-4-oxo-1,2,3-benzotriazole, N,N-dimethylaminopyridine or N-hydroxybenzotriazole or the like as an additive.

The reaction from compound [II] to compound [I] may be carried out by converting compound [II] into a reactive intermediate such as an acid chloride or a mixed acid anhydride, followed by reacting with compound [III]. The conversion into an acid chloride may be preferably carried out by using thionyl chloride, phosphorus oxychloride, phosphorus pentachloride; or triphenylphosphine in the presence of carbon tetrachloride, or the like; and the conversion into a mixed acid anhydride may be carried out by using diphenyl phosphoryl chloride, methanesulfonyl chloride, ethyl chloroformate, isobutyl chloroformate or the like in the presence of a base such as triethylamine. As the solvent, any of a single solvent or a mixed solvent of methylene chloride, chloroform, THF, DMF or the like may be preferably used. The reaction preferably proceeds at −78° C. to 100° C., more preferably −25° C. to 25° C. The reaction of the reactive intermediate with compound [II] may be carried out by using any of a single solvent of methylene chloride, chloroform, THF, DMF or the like, or a mixed solvent thereof as the solvent at −78° C. to 100° C., preferably −25° C. to 25° C.

A mixture of cis- and trans-isomers of hydrazone moiety may be also used as compound [II] in the similar reaction to the following (LL) to prepare compound [I].

Compound [II] may be prepared as follows:

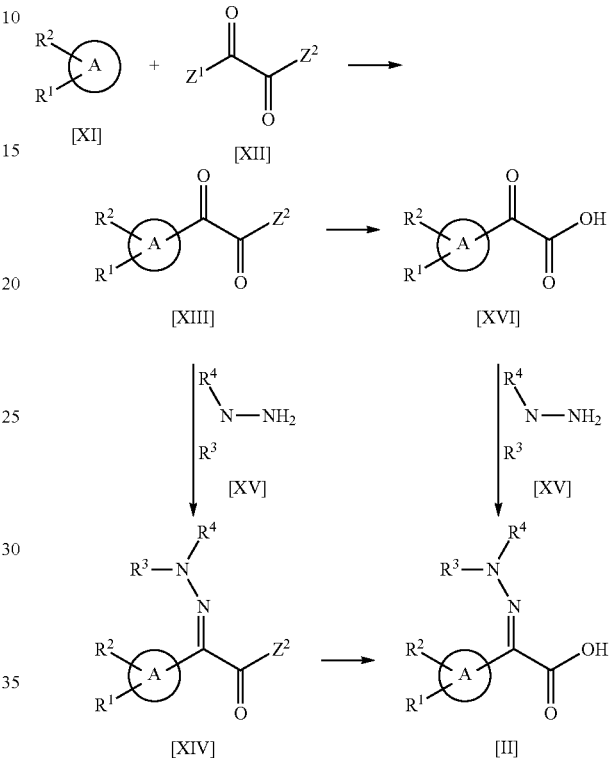

wherein $Z^1$ is halogen atom, $Z^2$ is alkoxy, and the other symbols have the same meanings as defined above.

The reaction of compound [XI] with compound [XII] may be carried out in an appropriate solvent (chloroform, methylene chloride, etc.) in the presence of an acid (aluminum chloride, etc.).

The reaction of compound [XIII] with hydrazine [XV] or a salt thereof with an appropriate acid may be carried out in an appropriate solvent (methanol, chloroform, etc.) in the presence or absence of a base. The base used in the reaction includes pyridine, picoline, lutidine, N,N-dimethylaniline, triethylamine, etc. A mixture of cis- and trans-isomers of the generated hydrazone may be separated by silica gel column chromatography, and the cis-isomer may be converted into the desired trans-isomer or a mixture of cis- and trans-isomers by an acid treatment (trifluoroacetic acid, acetic acid, hydrochloric acid, sulfuric acid, phosphoric acid, etc.).

The resulting product may be treated with a base (sodium hydroxide, etc.) and hydrolyzed in the moiety of $Z^2$ to give compound [II]. A mixture of cis- and trans-isomers of hydrazone moiety may be also used as compound [XIV] in the similar reaction to the following (KK) to give compound [II].

Compound [XIII] may be treated with a base (sodium hydroxide, etc.) and hydrolyzed in the moiety of $Z^2$ to give compound [XVI], followed by reacted with hydrazine and compound [XV] in an appropriate solvent (methanol, methylene chloride, chloroform, DMF, etc.) in the presence or absence of a base to give compound [II].

Compound [XV] may be prepared by nitrosating an aromatic or aliphatic amine to reduce in a conventional manner described, for example, in Organic Synthesis II, 211 (1943), Organic Synthesis II, 290 (1943), Organic Synthesis II, 418 (1943), Organic Synthesis II, 460 (1943), Organic Synthesis V, 893 (1973), Organic Synthesis V, 542 (1988), etc. Alternatively, it may be also prepared by reacting hydrazine protected on one side with heteroaryl halide or alkyl halide in an appropriate solvent (chloroform, methylene chloride, tetrahydrofuran, etc.) in the presence of a base.

Compound [I] may be further converted in the following manner.

(A) A compound containing sulfinyl (SO) or sulfonyl ($SO_2$) on $R^1$-$R^6$ and $R^{11}$ among the objective compound [I] of the present invention may be prepared by an oxidation using any conventional method for converting the corresponding sulfide compound into a sulfinyl or sulfonyl compound. For example, the oxidation may be carried out by treating with an oxidizing agent in an appropriate solvent (methylene chloride, chloroform, THF, methanol, water or the like, or a mixed solvent thereof). As the oxidizing agent, peracids such as hydrogen peroxide, m-chloroperbenzoic acid, peracetic acid or the like as well as Oxone™ ("a mixture of potassium peroxybisulfate, dipotassium sulfate and potassium bisulfate" manufactured by DuPont) may be preferably used, and the reaction may be preferably carried out at −78° C. to 100° C.

(B) A compound having a group of the formula:

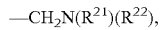
—$CH_2N(R^{21})(R^{22})$, wherein $R^{21}$ and $R^{22}$ are substituents of the substituted amino group described herein or $R^{21}$ and $R^{22}$ combine together with nitrogen atom of said amino group to form a heterocycle having 1 to 3 heteroatom(s) independently selected from oxygen atom, sulfur atom and nitrogen atom wherein the heterocycle may be substituted,
on $R^1$-$R^6$ among the objective compound [I] may be also prepared by reacting the compound wherein the corresponding site is formyl with a substituted or unsubstituted amine of the formula:

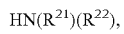
$HN(R^{21})(R^{22})$, wherein the symbols have the same meanings as mentioned above (hereinafter, this compound is referred to as "a substituted or unsubstituted amine", and the group after removing of hydrogen atom from the substituted or unsubstituted amine is referred to as "a substituted or unsubstituted amino"),
under reductive condition, so-called "reductive amination". The reaction may be carried out in any conventional manner of the reductive amination. For example, the reaction may be preferably carried out by using a reducing agent (sodium borohydride, sodium triacetoxyborohydride, sodium cyanoborohydride or the like) in an appropriate solvent (methanol, methylene chloride, chloroform, acetic acid or a mixture thereof) at −78° C. to 100° C.

(C) Among the objective compound [I], a compound wherein nitrogen atom on $R^1$-$R^6$ is substituted with a substituted or unsubstituted alkanoyl such as alkanoyl, cycloalkylcarbonyl, alkoxyalkanoyl, alkanoyloxyalkanoyl or the like, which is simply referred to as substituted or unsubstituted alkanoyl hereinafter, may be also prepared by an alkanoylation of the corresponding compound wherein the nitrogen atom is unsubstituted (for example, a compound wherein $R^5$ is piperazinylmethyl, piperazinylcarbonyl or piperazinylsulfonyl or the like). The alkanoylation may be carried out by using any conventional method of an amide formation usually used in peptide synthesis or the like. For example, the alkanoylation may be preferably carried out by using an acid chloride, an acid anhydride or an ester in an appropriate solvent (methylene chloride, THF, DMF, N,N-dimethylacetamide, chloroform or a mixed solvent thereof) in the presence or absence of a base (triethylamine, pyridine or the like) at −78° C. to 100° C. The reaction may be also carried out, for example, in an appropriate solvent in the presence or absence of a condensing agent. As the condensing agent, any of N-ethyl-N'-(3-dimethylaminopropyl)carbodiimide, N,N'-dicyclohexylcarbodiimide, 1-methyl-2-bromopyridinium iodide, N,N'-carbonyldiimidazole, diphenylphosphoryl azide, benzotriazol-1-yloxytris(dimethylamino)phosphonium hexafluorophosphate, 4-(4,6-dimethoxy[1.3.5]triazin-2-yl)-4-methylmorpholinium chloride, fluoro-N,N,N',N'-tetramethylformamidinium hexafluorophosphate or the like may be preferably used. As the solvent, any of a single solvent or a mixed solvent of water, methanol, isopropanol, ethanol, methylene chloride, THF, DMF, N,N-dimethylacetamide, chloroform or the like may be preferably used. The reaction preferably proceeds at −78° C. to 100° C., more preferably −25° C. to 25° C. The proceed of the reaction may be promoted by adding potassium carbonate, sodium carbonate, sodium bicarbonate or triethylamine, diisopropylethylamine, N-methylmorpholine, pyridine, N,N-dimethylaminopyridine, picoline, lutidine or the like as a base, and N-hydroxysuccinimide or 3-hydroxy-3,4-dihydro-4-oxo-1,2,3-benzotriazole, N,N-dimethylaminopyridine, N-hydroxybenzotriazole or the like as an additive.

(D) A compound having substituted or unsubstituted aminocarbonyl, i.e. substituted or unsubstituted carbamoyl, on $R^1$-$R^6$ among the objective compound [I] may be prepared by reacting a compound wherein the corresponding site is carboxy with a substituted or unsubstituted amine. The reaction may be carried out in the similar manner as the reaction of the above (C).

(E) A compound wherein $R^5$ or $R^6$ has substituted or unsubstituted alkoxymethyl, or substituted or unsubstituted heteroarylmethyl among the objective compound [I] may be also prepared by converting a compound wherein the corresponding site is hydroxymethyl into alkanoylmethyl, preferably acetyloxymethyl, in any conventional esterification manner, followed by condensing substituted or unsubstituted alkanol, cycloalkanol, alkylthio or a heterocycle compound having hydroxyl group, or substituted or unsubstituted heteroaryl compound having hydrogen atom on nitrogen atom, e.g., pyrazole or the like. The condensing reaction may be preferably carried out as neat or in an appropriate solvent (THF, dioxane, methylene chloride, chloroform, toluene, benzene or the like) in the presence or absence of an acid (p-toluenesulfonic acid, hydrochloric acid, sulfuric acid, trifluoroacetic acid or the like) at −78° C. to 200° C., more preferably 25° C. to 100° C.

(F) A compound having hydroxymethyl on $R^1$-$R^6$ among the objective compound [I] may be prepared by reducing a compound wherein the corresponding site is formyl in any conventional manner of reducing formyl to alcohol. For example, the reaction may be preferably carried out by using a reducing agent (sodium borohydride, sodium triacetoxyborohydride, diborane, diisobutylaluminum hydride, lithium aluminum hydride or the like) in an appropriate solvent (methanol, ethanol, methylene chloride, chloroform, dioxane, THF or the like) at −78° C. to 100° C.

(G) A compound having carboxyl on $R^1$-$R^6$ among the objective compound [I] may be prepared by oxidizing a compound wherein the corresponding site is formyl in any conventional manner of oxidizing formyl to carboxyl. The oxidation may be preferably carried out by, for example, using an oxidizing agent (sodium chlorite, potassium permanganate, pyridinium dichromate or the like) in an appropriate solvent (DMF, dimethylsulfoxide, acetone, t-butanol, water, methylene chloride, chloroform or the like) at −78° C. to 100° C.

(H) A compound having alkoxycarbonyl on $R^1$-$R^6$ among the objective compound [I] may be also prepared by esterifying a compound wherein the corresponding site is carboxyl in any conventional manner of esterifying carboxyl to alkoxycarbonyl. The esterification may be preferably carried out by, for example, using an acid (sulfuric acid, hydrochloric acid, p-toluenesulfonic acid) in an appropriate solvent (methanol, ethanol, isopropanol, t-butanol or the like) at −78° C. to 200° C., more preferably 0° C. to 100° C.

Additionally, the esterification may be also carried out by converting the carboxyl compound to a reactive intermediate such as an acid halide with a halogenating agent (oxalyl chloride, thionyl chloride or the like) in an appropriate solvent (methylene chloride, chloroform, THF, dioxane or the like), followed by using alkanol (methanol, ethanol, isopropanol or the like) at −78° C. to 200° C.

(I) A compound having carboxyl on $R^1$-$R^6$ among the objective compound [I] may be also prepared by hydrolyzing a compound wherein the corresponding site is alkoxycarbonyl in any conventional manner of ester hydrolysis. The hydrolysis may be preferably carried out by using a base (sodium hydroxide, potassium hydroxide, potassium carbonate, lithium hydroxide or the like) in an appropriate solvent (alcoholic solvent such as methanol, ethanol, or dioxane, THF, water or the like, or a mixed solvent thereof) at −78° C. to 200° C., more preferably 0° C. to 100° C.

Additionally, the hydrolysis may be also preferably carried out by using an acid (sulfuric acid, hydrochloric acid or the like) in an appropriate solvent (THF, dioxane, acetic acid, water or the like, or a mixed solvent thereof) at −78° C. to 200° C.

(J) A compound having formyl on $R^1$-$R^6$ among the objective compound [I] may be also prepared from a compound wherein the corresponding site is carboxyl in any conventional manner of reducing carboxyl to aldehyde. The reaction may be preferably carried out by synthesizing an acid halide using a halogenating agent (oxalyl chloride, thionyl chloride or the like) in an appropriate solvent (methylene chloride, chloroform, THF or the like, or a mixed solvent thereof), followed by reducing the acid halide with a metal catalyst (palladium carbon, platinum dioxide or the like) under hydrogen at −78° C. to 200° C.

(K) A compound having hydroxymethyl on $R^1$-$R^6$ among the objective compound [I] may be prepared by using any conventional method of a reduction of ester or carboxylic acid to alcohol. For example, the reaction may be preferably carried out by treating the corresponding carboxyl or alkoxycarbonyl with a reducing agent (sodium borohydride, diborane, lithium aluminum hydride, diisobutylaluminum hydride or the like) in an appropriate solvent (methylene chloride, chloroform, THF or the like) at −78° C. to 200° C.

(L) A compound having carboxyl on $R^1$-$R^6$ among the objective compound [I] may be prepared by using any conventional method of an oxidation of a primary alcohol to carboxylic acid. For example, the reaction may be preferably carried out by using a compound wherein the corresponding site is hydroxymethyl with an oxidizing agent (chromium trioxide, pyridinium dichromate or the like) in an appropriate solvent (methylene chloride, acetone, chloroform, DMF or the like) at, for example, 0° C. to 100° C.

(M) A compound having amino on $R^1$-$R^6$ among the objective compound [I] may be carried out by using any conventional method of a reduction of nitro to amine. For example, the reaction may be carried out by treating a compound wherein the corresponding site is nitro with a metal catalyst (palladium carbon, platinum dioxide or the like) in an appropriate solvent (methanol, ethanol, DMF, THF, dioxane or the like) under hydrogen at −78° C. to 200° C.

Additionally, the process may be also preferably carried out by using a reducing agent (stannous chloride, iron, zinc or the like) in an appropriate solvent (an alcoholic solvent such as methanol, ethanol, or methylene chloride, chloroform, THF, dioxane, acetic acid, water or the like, or a mixed solvent thereof) at −78° C. to 200° C., more preferably 0° C. to 100° C.

(N) A compound having halogenosulfonyl on $R^1$-$R^6$ among the objective compound [I] may be prepared by reacting a compound wherein the corresponding site is amino under so-called Sandmayer reaction condition to halogenosulfonylate via a diazonium salt. The formation of a diazonium salt may be preferably carried out by, for example, using an oxidizing agent (sodium nitrite, isoamyl nitrite, t-butyl nitrite or the like) in an appropriate solvent (water, methylene chloride, chloroform, THF or the like, or a mixed solvent thereof) in the presence or absence of an appropriate acid (hydrochloric acid, sulfuric acid or the like) and/or an additive (cupric chloride or the like) at −78° C. to 200° C. The following halogenosulfonylation may be carried out in reference to the following (MM).

(O) A compound having substituted or unsubstituted aminosulfonyl on $R^1$-$R^6$ among the objective compound [I] may be also prepared by reacting a compound wherein the corresponding site is halogenosulfonyl with a substituted or unsubstituted amine. The reaction may be preferably carried out in an appropriate solvent (methylene chloride, chloroform, THF, dioxane, water or the like) in the presence or absence of a base (pyridine, triethylamine, sodium hydroxide, sodium carbonate or the like) at −78° C. to 200° C.

(P) A compound having alkylthio, cycloalkylthio, heterocyclyl-thio on $R^1$-$R^6$ among the objective compound [I] may be also prepared by, for example, converting a compound wherein the corresponding site is methylsulfinyl into thiol in the same manner as described in a literature (Young R. N., et al., Tetrahedron Lett., 1984, 25(17), 1753), followed by reacting with an alkylating agent (haloalkyl, halocycloalkyl, haloheterocycle compound, alkyl mesylate, cycloalkyl mesylate, heterocyclyl mesylate, alkyl tosylate, cycloalkyl tosylate, heterocyclyl tosylate or the like) in the presence or absence of a base (sodium hydride, cesium carbonate, potassium carbonate, potassium t-butoxide, triethylamine, diazabicycloundecene or the like).

(Q) A compound having substituted or unsubstituted alkanoylamino on $R^1$-$R^6$ among the objective compound [I] may be also prepared by alkanoylating a compound wherein the corresponding site is amino. The alkanoylation may be carried out in a similar manner to the reaction of the above (C). Also, the alkanoylation may be carried out in a compound wherein the corresponding site is a secondary amine as well as a primary amine.

(R) A compound having substituted sulfonylamino such as alkylsulfonylamino, heteroarylsulfonylamino, heterocyclylsulfonylamino or the like on $R^1$-$R^6$ among the objective compound [I] may be also prepared by sulfonylating a compound wherein the corresponding site is amino. The sulfonylation may be carried out in an appropriate solvent (water, THF, methylene chloride, chloroform or the like) in the presence or absence of a base (triethylamine, diisopropylethylamine, pyridine or the like) at −78° C. to 200° C. Also, the sulfonylation may be carried out in a compound wherein the corresponding site is a secondary amine as well as a primary amine.

(S) A compound having a secondary alcohol on $R^1$-$R^6$ among the objective compound [I] may be prepared by using any conventional method for converting ketone into a secondary alcohol. For example, the reaction may be carried out by using a compound having the corresponding oxo in the similar manner to the reaction of the above (K).

(T) A compound having oxo on $R^1$-$R^6$ among the objective compound [I] may be prepared by using any conventional method of converting a secondary alcohol into ketone. For example, the reaction may be carried out by dimethylsulfoxide oxidation with an activating agent such as oxalyl chloride in an appropriate solvent (dimethylsulfoxide, chloroform, methylene chloride or the like) (Swern oxidation), or by using an oxidizing agent (activated manganese dioxide, sulfur trioxide-pyridine complex, 1-hydroxy-1,2-benziodoxol-3(1H)-on-1-oxide, 1,1,1-triacetoxy-1,1-dihydro-1,2-benziodoxol-3(1H)-one, pyridinium chlorochromate, pyridinium dichromate or the like) in the presence or absence of a base (triethylamine or the like).

(U) A compound having a secondary alcohol on $R^1$-$R^6$ among the objective compound [I] may be prepared by using any conventional method of converting a compound having formyl into a secondary alcohol. For example, the reaction may be preferably carried out by using the corresponding formyl and a metal reagent (alkylmagnesium halide, alkyllithium, dialkylzinc or the like) in an appropriate solvent (THF, toluene, diethyl ether or the like) at −78° C. to 100° C.

(V) A compound having hydroxyamidino on $R^1$-$R^6$ among the objective compound [I] may be prepared by using any conventional method of converting cyano group into hydroxyamidino group. For example, the reaction may be preferably carried out by reacting a compound having the corresponding cyano with hydroxylamine (or a salt with an appropriate acid thereof) in the presence or absence of a base (sodium carbonate, potassium carbonate, sodium hydroxide, potassium hydroxide, potassium t-butoxide, triethylamine, pyridine or the like) in an appropriate solvent (water, methanol, ethanol or the like, or a mixed solvent thereof) at 0° C. to 100° C.

(W) A compound having unsubstituted carbamoyl on $R^1$-$R^6$ among the objective compound [I] may be prepared by using any conventional method of converting cyano group into unsubstituted carbamoyl group. For example, the reaction may be preferably carried out by treating a compound having the corresponding cyano with a base (sodium hydroxide, potassium hydroxide, potassium t-butoxide or the like) in an appropriate solvent (water, methanol, ethanol, isopropanol or the like, or a mixed solvent thereof) at −20° C. to 100° C.

(X) A compound having a tertiary alcohol on $R^1$-$R^6$ among the objective compound [I] may be prepared by, for example, reacting a compound having the corresponding oxo under a condition of the above (U).

(Y) A preparation of a compound having an optically-active secondary alcohol on $R^1$-$R^6$ among the objective compound [I] may be carried out by using any conventional method of resolution of a secondary alcohol compound in enzymatic transesterification. For example, the preparation may be preferably carried out by treating the corresponding racemic secondary alcohol with an acyl donor (vinyl acetate or the like) in the presence of enzyme (lipase PS or the like) in an appropriate solvent (t-butylmethyl ether, hexane, diisopropyl ether, THF, diethyl ether, water or the like) at −78° C. to 100° C.

(Z) A preparation of a compound having alkyl on $R^1$-$R^6$ among the objective compound [I] may be carried out by using so-called catalytic hydrogenation. For example, the compound may be preferably prepared by treating a compound having the corresponding alkenyl with a metal catalyst (palladium carbon, platinum dioxide or the like) under hydrogen in an appropriate solvent (methanol, ethanol, DMF, THF, acetic acid or the like, or a mixed solvent thereof) at 0° C. to 200° C.

(AA) A preparation of a compound having 1,2-diol on $R^1$-$R^6$ among the objective compound [I] may be preferably carried out by, for example, treating a compound having the corresponding alkenyl with an oxidizing agent (osmium tetroxide, ruthenium tetroxide, sodium periodate or the like) in an appropriate solvent (water, acetone, THF, acetonitrile, ethyl acetate or the like, or a mixed solvent thereof) at 0° C. to 100° C.

(BB) A preparation of a compound having halogen atom on $R^1$-$R^6$ among the objective compound [I] may be carried out by using any conventional method of halogenation of alcohol. For example, the preparation may be preferably carried out by treating the corresponding alcohol with carbon tetrabromide in the presence of triphenylphosphine in an appropriate solvent (methylene chloride, chloroform or the like) at 0° C. to 100° C.

(CC) A preparation of a compound having unsubstituted and substituted alkylthio, heteroarylthio or arylthio on $R^1$, $R^2$, $R^5$ or $R^6$ among the objective compound [I] may be carried out by using any conventional method of coupling thiol with halogenated aryl, halogenated heteroaryl, aryl triflate or heteroaryl triflate. For example, the preparation may be preferably carried out by treating a compound having the corresponding halogen atom or triflate with thiol (hydroxyalkylthiol, dialkylaminoalkylthiol, or the like) in the presence of a metal catalyst (tetrakis(triphenylphosphine)palladium or the like) in an appropriate solvent (dioxane, toluene, THF, 1,2-dimethoxyethane or the like, or a mixed solvent thereof) in the presence or absence of a base (triethylamine, diisopropylamine or the like) at 0° C. to 200° C.

(DD) A preparation of a compound having mono-substituted or di-substituted alkylamino on $R^1$-$R^6$ among the objective compound [I] may be preferably carried out by, for example, treating a compound having the corresponding haloalkyl with mono-substituted or di-substituted alkylamine (dimethylamine, diethylamine, methylamine or the like) in an appropriate solvent (methanol, ethanol, dioxane, toluene, THF, 1,2-dimethoxyethane or the like) in the presence or absence of a base (triethylamine, diisopropylamine or the like) at 0° C. to 200° C. Also, a compound having dimethylamino may be preferably prepared by treating a compound having the corresponding haloalkyl with N-(trimethylsilyl)dimethylamine in an appropriate solvent (methanol, ethanol, dioxane, toluene, THF, 1,2-dimethoxyethane or the like) at 0° C. to 200° C.

(EE) A preparation of a compound having alkynyl on $R^1$, $R^2$, $R^5$ or $R^6$ among the objective compound [I] may be carried out by using any conventional method of so-called Sonogashira coupling reaction of halogenated aryl, halogenated heteroaryl, aryl triflate or heteroaryl triflate with a compound having alkyne. For example, the preparation may be preferably carried out by treating a compound having the corresponding halogen atom with alkyne (propargyl alcohol, N,N-dimethylpropargylamine or the like) in the presence of a metal catalyst (tetrakis(triphenylphosphine)palladium or the like) in an appropriate solvent (dioxane, toluene, THF, 1,2-dimethoxyethane or the like) in the presence or absence of a base (triethylamine, diisopropylamine or the like) and/or a copper salt (for example, cuprous iodide) at 0° C. to 200° C.

(FF) A preparation of a compound having tetrazolyl on $R^1$-$R^6$ among the objective compound [I] may be carried out by using any conventional method of converting cyano group into tetrazolyl group. For example, the preparation may be preferably carried out by treating a compound having the corresponding cyano with metal azide (sodium azide, tributyltin azide, trimethylsilyl azide) in an appropriate solvent (methanol, ethanol, DMF, dioxane, toluene, THF, 1,2- dimethoxyethane or the like) in the presence or absence of a base (triethylamine, diisopropylamine or the like) or a salt (triethylamine hydrochloride or the like) at 0° C. to 200° C.

(GG) A preparation of a compound having O-alkoxycarbonyl-hydroxyimine on $R^1$-$R^6$ among the objective compound [I] may be preferably carried out by treating a compound having the corresponding hydroxyimine with alkyl chlorocarbonate (ethyl chlorocarbonate or the like) in an appropriate solvent (DMF, dioxane, toluene, THF, 1,2-dimethoxyethane or the like) or as neat in the presence or absence of a base (pyridine, triethylamine or the like) at 0° C. to 200° C.

(HH) A preparation of a compound having aryl or heteroaryl on $R^1$, $R^2$, $R^5$ or $R^6$ among the objective compound [I] may be carried out by using any conventional method of so-called Stille coupling or Suzuki coupling reaction. For example, the preparation may be preferably carried out by treating a compound having the corresponding haloaryl with aryltrialkyltin, heteroaryltrialkyltin, aryldihydroxyborane, heteroaryl-dihydroxyborane, arylcatecholborane, heteroarylcatecholborane or the like in the presence of a metal catalyst (for example, dichlorobis-(triphenylphosphine)palladium, tetrakis(triphenylphosphine)palladium, tris(dibenzylideneacetone)dipalladium, dichloro[1,1'-bis(diphenyl-phosphino)ferrocene] palladium, palladium acetate or the like) in an appropriate solvent (dioxane, toluene, THF, 1,2-dimethoxyethane or the like, or a mixed solvent thereof) in the presence or absence of a base (triethylamine, diisopropylamine, sodium t-butoxide, sodium carbonate, cesium carbonate, potassium phosphate or the like) at 0° C. to 200° C.

(II) In the above each reaction, a protecting group may be optionally introduced or removed to give the desired compound [I] finally. A method for introduction and removal of the protecting group may be carried out according to the description of Protective Groups in Organic Synthesis Third Edition (Theodora W. Green and Peter G. Wuts).

(JJ) Alternatively, compound [I] may be also synthesized by optionally carrying out any of the above reaction of (A) to (II) in compound [II] to compound [XVI] in an appropriate stage in each process in the preparation thereof.

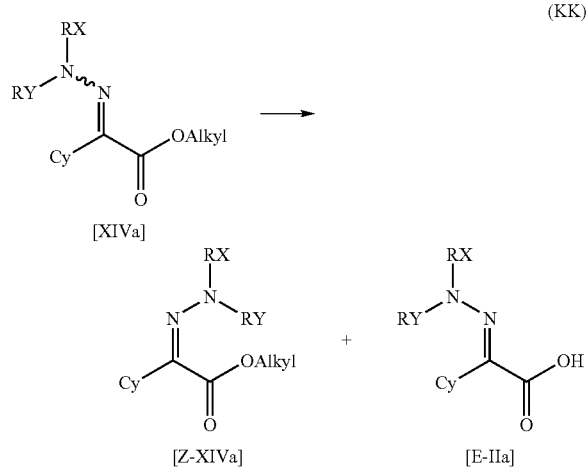

wherein Cy is an organic cyclic group (e.g., substituted or unsubstituted aryl, substituted or unsubstituted heteroaryl, substituted or unsubstituted cycloalkyl, or substituted or unsubstituted heterocycle), Alkyl is alkyl, each of $R^X$ and $R^Y$ is independently an organic group, or $R^X$ and $R^Y$ combine each other together with the adjacent nitrogen atom to form an organic cyclic group.

Compound [XIVa] which is a mixture of cis- (i.e., a compound wherein hydrazone moiety is in cis configuration to carboxyl or alkoxycarbonyl, as also the same in this section) and trans-isomers may be selectively hydrolyzed to give trans-isomer [E-IIa] by utilizing a property that a reaction rate of trans-isomer is faster than that of cis-isomer. A preferable hydrolysis is alkali hydrolysis. A preferable base in the alkali hydrolysis includes alkali metal hydroxide such as sodium hydroxide, potassium hydroxide, potassium carbonate, lithium hydroxide, etc., and alkaline earth metal hydroxide such as magnesium hydroxide, calcium hydroxide, and a preferable solvent used therein includes alcoholic solvent such as methanol, ethanol, or dioxane, THF, water, or a mixture thereof. A reaction temperature therein is −78° C. to 200° C., preferably −20° C. to 100° C., more preferably 0° C. to 25° C. A reaction time therein is for 10 minutes to 7 days, preferably for 1 to 48 hour(s), more preferably 1 to 24 hour(s), or it is preferably decided by monitoring in thin-layer chromatography, high-performance liquid chromatography, etc. Preferably, Cy is Ring A having $R^1$ and $R^2$. Preferably, $R^X$ and $R^Y$ are $R^3$ and $R^4$, respectively. [Z-XIVa] and [E-XIIa] may be successfully separated by liquid-liquid extraction, or purification on ion-exchange resin or column chromatography, etc.

Compound [II] may be also prepared in accordance with this manner.

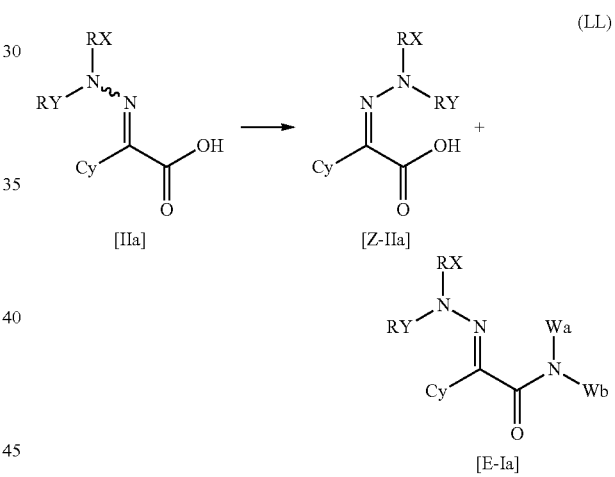

wherein Wa is hydrogen or an organic group (substituted or unsubstituted alkyl, etc.), Wb is hydrogen, substituted or unsubstituted alkyl, substituted or unsubstituted aryl, substituted or unsubstituted heteroaryl, substituted or unsubstituted cycloalkyl, or substituted or unsubstituted heterocycle, each of $R^X$ and $R^Y$ is independently an organic group, or $R^X$ and $R^Y$ combine each other together with the adjacent nitrogen atom to form an organic cyclic group, and the other symbols have the same meanings as defined above.

Compound [IIa] which is a mixture of cis- (i.e., a compound wherein hydrazone moiety is in cis configuration to carboxyl or substituted or unsubstituted carbamoyl, as also the same in this section) and trans-isomers may be selectively amidated to give trans-isomer [E-Ia] by utilizing a property that a reaction rate of trans-isomer is faster than that of cis-isomer. An amidation may be carried out in a conventional manner, preferably a manner described in (C). A reaction time therein is for 10 minutes to 7 days, preferably for 1 to 48 hour(s), more preferably 1 to 24 hour(s), or it is preferably decided by monitoring in thin-layer chromatography, high-performance liquid chromatography, etc. Preferably, Cy is Ring A having $R^1$ and $R^2$. Preferably, Wa is alkyl or hydrogen, particularly hydrogen. Preferably, Wb is Ring T having $R^5$ and $R^6$. Preferably, $Rx^X$ and $R^Y$ are $R^3$ and $R^4$, respectively. [Z-IIa] and [E-Ia] may be successfully separated by liquid-liquid extraction, or purification on ion-exchange resin or column chromatography, etc.

Compound [I] may be also prepared in accordance with this manner.

(MM) Aryl diazonium or heteroaryl diazonium salt may be converted into halogenosulfonyl aryl or halogenosulfonyl heteroaryl by reacting with a halogenosulfonylating agent (sulfur dioxide, sodium bisulfite, etc.) in the presence of an additive (copper chloride, etc.). A preferable halogenosulfonylating agent is a nitrite salt due to a facility of weighing technique. A preferable reaction solvent is selected from hydrochloric acid, hydrobromic acid or hydroiodic acid, and it may be optionally combined with acetic acid, sulfuric acid, water, THF, ethyl acetate or a mixture thereof. A reaction temperature therein is −78° C. to 200° C., preferably −20° C. to 100° C., more preferably −20° C. to 30° C. The reaction may be also carried out by adding a halogenosulfonylation agent and an additive to a reaction solution of aryl diazonium salt or heteroaryl diazonium salt prepared from arylamine or heteroarylamine or a salt thereof in accordance with the manner of (N). Aryl and heteroaryl in (MM) may optionally have 1 to 5 substituent(s).

EXPERIMENTAL EXAMPLES

Glucokinase Activation Effect

A glucokinase activity was examined by measuring the amount of NADPH obtained in generating 6-phosphogluconic acid from glucose-6-phosphate dehydrogenase wherein glucose-6-phosphoric acid is a coupled enzyme, not by directly measuring the generated glucose-6-phosphoric acid. The glucokinase enzyme used in the examination was human-liver type GST-GK expressed by *E. Coli*. The measurement of the activity was carried out by the following procedures. Specifically, 30 mM HEPES buffer (pH7.4) containing 30 mM $MgCl_2$, 30 mM KCl, 1 mM DTT, 5 mM NADP (Nacalai), 0.7 mU/mL G6PDH (Roche 737-232 grade II from yeast) and 0.17 μL/mL GST-GK was prepared as a reaction solution. An evaluating compound dissolved in DMSO was added to the reaction solution to give a final concentration of 0.01 to 100 μM (5% DMSO). Thereto was added glucose (final concentration of 5 mM) as a substrate and was added ATP (final concentration of 5 mM) to proceed the reaction. The reaction temperature is 30° C. and a generation of NADPH was monitored by changes of absorbance of 340 nm. An increase of absorbance for 10 minutes after starting reaction was measured and the blank-corrected value was used as a GK activity (mOD/min). $EC_{50}$ level was calculated by a GK activity level in an addition of the evaluating compound at each concentration.

| EXAMPLE Nos. | $EC_{50}$ (μM) |
|---|---|
| 1 | 0.07 |
| 2 | 0.36 |
| 24 | 0.03 |
| 27 | 0.22 |
| 42 | 0.11 |
| 64 | 0.12 |
| 125 | 0.46 |

The compound [I] of the present invention or a pharmaceutically acceptable salt thereof is useful for preventing or treating diseases involving glucokinase, for example, diabetes, particularly type 2 diabetes, or chronic complications associated with diabetes such as retinopathy, nephropathy, neuropathy, ischemic heart disease or arteriosclerosis as well as obesity because of its excellent glucokinase activation effect.

BEST MODE FOR CARRYING OUT THE INVENTION

The present invention is explained in more detail in the following EXAMPLES and REFERENCE EXAMPLES, but it is not limited to these explanations. In EXAMPLES, APCI is atmospheric pressure chemical ionization mass spectrum and ESI is electrospray ionization mass spectrum. Herein, THF is tetrahydrofuran, DMF is dimethyl formamide, and DMSO is dimethylsulfoxide, respectively. In EXAMPLES, Me is methyl, Et is ethyl, Ac is acetyl, and Boc is t-butoxycarbonyl.

EXAMPLES

Example 1

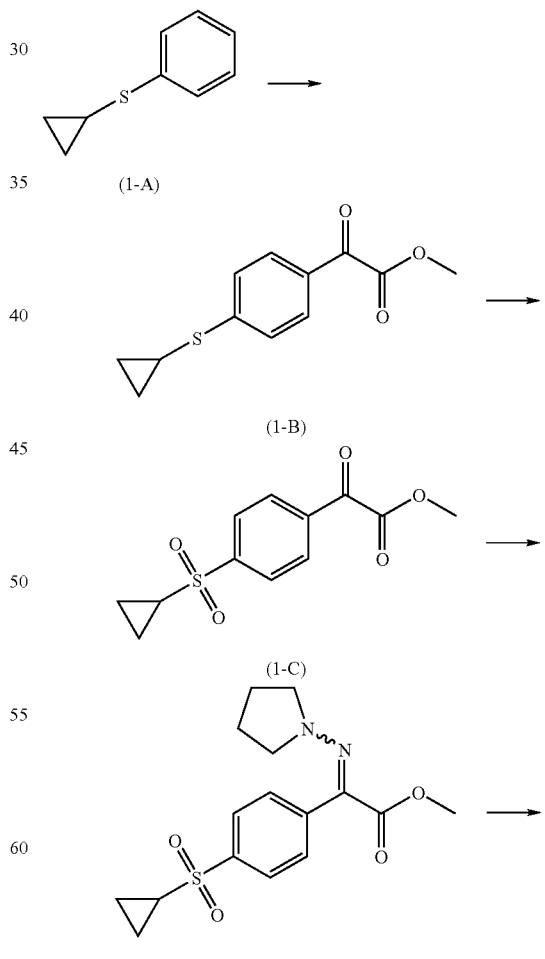

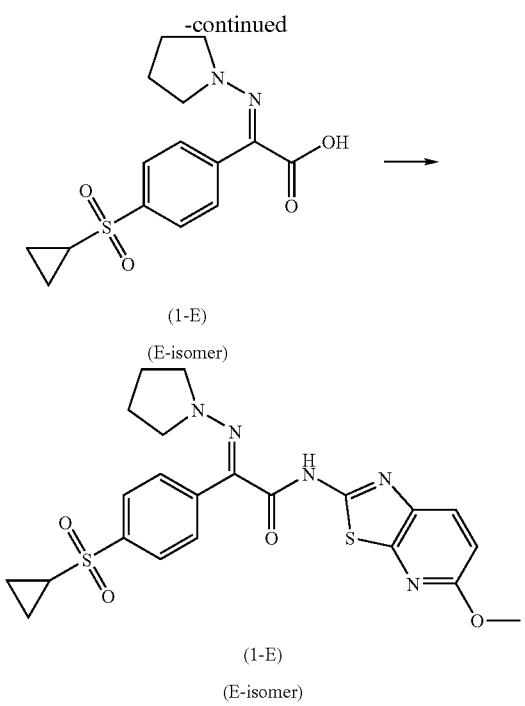

(1-E)
(E-isomer)

(1-E)
(E-isomer)

(1) To a solution of aluminum chloride (67.0 g, 503 mmol) in methylene chloride (380 ml) was added methyl chloroglyoxylate (48.9 g, 399 mmol) under ice-cooling, and the mixture was stirred for 30 minutes at the same temperature. Then, thereto was added a solution of cyclopropyl phenyl sulfide (compound I-A) (50 g, 333 mmol) in methylene chloride (60 ml), and then the ice-cooling bath was removed and the mixture was stirred at room temperature for 1.5 hours. The reaction solution was poured into ice, and then the methylene chloride layer was separated and concentrated in vacuo. The residue was dissolved in ethyl acetate and then washed sequentially with water, a saturated aqueous sodium bicarbonate solution and brine, followed by drying over sodium sulfate and concentrated in vacuo. The residue was crystallized from hexane to give compound (1-B) (69.5 g, yield 88%) as a pale yellow crystal.

MS (m/z) APCI: 237 [M+H]$^+$ (2) To a solution of the above compound (1-B) (57.0 g, 241 mmol) in methanol-THF (1:1) (1480 ml) was added dropwise an aqueous solution (513 ml) of Oxone™ (178 g, 289 mmol) under ice-cooling, and then the mixture was stirred at the same temperature for 1 hour, and after removing the ice bath, it was further stirred at room temperature for 12 hours. An insoluble material was filtered off, and then the filtrate was concentrated in vacuo. The residue was dissolved in ethyl acetate, washed sequentially with water and brine, dried over sodium sulfate and concentrated in vacuo. The resulting residue was recrystallized from diethyl ether to give compound (1-C) (44.3 g, yield 69%) as a pale yellow crystal.

MS (m/z) APCI: 286 [M+H]$^+$ (3) A solution of the above compound (1-C) (16.7 g, 62.1 mmol), aminopyrrolidine hydrochloride (9.89 g, 80.7 mmol) and pyridine (8.37 ml, 99.3 mmol) in methanol (160 ml) was stirred at 65° C. for 6 hours, and then at room temperature overnight. The reaction mixture was concentrated in vacuo, and to the residue were added ethyl acetate, followed by saturated sodium bicarbonate water. The organic layer was separated, and then dried over sodium sulfate and purified by NH-silica gel column chromatography using ethyl acetate as an elution solvent. The eluent was concentrated in vacuo, and to the residue was added toluene, and the residual pyridine was removed off by azeotrope in vacuo. The residue was purified by silica gel chromatography (50 to 67% ethyl acetate-hexane) to give compound (1-D) (E:Z=5:1, 10.4 g, yield 50%) as a pale yellow solid.

(4) To a solution of the above compound (1-D) (16.7 g, 49.8 mmol) in methanol (250 ml) was added 2N aqueous sodium hydroxide (99.5 ml, 199 mmol) under ice-cooling, and the mixture was stirred at the same temperature for 1 hour and further stirred at room temperature for 26 hours. The reaction solution was concentrated in vacuo, and to the residue were added diethyl ether (700 ml) and water (300 ml). The aqueous layer was separated, and then the organic layer was further extracted with water (300 ml). To the combined aqueous layer was carefully added 2N hydrochloric acid (99.5 ml), and the mixture was extracted with chloroform 3 times. To the aqueous layer was further added 2N hydrochloric acid (20 ml), and the mixture was extracted with chloroform 2 times. The combined extract was washed with saturated saline, and then dried over sodium sulfate and concentrated in vacuo. The resulting crude crystal was triturated in THF-diethyl ether and filtered to give compound (1-E) (E-isomer, 14.2 g, yield 87%) as a colorless crystal.

MS (m/z) ESI: 321 [M−H]$^−$ (5) To a solution of the above compound (1-E) (42 mg, 0.13 mmol), 5-methoxy[1,3]thiazole[5,4-b]pyridin-2-amine (72 mg, 0.40 mmol) and 4-(N,N-dimethylamino)pyridine (37 mg, 0.27 mmol) in chloroform (2 ml) was added N-ethyl-N'-(3-dimethylaminopropyl)carbodiimide hydrochloride (28.6 g, 184 mmol) in chloroform (0.54 ml) at room temperature, and the mixture was stirred at the same temperature overnight. To the reaction solution was added saturated aqueous sodium bicarbonate, and the mixture was vigorously stirred for 10 minutes. The organic layer was separated, and then concentrated in vacuo. The residue was triturated in methanol-THF-DMSO-diethyl ether, filtered and washed with diethyl ether to give compound (1-F) (41 mg, yield 65%) as a colorless solid.

MS (m/z) APCI: 486 [M+H]$^+$

Example 2

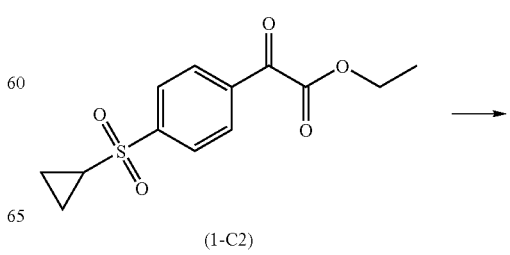

(1-C2)

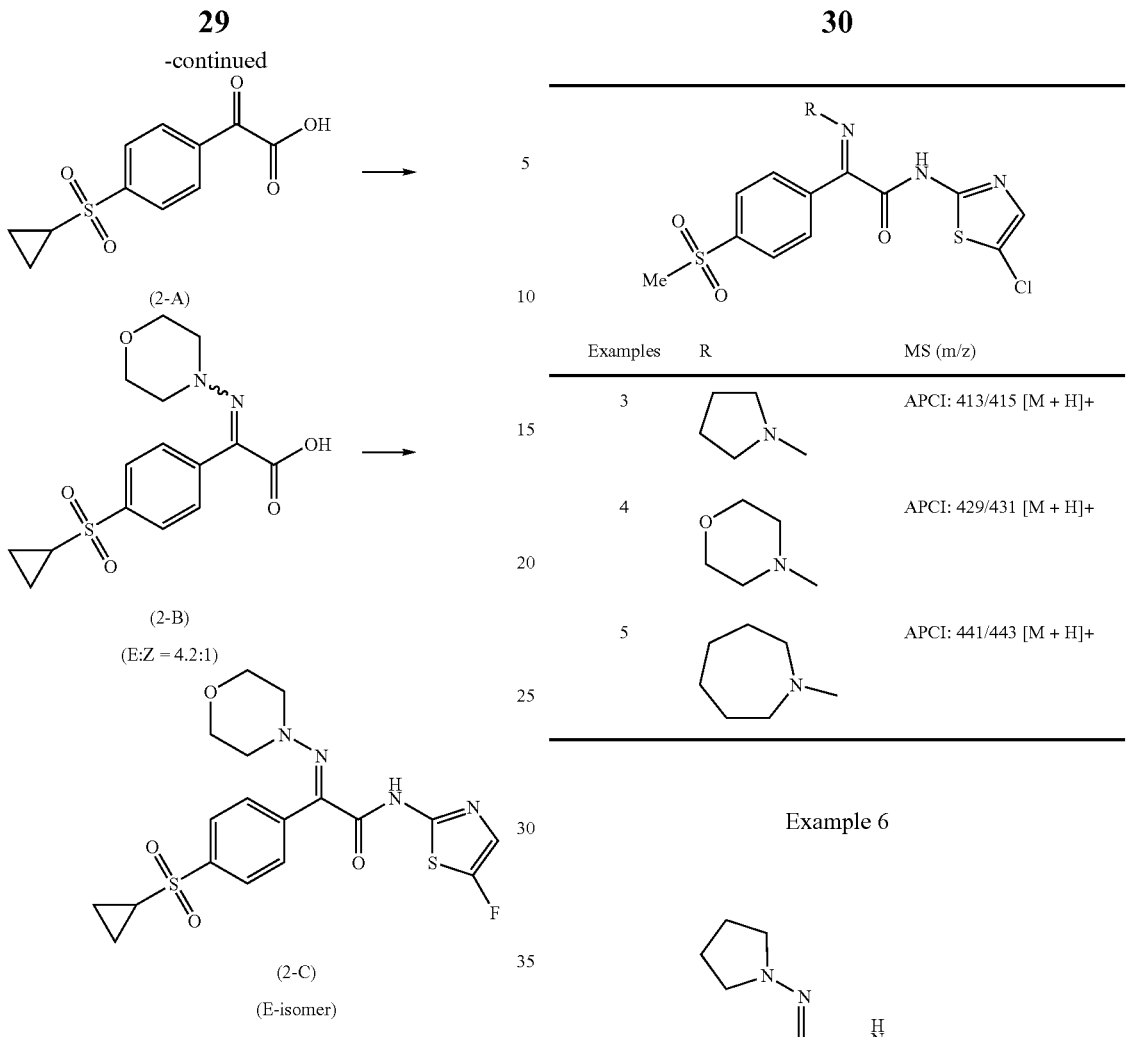

(1) A solution of compound (1-C2) (10.0 g, 35.4 mmol) in 16% hydrochloric acid (100 ml) was heated to reflux for 24 hours. After cooling, the reaction solution was concentrated in vacuo, and the residue was triturated in toluene to give compound (2-A) (9.0 g, quantitative) as a colorless solid.

MS (m/z) ESI: 253 [M−H]⁻

(2) A solution of compound (2-A) (2.54 g, 9.99 mmol) and 4-aminomorpholine (1.02 g, 9.99 mmol) in methylene chloride was stirred for 3 hours at room temperature. The reaction solution was concentrated in vacuo, and then the residue was crystallized with methylene chloride-diethyl ether to give compound (2-B) (E:Z=4.2:1, 2.32 g, yield 69%) as a colorless crystal.

MS (m/z) ESI: 337 [M−H]⁻

(3) To a solution of compound (2-B) (169 mg, 0.50 mmol), 2-amino-5-fluorothiazole hydrochloride (231 mg, 1.50 mmol) and 4-(N,N-dimethylamino)pyridine (91 mg, 0.75 mmol) in methylene chloride was added N-ethyl-N'-(3-dimethylaminopropyl)carbodiimide (0.136 ml, 0.75 mmol) at room temperature, and the mixture was stirred at the same temperature for 24 hours. The reaction solution was purified by silica gel column chromatography (2 to 10% methanol containing chloroform) to give compound (2-C) (E-isomer, 65 mg, yield 30%) as a colorless solid.

MS (m/z) APCI: 439 [M+H]⁺

The following compounds were prepared by treatment in the similar manner to the synthetic procedures described herein and EXAMPLES.

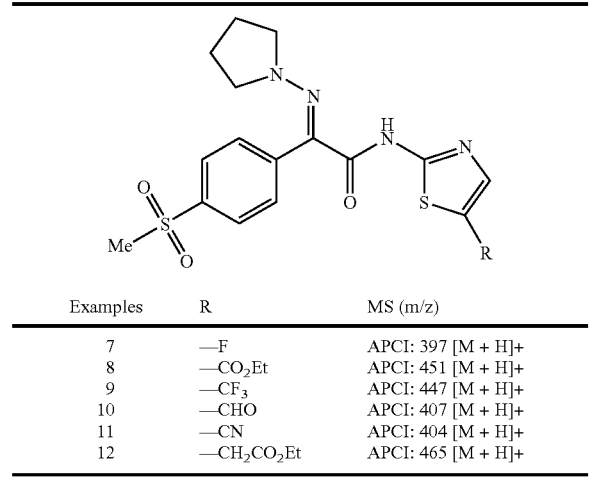

| Examples | R | MS (m/z) |
|---|---|---|
| 3 | pyrrolidinyl | APCI: 413/415 [M + H]+ |
| 4 | morpholinyl | APCI: 429/431 [M + H]+ |
| 5 | azepanyl | APCI: 441/443 [M + H]+ |

Example 6

MS (m/z) APCI: 413/415 [M+H]⁺

| Examples | R | MS (m/z) |
|---|---|---|
| 7 | —F | APCI: 397 [M + H]+ |
| 8 | —CO₂Et | APCI: 451 [M + H]+ |
| 9 | —CF₃ | APCI: 447 [M + H]+ |
| 10 | —CHO | APCI: 407 [M + H]+ |
| 11 | —CN | APCI: 404 [M + H]+ |
| 12 | —CH₂CO₂Et | APCI: 465 [M + H]+ |

Example 13

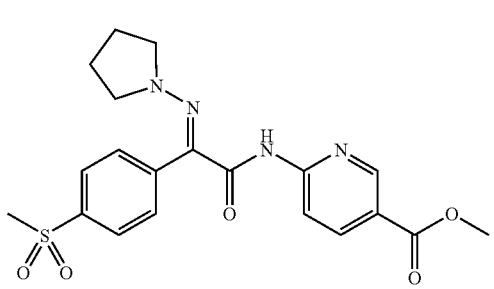

MS (m/z) APCI: 431 [M+H]+

Example 14

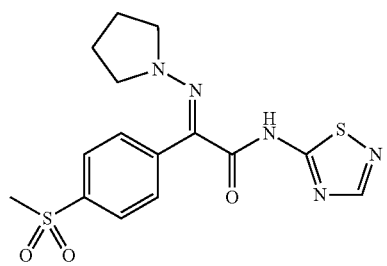

MS (m/z) APCI: 380 [M+H]+

---

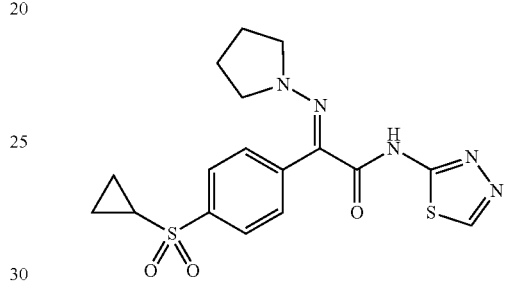

| Examples | R | MS (m/z) |
|---|---|---|
| 15 | 2-thiazolyl | APCI: 405 [M + H]+ |
| 16 | 5-fluoro-2-thiazolyl | APCI: 423 [M + H]+ |
| 17 | 2-pyridyl | APCI: 399 [M + H]+ |
| 18 | 5-formyl-2-thiazolyl | APCI: 433 [M + H]+ |
| 19 | 5-chloro-2-thiazolyl | ESI: 439/441 [M + H]+ |
| 20 | 4-pyrimidyl | APCI: 400 [M + H]+ |
| 21 | 5-fluoro-2-pyridyl | APCI: 417 [M + H]+ |
| 22 | 4-methyl-4-thiazolyl | APCI: 419 [M + H]+ |
| 23 | 5-methyl-2-thiazolyl | APCI: 419 [M + H]+ |
| 24 | 5-bromo-2-thiazolyl | APCI: 483/485 [M + H]+ |
| 25 | 3-isoxazolyl | APCI: 483/485 [M + H]+ |
| 26 | 2-pyrazyl | APCI: 400 [M + H]+ |

Example 27

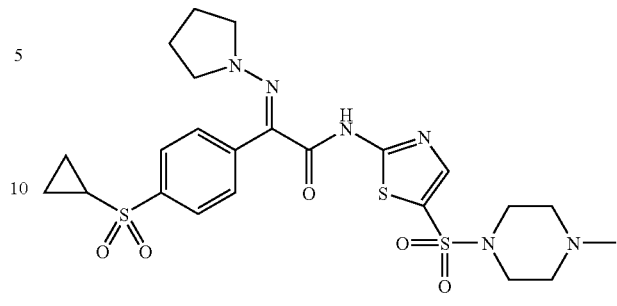

MS (m/z) APCI: 567 [M+H]+

Example 28

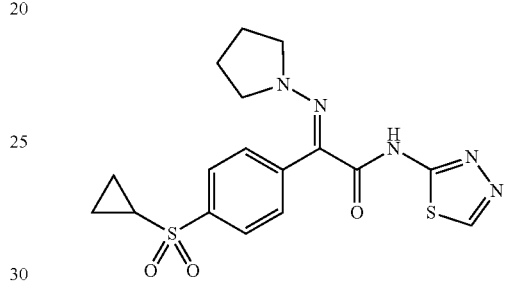

MS (m/z) ESI: 406 [M+H]+

Example 29

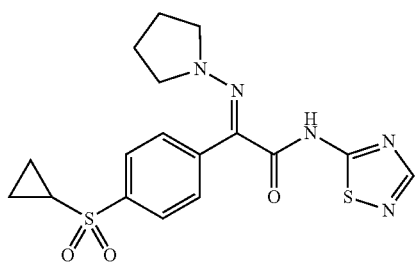

MS (m/z) APCI: 406 [M+H]+

Example 30

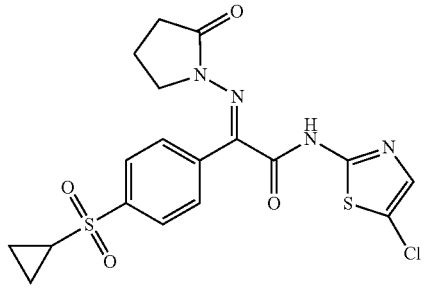

MS (m/z) APCI: 453/455 [M+H]+

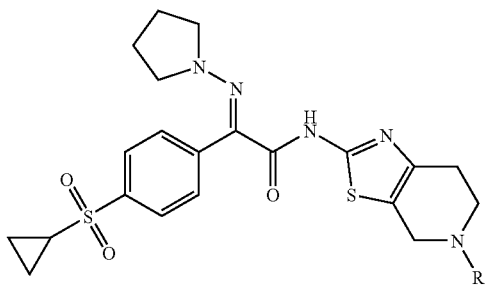

| Examples | R | MS (m/z) |
|---|---|---|
| 31 | methyl | APCI: 474 [M + H]+ |
| 32 | acetyl | APCI: 502 [M + H]+ |
| 33 | ethoxycarbonyl | APCI: 532 [M + H]+ |
| 34 | benzyl | APCI: 550 [M + H]+ |
| 35 | t-butoxycarbonyl | APCI: 560 [M + H]+ |

Example 36

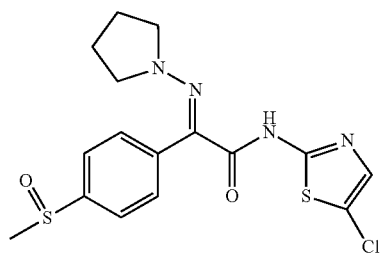

MS (m/z) APCI: 397/399 [M+H]$^{30}$

Example 37

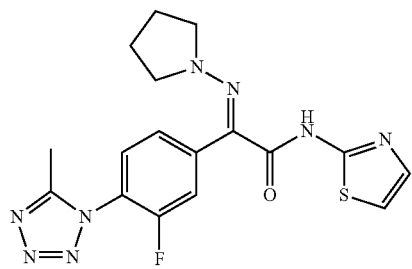

MS (m/z) APCI: 401 [M+H]$^+$

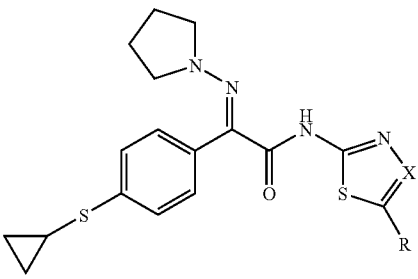

| Examples | R | X | MS (m/z) |
|---|---|---|---|
| 38 | —F | CH | APCI: 391 [M + H]+ |
| 39 | —H | CH | APCI: 373 [M + H]+ |
| 40 | —Cl | CH | APCI: 407/409 [M + H]+ |
| 41 | —CF$_3$ | N | APCI: 442 [M + H]+ |

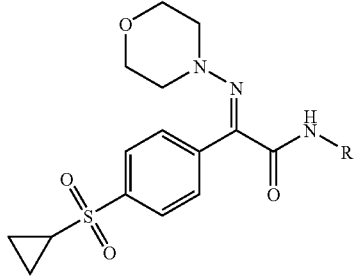

| Examples | R | MS (m/z) |
|---|---|---|
| 42 | 5-chloro-2-thiazolyl | APCI: 455/457 [M + H]+ |
| 43 | 5-trifluoromethyl-2-thiazolyl | APCI: 489 [M + H]+ |
| 44 | 4-methyl-2-thiazolyl | APCI: 435 [M + H]+ |
| 45 | 2-thiazolyl | APCI: 421 [M + H]+ |
| 46 | 5-methyl-2-thiazolyl | APCI: 435 [M + H]+ |
| 47 | 5-ethoxycarbonyl-2-thiazolyl | APCI: 493 [M + H]+ |
| 48 | 5-formyl-2-thiazolyl | APCI: 449 [M + H]+ |

Example 49

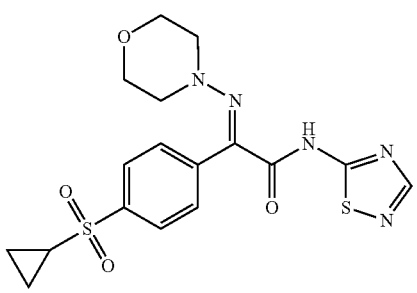

MS (m/z) APCI: 422 [M+H]$^+$

| Examples | R | MS (m/z) |
|---|---|---|
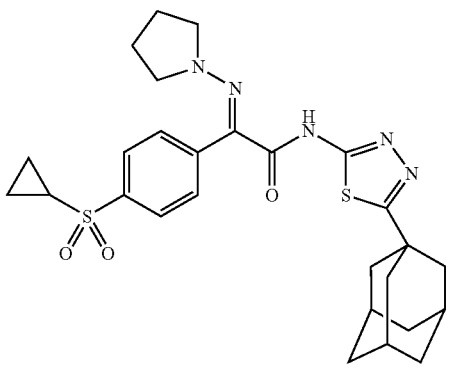
| 50 | —CF₃ | APCI: 490 [M + H]+ |
| 51 | —CO₂Et | APCI: 494 [M + H]+ |
| 52 | —SMe | APCI: 468 [M + H]+ |
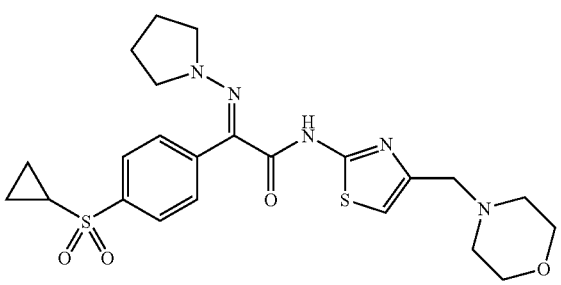
| 53 | —CF₃ | APCI: 474 [M + H]+ |
| 54 | —Me | APCI: 420 [M + H]+ |
| 55 | —SMe | APCI: 452 [M + H]+ |
| 56 | —CO₂Et | APCI: 478 [M + H]+ |
| 57 | —CMe₃ | ESI: 462 [M + H]+ |
Example 58
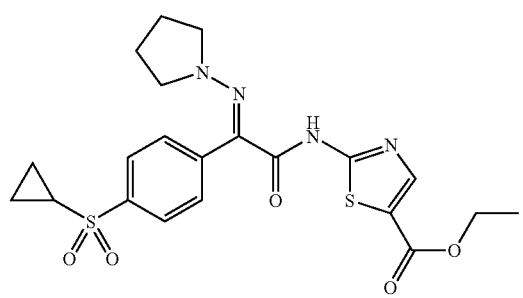
MS (m/z) APCI: 477 [M+H]⁺
Example 59
(structure shown)
MS (m/z) ESI: 540 [M+H]⁺
Example 60
(structure shown)
MS (m/z) ESI: 504 [M+H]⁺
Example 61
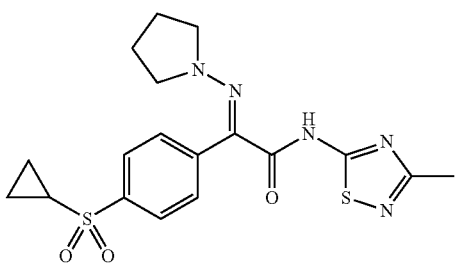
MS (m/z) ESI: 420 [M+H]⁺

Example 62
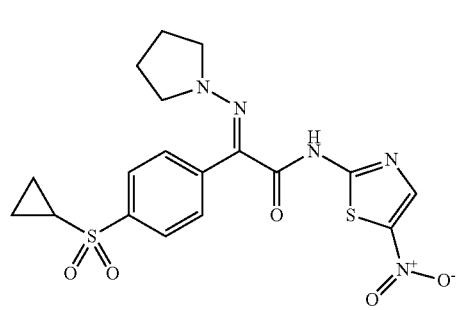
MS (m/z) ESI: 450 [M+H]+
Example 63
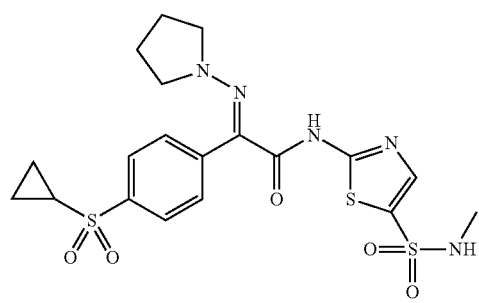
MS (m/z) ESI: 498 [M+H]+
Example 64
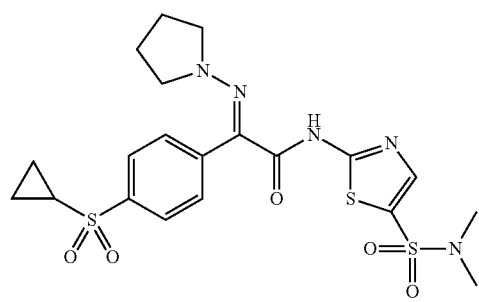
MS (m/z) ESI: 512 [M+H]+
Example 65
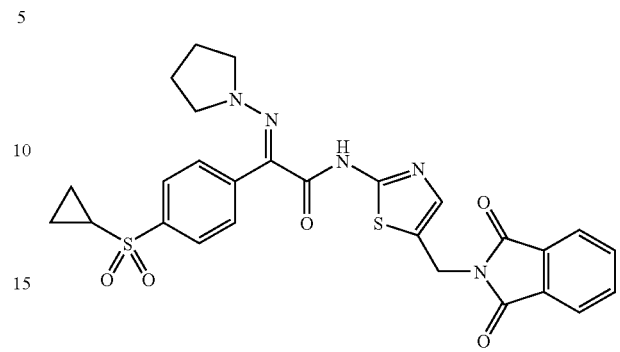
MS (m/z) APCI: 564 [M+H]+
Example 66
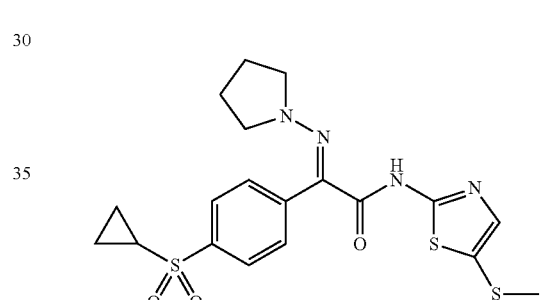
MS (m/z) APCI: 451 [M+H]+
Example 67
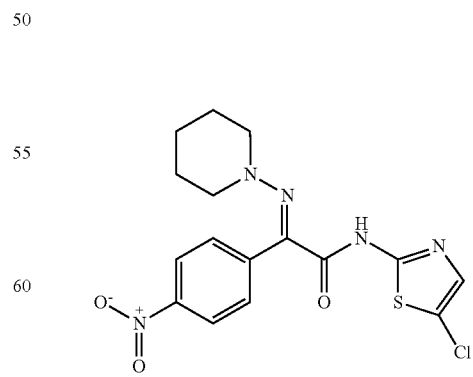
MS (m/z) APCI: 394/396 [M+H]+

Example 68

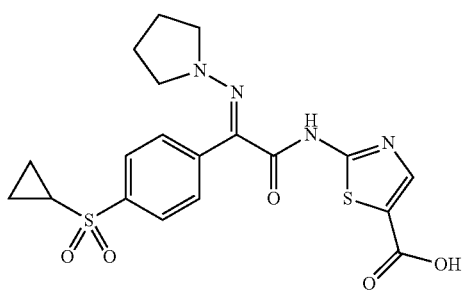

To a solution of the compound of EXAMPLE 58 (1.90 g, 3.99 mmol) in ethanol (20 ml) was added 1N aqueous sodium hydroxide (5 ml), and the mixture was stirred at room temperature for 24 hours. The reaction mixture was acidified by 2N hydrochloric acid (10 ml), and the precipitate is filtered to give the above compound (1.73 g, yield 97%) as a colorless solid.

MS (m/z) APCI: 449 [M+H]$^+$

Example 69

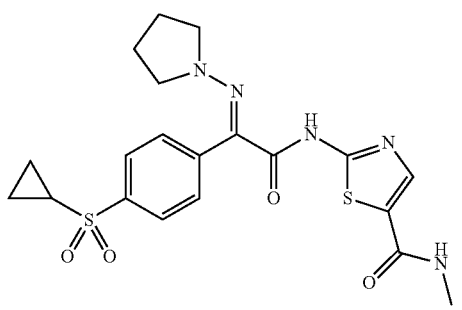

To a solution of the compound of EXAMPLE 68 (100 mg, 0.223 mmol) in THF (5 ml) were sequentially added N-methylmorpholine (37.0 µl, 0.337 mmol) and isobutyl chloroformate (43.5 µl, 0.337 mmol) at 0° C., and the mixture was stirred at the same temperature for 30 minutes. Additionally, to the mixture was added a solution of 2N dimethylamine in THF (335 µl, 0.670 mmol), and the mixture was stirred at the same temperature for 1 hour and stirred at room temperature for 40 hours. To the reaction mixture was added water (2 ml), and the mixture was eluted with chloroform as an elution solvent and filtered through Chem Elut (VARIAN, Inc.). The combined eluent was concentrated in vacuo, and the residue was purified by silica gel chromatography (3 to 10% methanol-chloroform) to give the above compound (46 mg, yield 45%) as a pale yellow solid.

MS (m/z) APCI: 462 [M+H]$^+$

Example 70

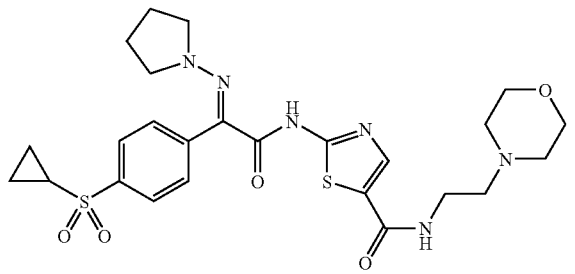

To a solution of the compound of EXAMPLE 68 (100 mg, 0.223 mmol), 2-(4-morpholinyl)ethylamine (44 µl, 0.335 mmol) and 1-hydroxybenzotriazole (52 mg, 0.391 mmol) in methylene chloride (5 ml) was added N-ethyl-N'-(3-dimethylaminopropyl)carbodiimide (59 µl, 0.34 mmol) at 0° C., and the mixture was stirred at the same temperature for 10 minutes and further stirred at room temperature for 3 hours. To the reaction mixture was added water (500 µl), and the mixture was eluted with ethyl acetate (30 ml) as an elution solvent and filtered through Chem Elut (VARIAN, Inc.) and Bond Elut JR-NH$_2$ (VARIAN, Inc.). The combined eluent was concentrated in vacuo, and the residue was purified by silica gel chromatography (3 to 10% methanol-chloroform) to give the above compound (89 mg, yield 72%) as a colorless solid.

MS (m/z) APCI: 561 [M+H]$^+$

The following compounds were prepared by treatment in the similar manner to the synthetic procedures described herein and EXAMPLES.

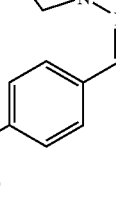

| Examples | R | MS (m/z) |
|---|---|---|
| 71 | methyl | APCI: 436 [M + H]+ |
| 72 | 2-methoxy-1-ethyl | APCI: 480 [M + H]+ |
| 73 | 3-pyridylmethyl | APCI: 513 [M + H]+ |
| 74 | 2-hydroxy-1-ethyl | APCI: 466 [M + H]+ |
| 75 | —H | APCI: 422 [M + H]+ |
| 76 | 2-pyridyl | APCI: 499 [M + H]+ |
| 77 | 1-hydroxy-2-methyl-2-propyl | APCI: 494 [M + H]+ |
| 78 | 2-dimethylamino-1-ethyl | APCI: 493 [M + H]+ |
| 79 | carbamoylmethyl | APCI: 479 [M + H]+ |

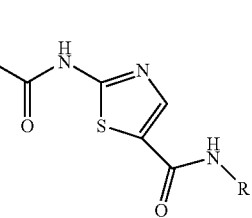

| Examples | R | MS (m/z) |
|---|---|---|
| 80 | —NH$_2$ | APCI: 448 [M + H]+ |
| 81 | —NHMe | APCI: 462 [M + H]+ |
| 82 | —NMe$_2$ | APCI: 476 [M + H]+ |
| 83 | piperazinyl-Ac | APCI: 559 [M + H]+ |
| 84 | N-methylpiperazinyl | APCI: 531 [M + H]+ |
| 85 | —NHCH$_2$CH$_2$OH | APCI: 492 [M + H]+ |
| 86 | —N(Me)CH$_2$CH$_2$NHMe | APCI: 519 [M + H]+ |

-continued

| Examples | R | MS (m/z) |
|---|---|---|
| 87 | ![morpholine-like 7-membered ring with N-Me and O] | APCI: 532 [M + H]+ |
| 88 | —NH-CH2-(5-methylisoxazol-3-yl) | APCI: 534 [M + H]+ |
| 89 | 4-methyl-2-oxopiperazin-1-yl | APCI: 531 [M + H]+ |
| 90 | 4-methyl-1,4-diazepan-1-yl | APCI: 545 [M + H]+ |
| 91 | 4-(dimethylamino)piperidin-1-yl | APCI: 559 [M + H]+ |
| 92 | —N(Me)CH₂CH₂NMe₂ | APCI: 533 [M + H]+ |
| 93 | —NHCH₂CN | APCI: 487 [M + H]+ |
| 94 | (S)-2-(methoxymethyl)-1-methylpyrrolidinyl | APCI: 546 [M + H]+ |
| 95 | —NHCH₂CH₂CH₂OH | APCI: 506 [M + H]+ |
| 96 | —NHCH₂CH₂CH₂NMe₂ | APCI: 533 [M + H]+ |
| 97 | —NHCH₂CH₂OMe | APCI: 506 [M + H]+ |
| 98 | —NHCH₂CH₂NMe₂ | APCI: 519 [M + H]+ |
| 99 | —NHC(Me)₂CH₂OH | APCI: 520 [M + H]+ |
| 100 | —NH-CH₂CH₂-(pyridin-2-yl) | APCI: 553 [M + H]+ |
| 101 | —NH-CH₂-(pyridin-2-yl) | APCI: 539 [M + H]+ |
| 102 | 1-methylpyrrolidin-N-yl | APCI: 502 [M + H]+ |
| 103 | —N(Me)CH₂CH₂OH | APCI: 506 [M + H]+ |
| 104 | —NHCH₂C(Me)₂OH | APCI: 520 [M + H]+ |
| 105 | —NHCH₂CH₂SMe | APCI: 522 [M + H]+ |
| 106 | —NH-(1H-tetrazol-5-yl) | ESI: 514 [M − H]− |

| Examples | R | MS (m/z) |
|---|---|---|
| 107 | —NHEt | APCI: 476 [M + H]+ |
| 108 | —N(Me)OMe | APCI: 492 [M + H]+ |
| 109 | —NHOMe | APCI: 478 [M + H]+ |
| 110 | —NMeEt | APCI: 490 [M + H]+ |
| 111 | N-methyl-N-(pyridin-2-yl) | APCI: 539 [M + H]+ |
| 112 | —NH-CH₂-(pyridin-2-yl) | APCI: 525 [M + H]+ |

Example 113

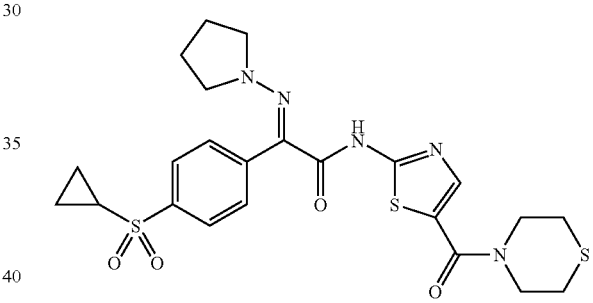

MS (m/z) APCI: 534 [M+H]+

Example 114

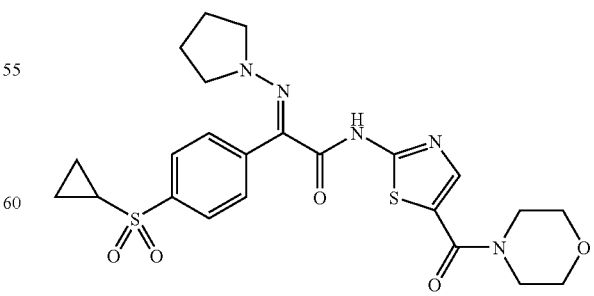

MS (m/z) APCI: 518 [M+H]+

Example 115

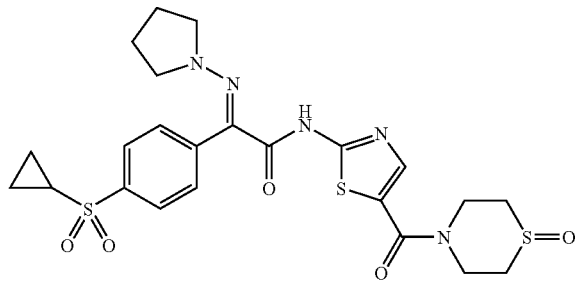

MS (m/z) APCI: 550 [M+H]⁺

Example 116

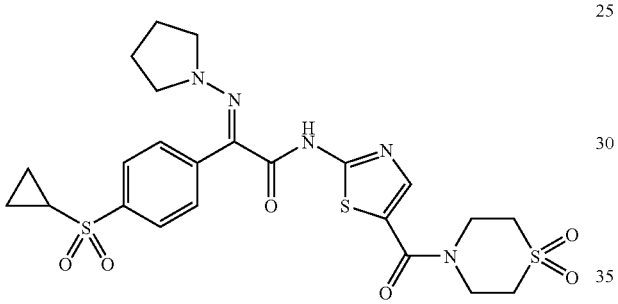

MS (m/z) APCI: 566 [M+H]⁺

Example 117

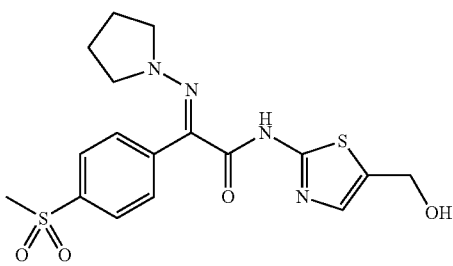

To a solution of the compound of EXAMPLE 10 (50 mg, 0.12 mmol) in methanol (1 ml) was added sodium borohydride (23 mg, 0.37 mmol) at 0° C., and the mixture was stirred at room temperature for 30 minutes. To the reaction mixture was added acetone (1 ml), and the mixture was concentrated in vacuo and the residue was purified by silica gel chromatography (2 to 10% methanol-chloroform) to give the above compound (46 mg, yield 92%) as a colorless solid.

MS (m/z) APCI: 409 [M+H]⁺

Example 118

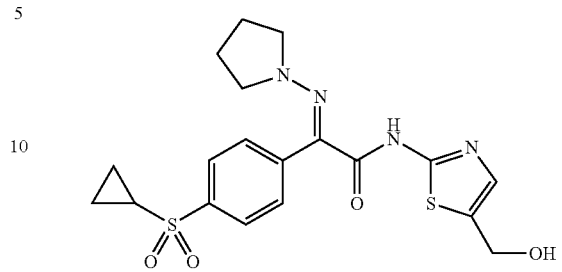

The corresponding starting compound was treated in the similar manner to EXAMPLE 117 to give the above compound as a colorless solid.

MS (m/z) APCI: 435 [M+H]⁺

Example 119

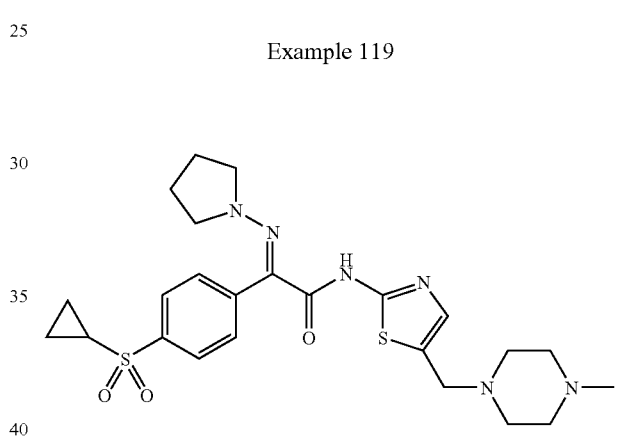

To a solution of the compound of EXAMPLE 18 (212 mg, 0.49 mmol) and 1-methylpiperazine (66 µl, 0.594 mmol) in methylene chloride (10 ml) was added sodium triacetoxyborohydride (156 mg, 0.736 mmol) at 0° C., and the mixture was stirred at the same temperature for 5 minutes and at room temperature for 4 hours. To the reaction mixture were further added 1-methylpiperazine (66 µl, 0.594 mmol), then sodium triacetoxyborohydride (156 mg, 0.736 mmol) at 0° C., and the mixture was stirred at room temperature for 18 hours. To the mixture was added saturated aqueous sodium bicarbonate (2 ml), and the mixture was vigorously stirred at room temperature for 10 minutes. The reaction mixture was filtered through Chem Elut (VARIAN, Inc.) and eluted with a mixed solvent of 20% methanol-chloroform (30 ml). The combined eluent was concentrated in vacuo, and the residue was purified by silica gel chromatography (9.1% methanol-chloroform) and washed with ethanol to give the above compound (141 mg, yield 56%) as a colorless solid.

MS (m/z) APCI: 517 [M+H]⁺

The following compounds were prepared by treatment in the similar manner to the synthetic procedures described herein and EXAMPLES.

| Examples | R | MS (m/z) |
|---|---|---|
| | 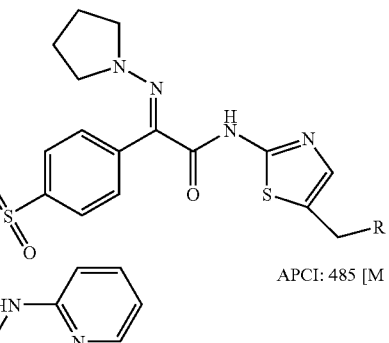 | |
| 120 | 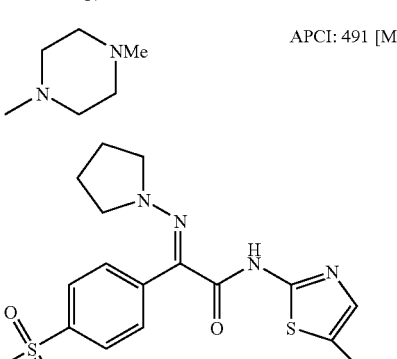 | APCI: 485 [M + H]+ |
| 121 | 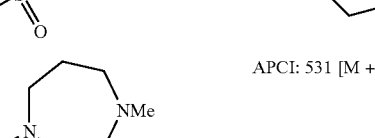 | APCI: 491 [M + H]+ |
| |  | |
| 122 | 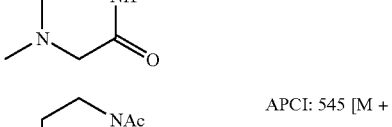 | APCI: 531 [M + H]+ |
| 123 | 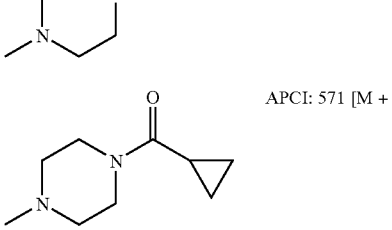 | APCI: 517 [M + H]+ |
| 124 |  | APCI: 545 [M + H]+ |
| 125 |  | APCI: 571 [M + H]+ |
| 126 | 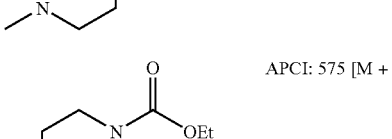 | APCI: 488 [M + H]+ |
| 127 | 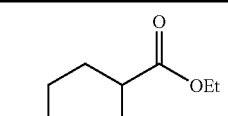 | APCI: 504 [M + H]+ |
| 128 | 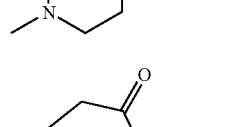 | APCI: 575 [M + H]+ |
-continued
| Examples | R | MS (m/z) |
|---|---|---|
| 129 | 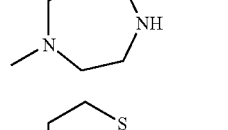 | APCI: 574 [M + H]+ |
| 130 | 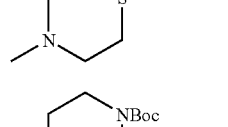 | APCI: 531 [M + H]+ |
| 131 | 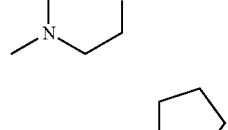 | APCI: 520 [M + H]+ |
| 132 | 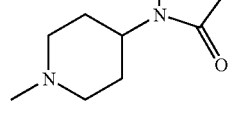 | APCI: 603 [M + H]+ |
| 133 | 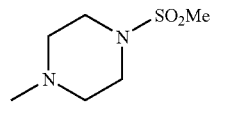 | APCI: 585 [M + H]+ |
| 134 | 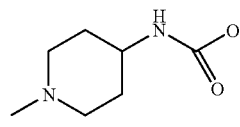 | APCI: 581 [M + H]+ |
| 135 | 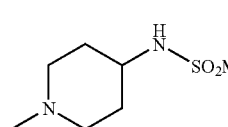 | APCI: 575 [M + H]+ |
| 136 | 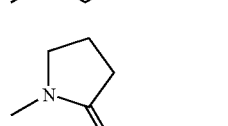 | APCI: 595 [M + H]+ |
| 137 | 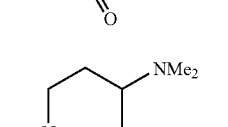 | APCI: 502 [M + H]+ |
| 138 | 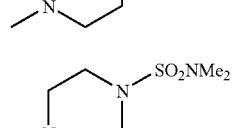 | APCI: 545 [M + H]+ |
| 139 | 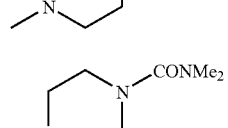 | APCI: 610 [M + H]+ |
| 140 | | APCI: 574 [M + H]+ |

-continued

| Examples | R | MS (m/z) |
|---|---|---|
| 141 | 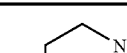 | APCI: 518 [M + H]+ |
| 142 | 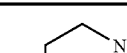 | APCI: 531 [M + H]+ |
| 143 | 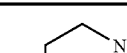 | APCI: 518 [M + H]+ |
| 144 | 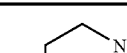 | APCI: 617 [M + H]+ |
| 145 | 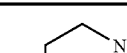 | APCI: 517 [M + H]+ |
| 146 | 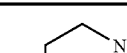 | APCI: 552 [M + H]+ |
| 147 | 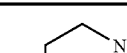 | APCI: 531 [M + H]+ |
| 148 | 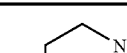 | APCI: 515 [M + H]+ |

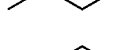

| Examples | R | MS (m/z) |
|---|---|---|
| 149 | 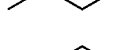 | APCI: 533 [M + H]+ |
| 150 | 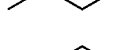 | APCI: 561 [M + H]+ |
| 151 | 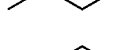 | APCI: 590 [M + H]+ |

-continued

| Examples | R | MS (m/z) |
|---|---|---|
| 152 | 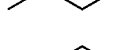 | APCI: 626 [M + H]+ |
| 153 | 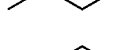 | APCI: 597 [M + H]+ |

Example 154

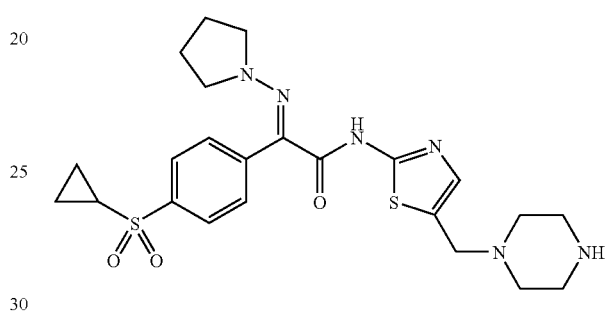

To a suspension of the compound of EXAMPLE 132 (313 mg, 0.52 mmol) in 1,4-dioxane (5 ml) was added a solution of 4N hydrogen chloride in dioxane (5 ml) at room temperature, and the mixture was vigorously stirred at the same temperature for 24 hours. To the reaction mixture was added water (10 ml) to dilute, and the mixture was washed with chloroform (20 ml). To the aqueous layer was added 10% aqueous sodium carbonate (10 ml) to be basified, and the mixture was extracted with chloroform (20 ml) 3 times. The combined chloroform layer was dried over sodium sulfate and evaporated in vacuo. The residue was triturated in a mixed solvent of ethyl acetate (10 ml)-diethyl ether (20 ml) and filtered to give the above compound (208 mg, yield 80%) as a pale yellow solid.

MS (m/z) APCI: 503 [M+H]$^+$

The following compounds were prepared by treatment in the similar manner to the synthetic procedures described herein and EXAMPLES.

Example 155

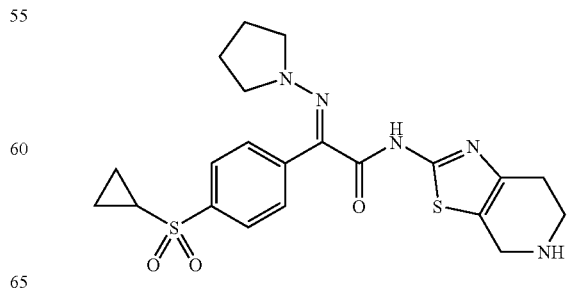

MS (m/z) APCI: 460 [M+H]$^+$

Example 156

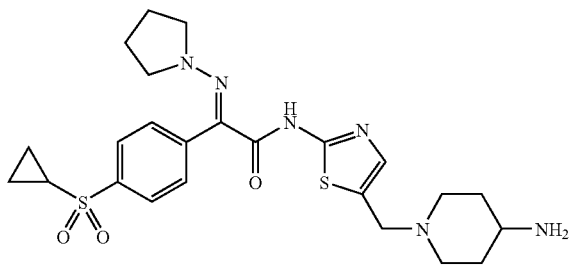

MS (m/z) APCI: 517 [M+H]+

Example 157

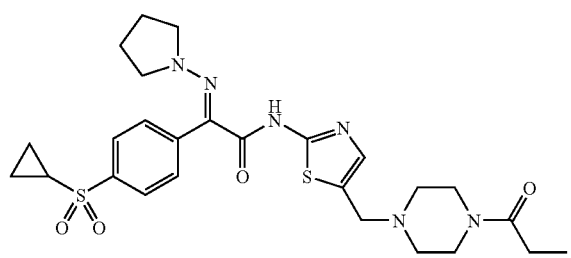

To a solution of 3 hydrochloride salt of the compound of EXAMPLE 154 (i.e., a crude product before neutralization) (60 mg, 0.098 mmol) and N,N-diisopropylethylamine (77 µl, 0.44 mmol) in chloroform (3 ml) was added propionyl chloride (12 µl, 0.13 mmol) under ice-cooling, and the mixture was stirred at the same temperature for 1 hour and at room temperature for 6 hours. To the reaction mixture was added saturated aqueous sodium bicarbonate (1 ml), and the mixture was stirred at room temperature for 1 hour, and dried over sodium sulfate, filtered through Bond Elut JR-NH$_2$ (VARIAN, Inc.) and eluted with ethyl acetate and a mixed solvent of 9% methanol-chloroform. The combined eluent was concentrated in vacuo, and the residue was purified by silica gel chromatography (0 to 10% methanol-chloroform) to give the above compound (48 mg, yield 88%) as a colorless solid.

MS (m/z) APCI: 559 [M+H]+

The following compounds were prepared by treatment in the similar manner to the synthetic procedures described herein and EXAMPLES.

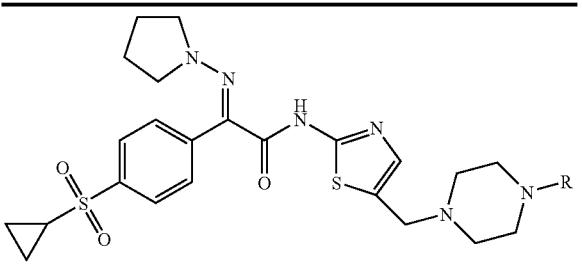

| Examples | R | MS (m/z) |
|---|---|---|
| 158 | pivaloyl | APCI: 587 [M + H]+ |
| 159 | 2-pyridinecarbonyl | APCI: 608 [M + H]+ |
| 160 | acetoxacetyl | APCI: 603 [M + H]+ |
| 161 | methoxyacetyl | APCI: 575 [M + H]+ |

Example 162

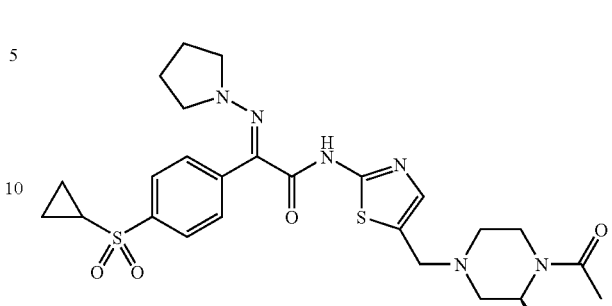

MS (m/z) APCI: 559 [M+H]+

Example 163

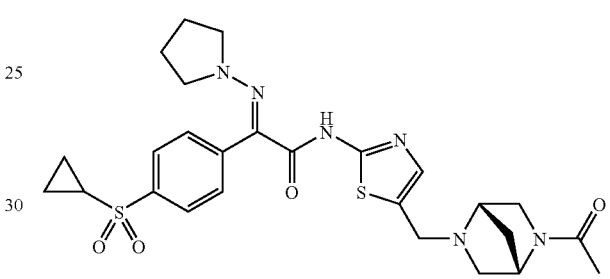

MS (m/z) APCI: 557 [M+H]+

Example 164

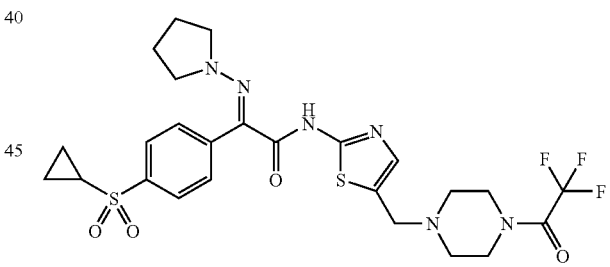

To a solution of 3 hydrochloride salt of the compound of EXAMPLE 154 (i.e., a crude product before neutralization) (60 mg, 0.098 mmol) and N,N-diisopropylethylamine (154 µl, 0.98 mmol) in chloroform (3 ml) was added trifluoroacetic anhydride (38 µl, 0.27 mmol) under ice-cooling, and the mixture was stirred at the same temperature for 1 hour and at room temperature overnight. To the reaction mixture was added saturated aqueous sodium bicarbonate (1 ml), and the mixture was stirred at room temperature for 1 hour, and then dried over sodium sulfate, filtered through Bond Elut JR-NH$_2$ (VARIAN, Inc.) and eluted with ethyl acetate and a mixed solvent of 9% methanol-chloroform. The combined eluent was concentrated in vacuo, and the residue was purified by silica gel chromatography (0 to 10% methanol-chloroform) to give the above compound (46 mg, yield 78%) as a pale yellow powder.

MS (m/z) APCI: 599 [M+H]+

Example 165

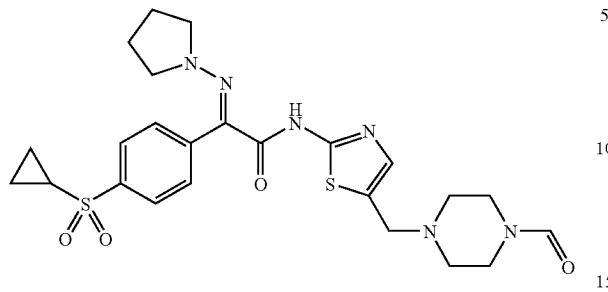

A solution of 3 hydrochloride salt of the compound of EXAMPLE 154 (i.e., a crude product before neutralization) (60 mg, 0.098 mmol) and N,N-diisopropylethylamine (77 µl, 0.44 mmol) in methyl formate (3 ml) was stirred at room temperature for 24 hours. The reaction solution was filtered through Bond Elut JR-NH$_2$ (VARIAN, Inc.) and eluted with ethyl acetate and a mixed solvent of 9.1% methanol-chloroform. The combined eluent was concentrated in vacuo, and the residue was purified by silica gel chromatography (0 to 10% methanol-chloroform) to give the above compound (39 mg, yield 75%) as a pale yellow amorphous.

MS (m/z) APCI: 531 [M+H]$^+$

Example 166

A solution of 3 hydrochloride salt of the compound of EXAMPLE 154 (60 mg, 0.098 mmol) and N,N-diisopropylethylamine (77 µl, 0.444 mmol) in acetonitrile (3 ml) was ice-cooled, and thereto was added p-nitrophenyl chloroformate, and then the mixture was stirred at room temperature overnight. To the reaction solution were added acetonitrile (1.5 ml) and 40% aqueous methylamine solution (4.5 ml), and the mixture was stirred at room temperature for 22 hours. To the reaction solution was added saturated saline, and the mixture was extracted with ethyl acetate 2 times. The extract was combined, and the organic layer was washed with saturated saline, dried over sodium sulfate, and then filtered through Bond Elut JR-NH$_2$ (VARIAN, Inc.) and eluted with ethyl acetate. The eluent was concentrated in vacuo, and the residue was purified by silica gel chromatography (0 to 10% methanol-chloroform) to give the above compound (48 mg, yield 87%) as a pale yellow powder.

MS (m/z) APCI: 560 [M+H]$^+$

Example 167

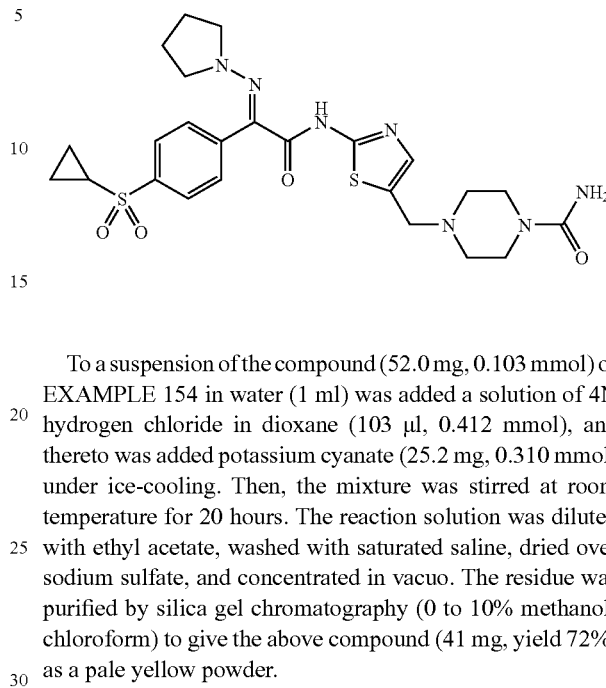

To a suspension of the compound (52.0 mg, 0.103 mmol) of EXAMPLE 154 in water (1 ml) was added a solution of 4N hydrogen chloride in dioxane (103 µl, 0.412 mmol), and thereto was added potassium cyanate (25.2 mg, 0.310 mmol) under ice-cooling. Then, the mixture was stirred at room temperature for 20 hours. The reaction solution was diluted with ethyl acetate, washed with saturated saline, dried over sodium sulfate, and concentrated in vacuo. The residue was purified by silica gel chromatography (0 to 10% methanol-chloroform) to give the above compound (41 mg, yield 72%) as a pale yellow powder.

MS (m/z) APCI: 546 [M+H]$^+$

Example 168

A mixture of the compound of EXAMPLE 65 (770 mg, 1.37 mmol), hydrazine monohydrate (343 mg, 6.85 mmol), ethanol (10 ml) and THF (10 ml) was stirred at room temperature for 24 hours. To the reaction solution was added saturated sodium bicarbonate water, and the mixture was extracted with chloroform 3 times. The extract was combined, dried over sodium sulfate, and then concentrated in vacuo. The residue was purified by NH-silica gel chromatography (75 to 100% chloroform-hexane), and the resulting crude crystal was washed with 50% ethyl acetate-hexane to give the above compound (510 mg, yield 86%) as a colorless powder.

MS (m/z) APCI: 434 [M+H]$^+$

Example 169

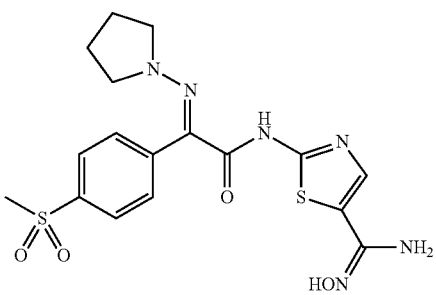

A suspension of the compound of EXAMPLE 11 (260 mg, 0.65 mmol) in methanol (10 ml) was ice-cooled, and thereto were added hydroxylammonium chloride (135 mg, 1.94 mmol) and a solution of 28% sodium methoxide in methanol (374 mg, 1.94 mmol). Then, the mixture was heated to reflux for 12 hours. The reaction mixture was cooled to room temperature, and thereto was added water. The precipitate was filtered and dried to give the above compound (218 mg, yield 77%) as a colorless powder of a single isomer.

MS (m/z) APCI: 437 [M+H]$^+$

Example 170

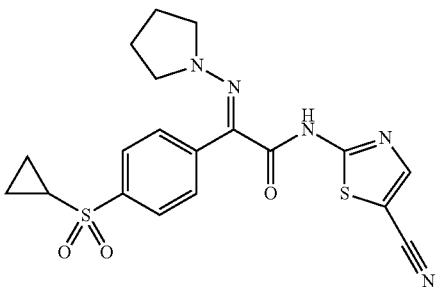

To a solution of the compound of EXAMPLE 18 (600 mg, 1.39 mmol) in pyridine (4 ml) was added hydroxylammonium chloride (106 mg, 1.53 mmol) at a time, and the mixture was stirred at room temperature for 30 minutes. The reaction solution was heated to 60° C., and thereto was added acetic anhydride (262 μg, 2.78 mmol). The mixture was stirred at the same temperature for 2 hours. The reaction solution was cooled to room temperature, concentrated in vacuo, and then to the residue was added water (10 ml). The mixture was extracted with dichloromethane (10 ml) 2 times. The extract was combined, dried over sodium sulfate, concentrated in vacuo, and then the residue was purified by silica gel chromatography (0 to 5% methanol-chloroform) to give a crude crystal (452 mg). The crude crystal (250 mg) was recrystallized with ethyl acetate-isopropyl ether (1:2) to give the above compound (189 mg, yield 58%) as a pale yellow powder.

MS (m/z) APCI: 430 [M+H]$^+$

Example 171

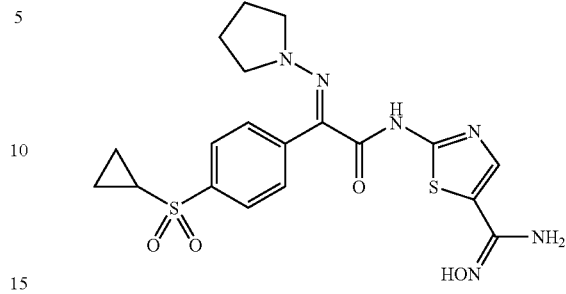

The compound of EXAMPLE 170 was treated in the similar manner to EXAMPLE 169 to give the above compound.

MS (m/z) APCI: 463 [M+H]$^+$

Example 172

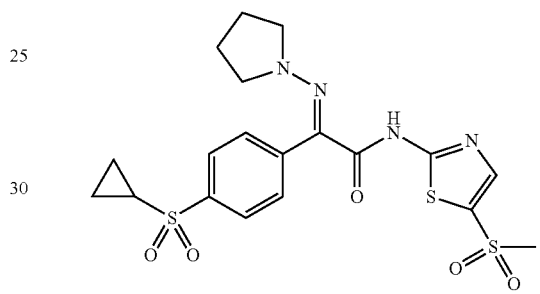

A solution of the compound of EXAMPLE 66 (110 mg, 0.237 mmol) in methylene chloride (3 ml) was ice-cooled, and thereto was added 65% m-chloroperbenzoic acid (101 mg, 0.378 mmol). The mixture was stirred at the same temperature for 40 minutes. To the reaction solution was added aqueous sodium sulfite solution, and the mixture was extracted with chloroform 3 times. The extract was combined, dried over sodium sulfate, and concentrated in vacuo. The residue was purified by silica gel chromatography (0 to 7% methanol-chloroform), and then crystallized with 50% ethyl acetate hexane to give the above compound (51 mg, yield 44%).

MS (m/z) APCI: 483 [M+H]$^+$

Example 173

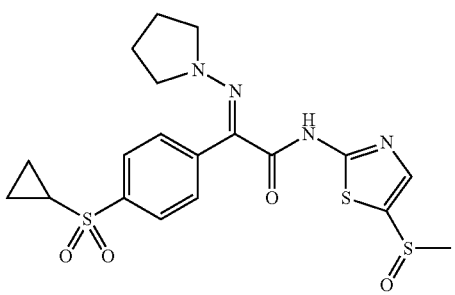

The compound obtained by silica gel chromatography in EXAMPLE 172 was crystallized with 50% ethyl acetate hexane to give the above compound (47 mg, yield 43%).

MS (m/z) APCI: 467 [M+H]$^+$

The following compounds were prepared by treatment in the similar manner to the synthetic procedures described herein and EXAMPLES.

| Examples | R | MS (m/z) |
|---|---|---|
| 174 | —CH₂CH₂N(Me)Boc | APCI: 645 [M + H]+ |
| 175 | —CH₂CH₂CH₂N(Me)Boc | APCI: 659 [M + H]+ |
| 176 | —CH₂CH₂NMe₂ | APCI: 559 [M + H]+ |
| 177 | —CH₂CH₂CH₂NMe₂ | APCI: 573 [M + H]+ |
| 178 | —CH₂CH₂NHMe | APCI: 545 [M + H]+ |
| 179 | —CH₂CH₂CH₂NHMe | APCI: 559 [M + H]+ |

| Examples | R | MS (m/z) |
|---|---|---|
| 180 | —CH₂CH₂N(Me)Boc | APCI: 677 [M + H]+ |
| 181 | —CH₂CH₂CH₂N(Me)Boc | APCI: 691 [M + H]+ |
| 182 | —CH₂CH₂NMe₂ | APCI: 591 [M + H]+ |
| 183 | —CH₂CH₂CH₂NMe₂ | APCI: 605 [M + H]+ |
| 184 | —CH₂CH₂NHMe | APCI: 577 [M + H]+ |
| 185 | —CH₂CH₂CH₂NHMe | APCI: 591 [M + H]+ |

The following compounds may be prepared by treatment in the similar manner to the synthetic procedures described herein and EXAMPLES.

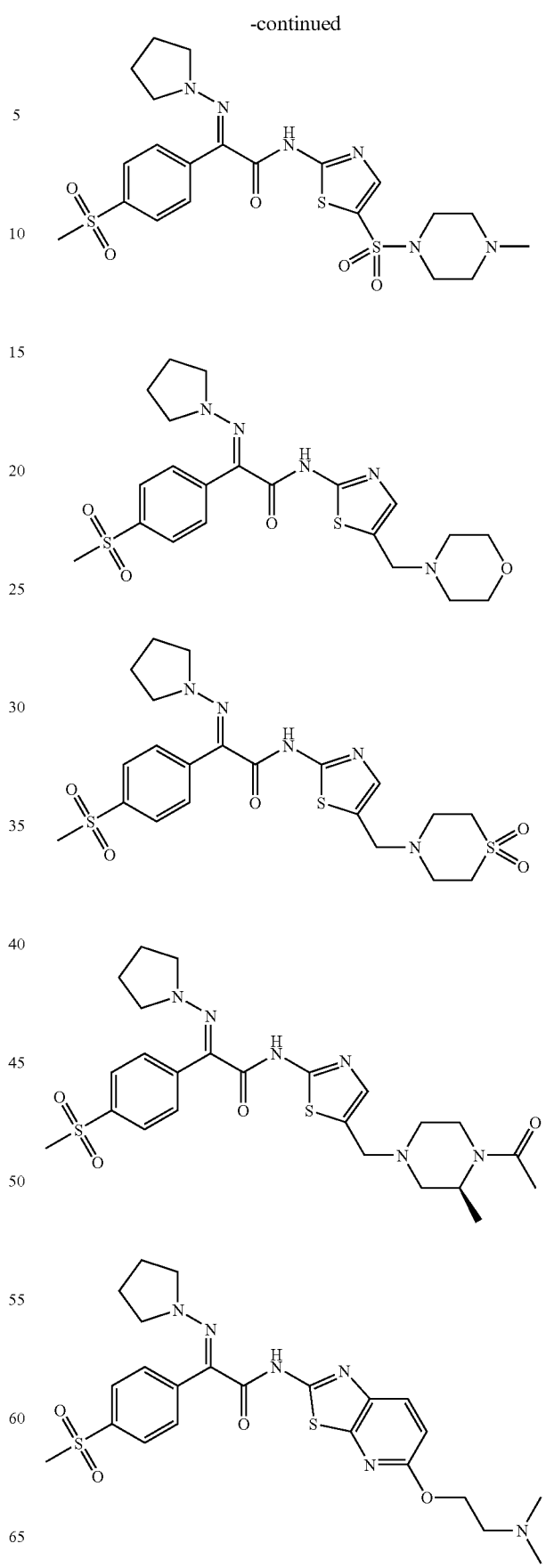

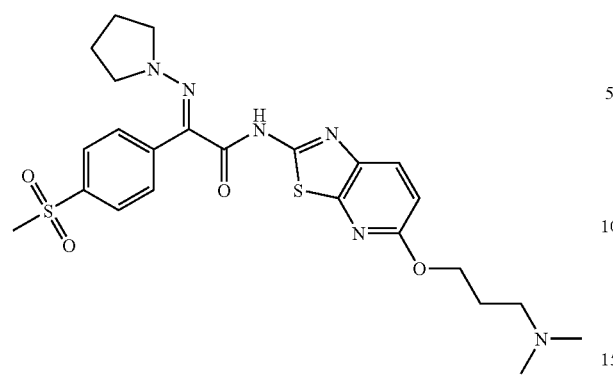
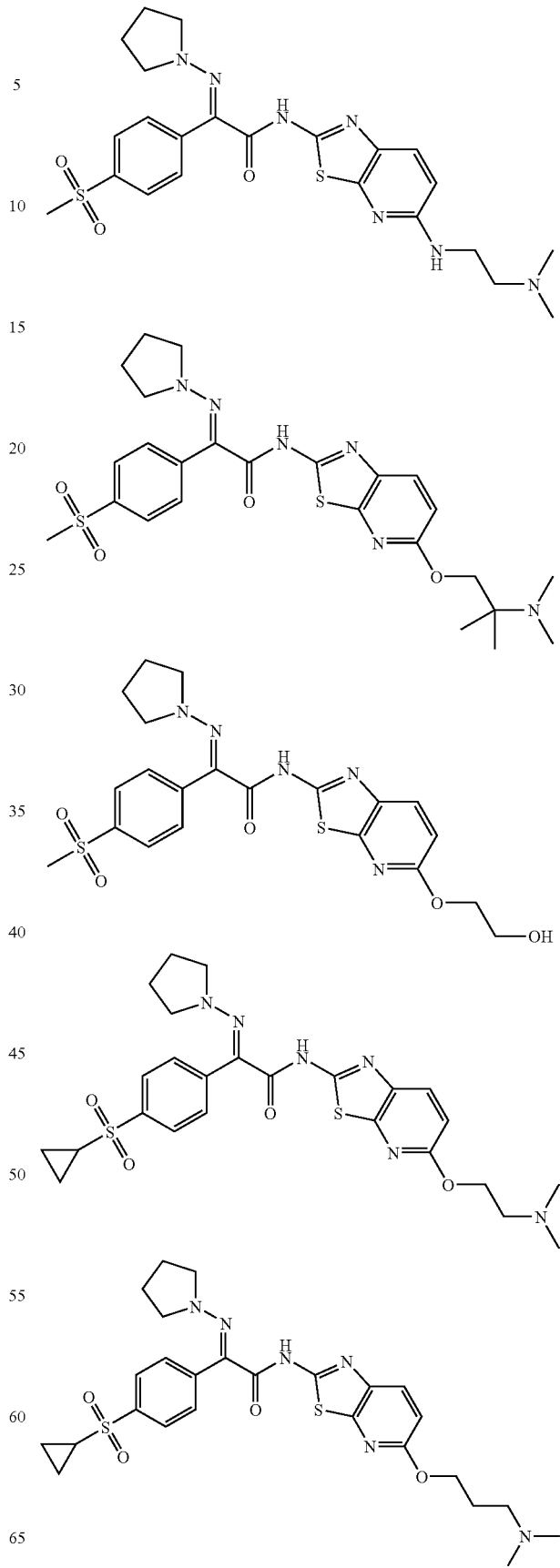

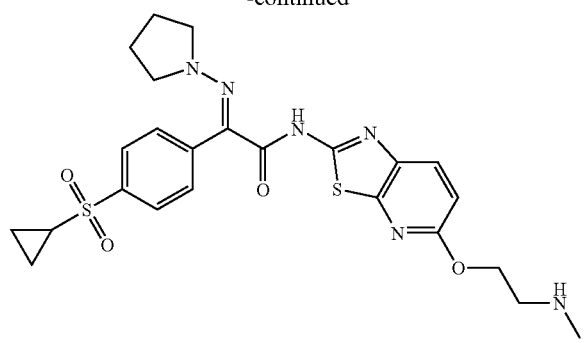
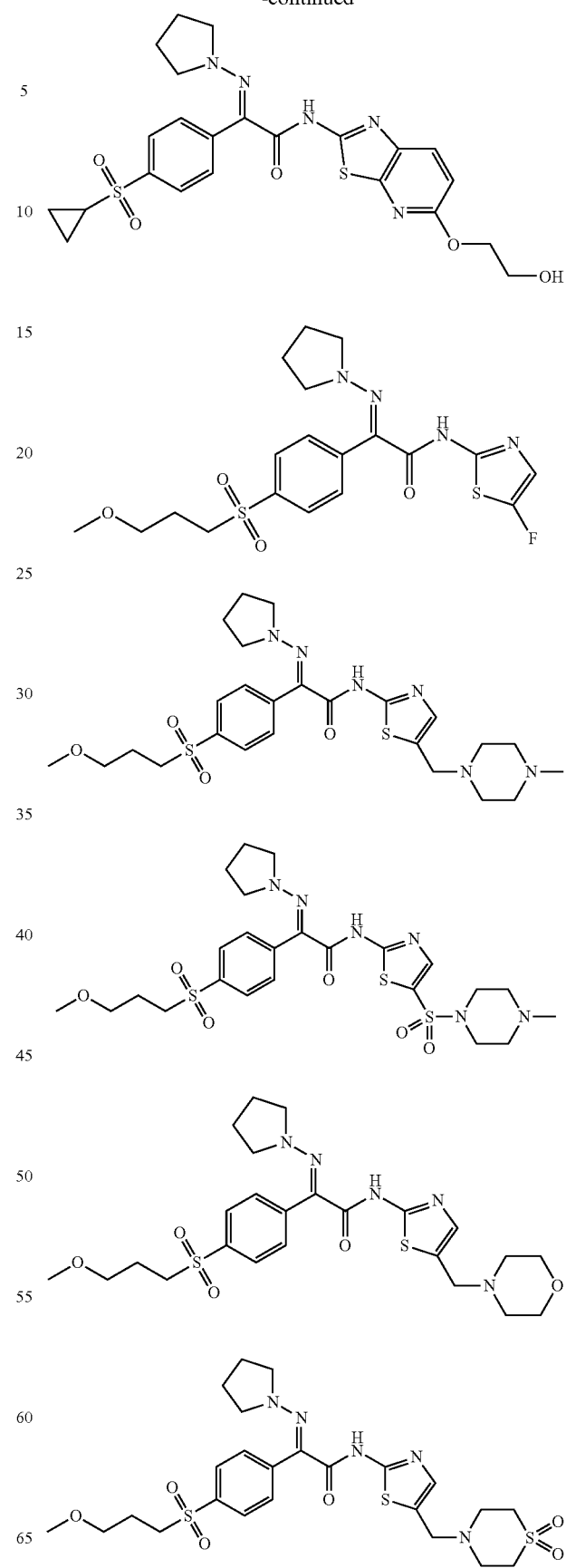

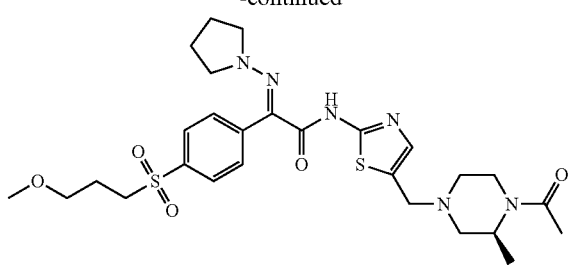
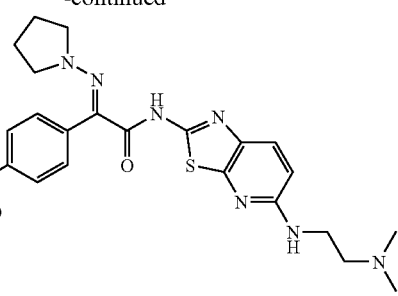
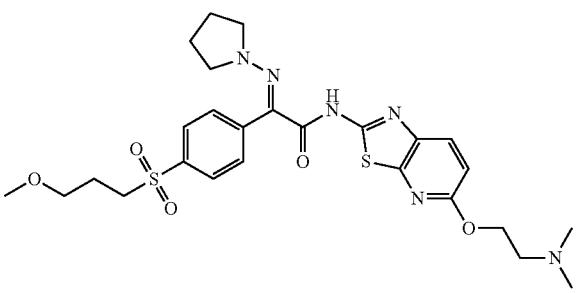
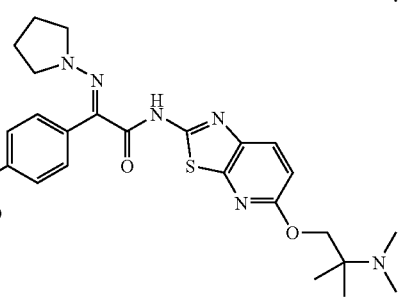
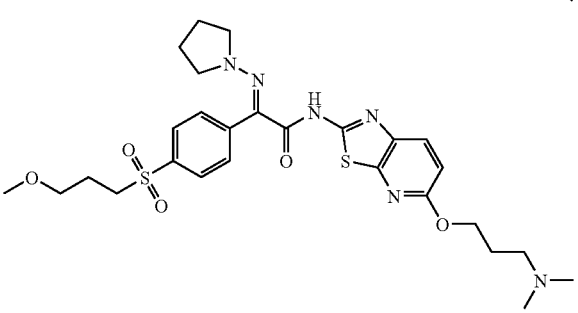
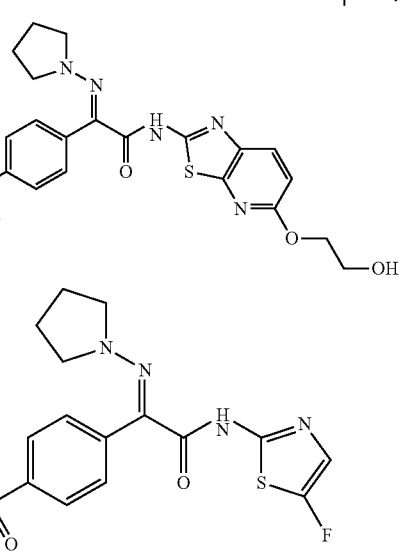
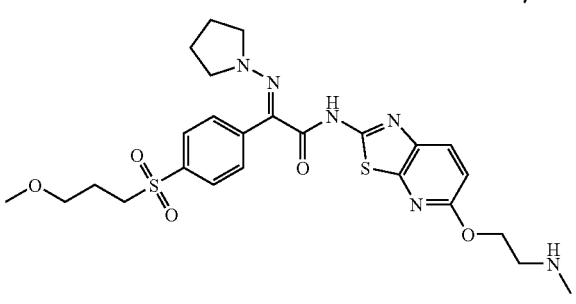
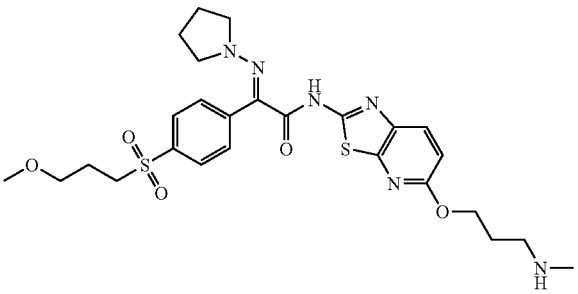
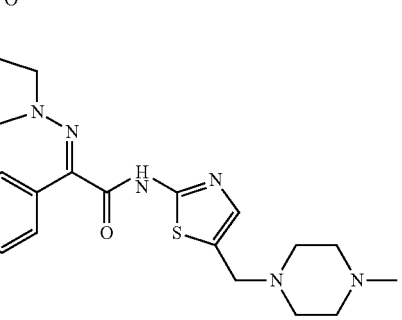
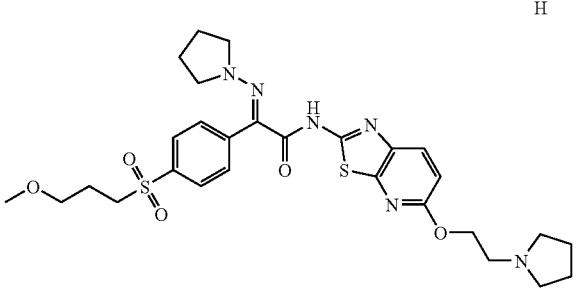
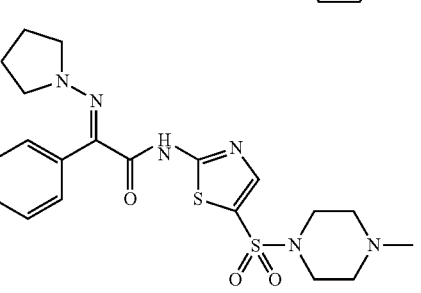

US 8,314,247 B2
63
-continued
64
-continued
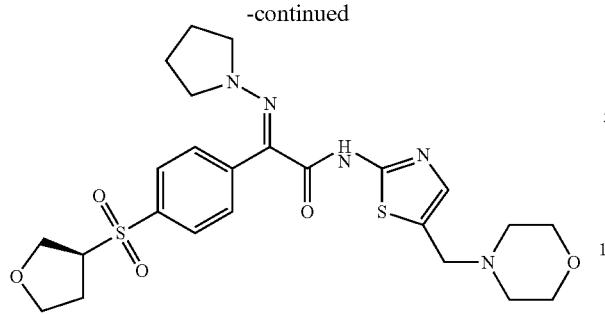
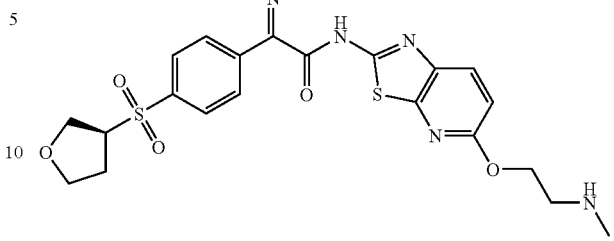
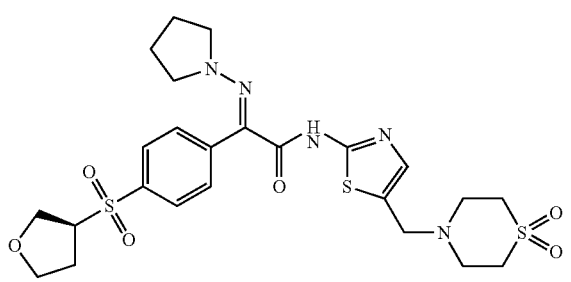
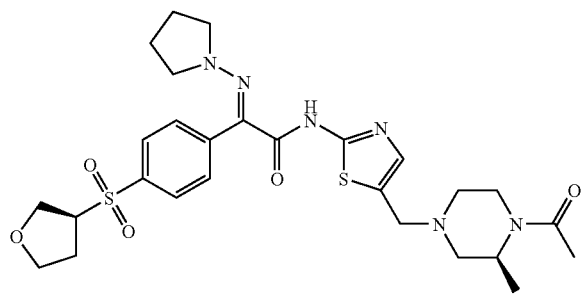
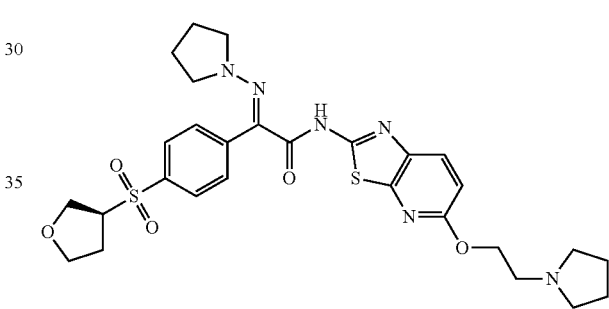
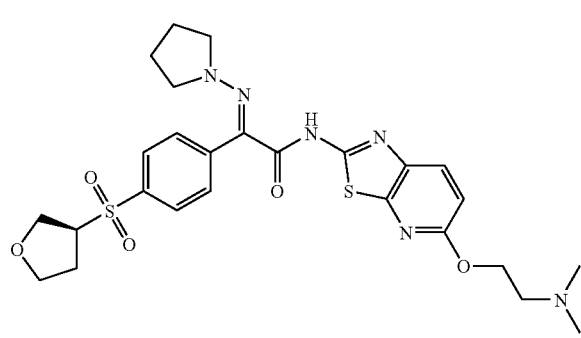
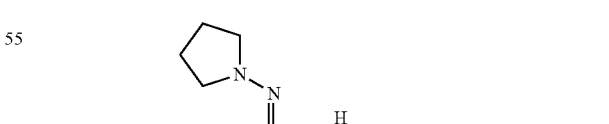
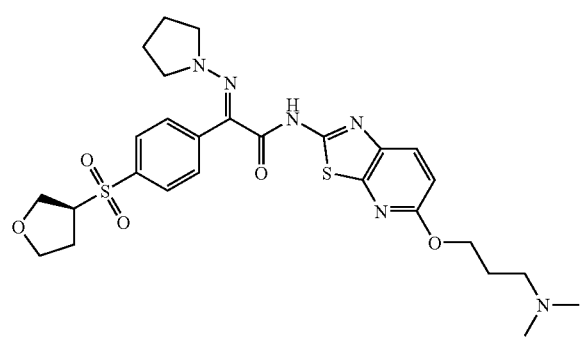
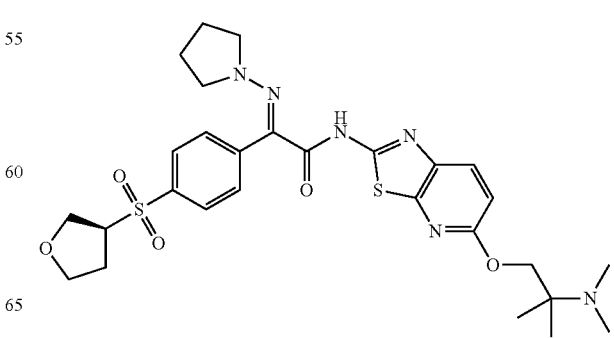

65
-continued
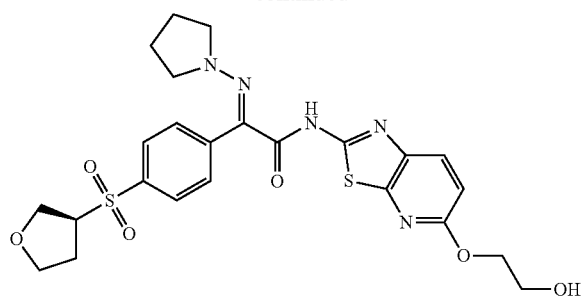
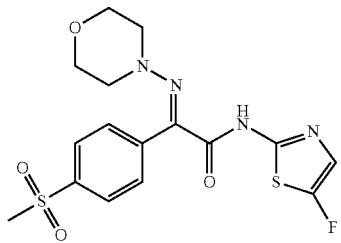
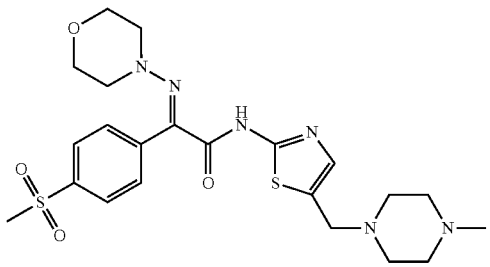
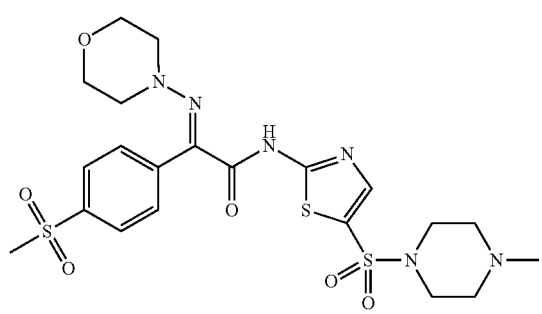
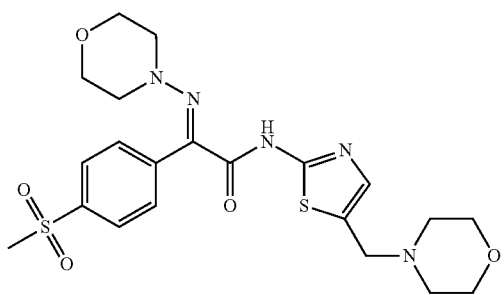
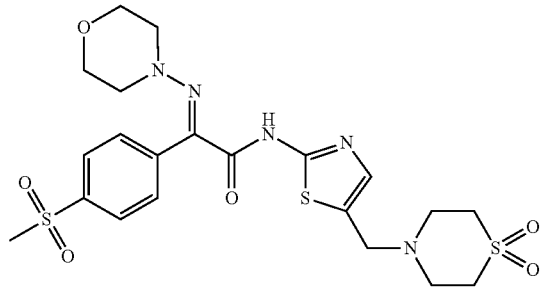
66
-continued
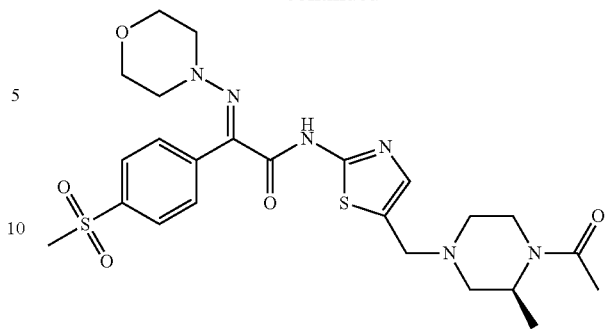
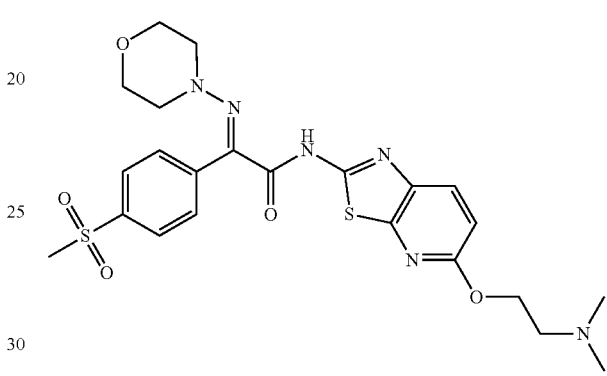
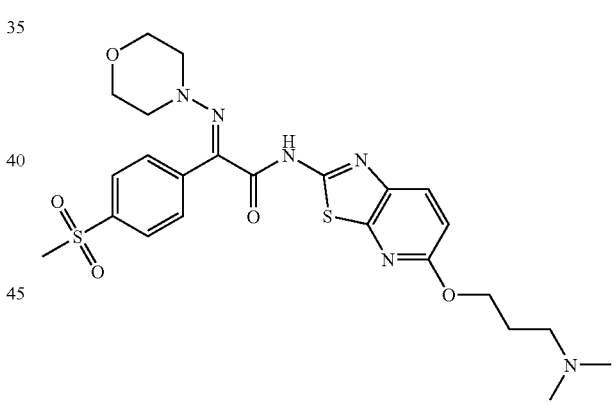
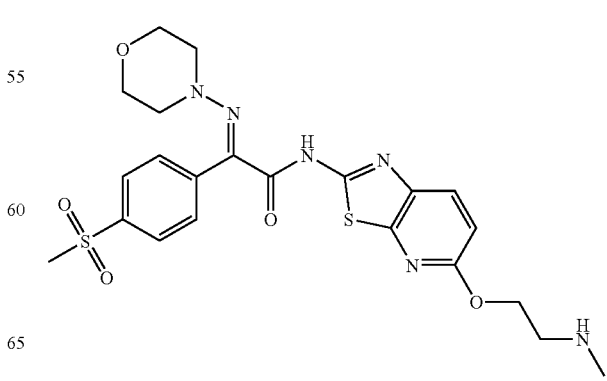

67
-continued
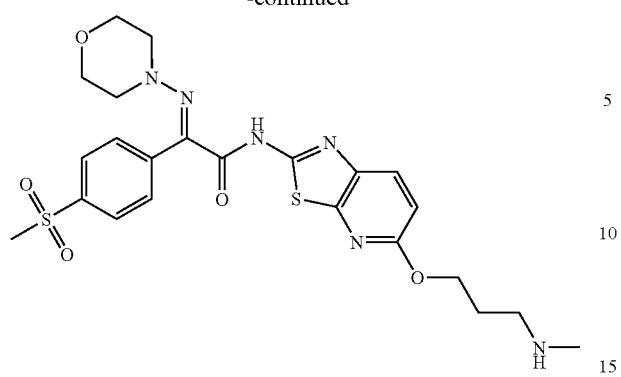
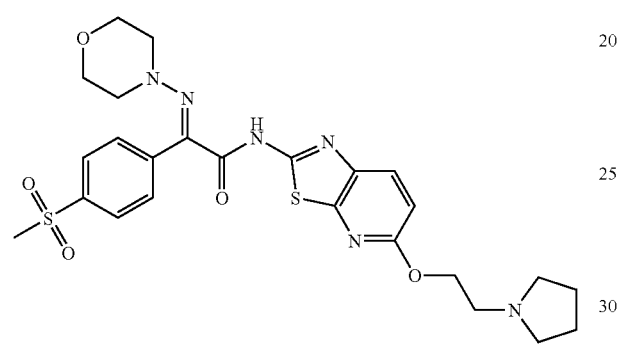
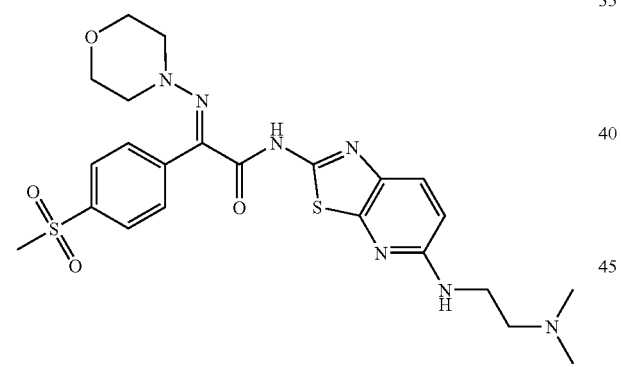
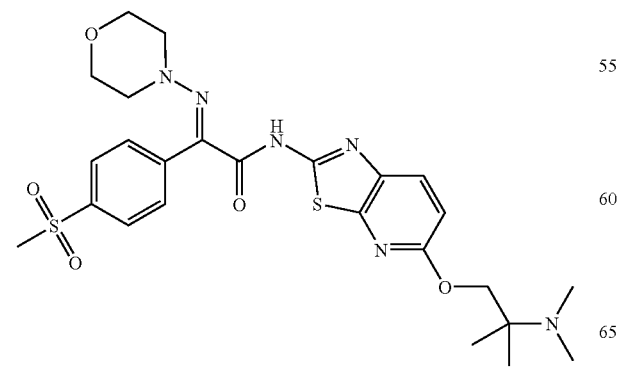
68
-continued
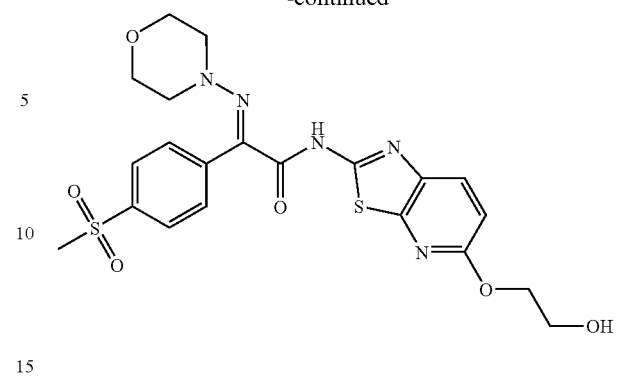
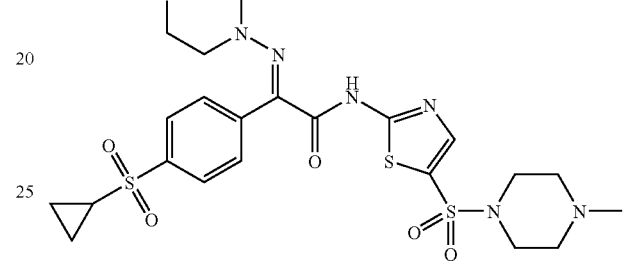
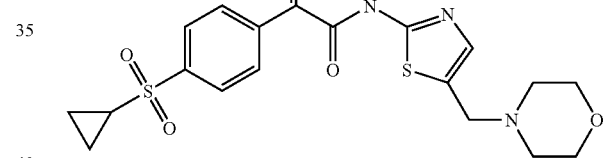
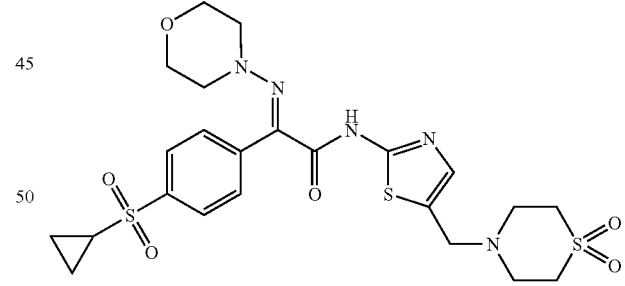
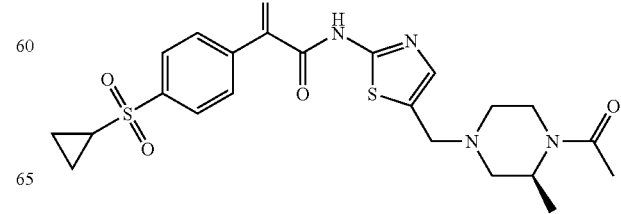

69
-continued
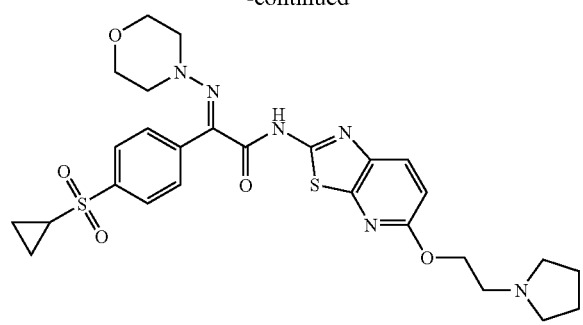
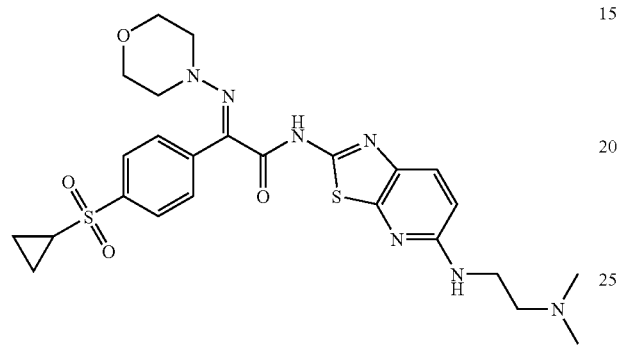
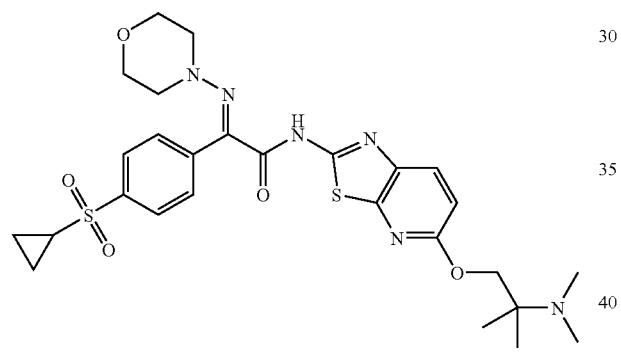
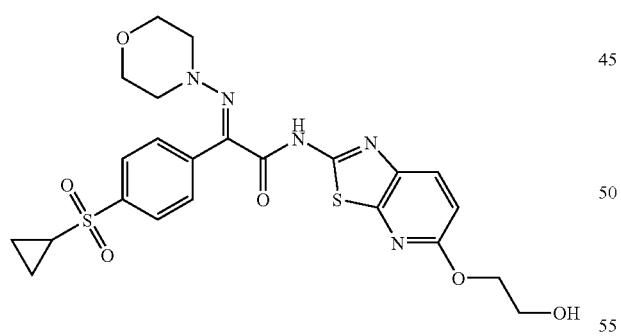
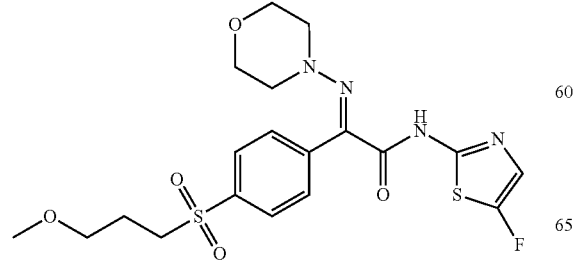
70
-continued
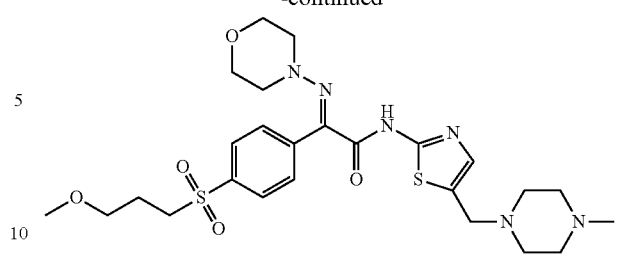
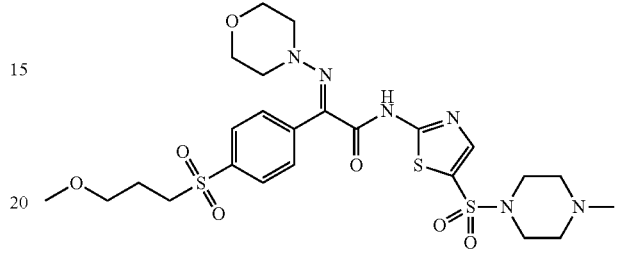
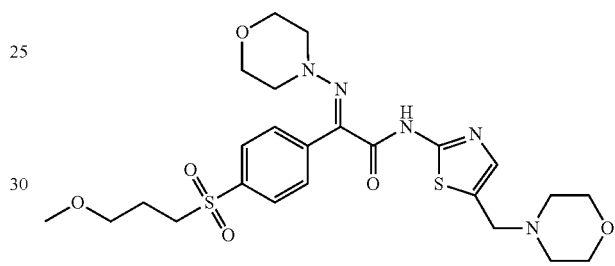
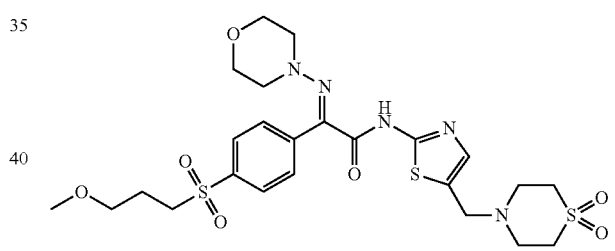
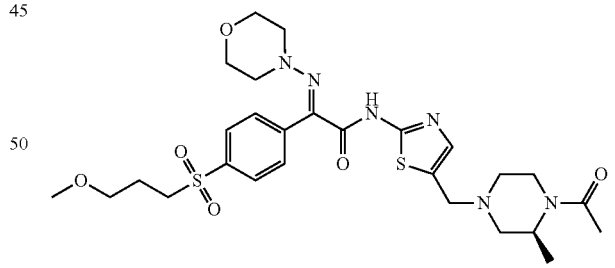
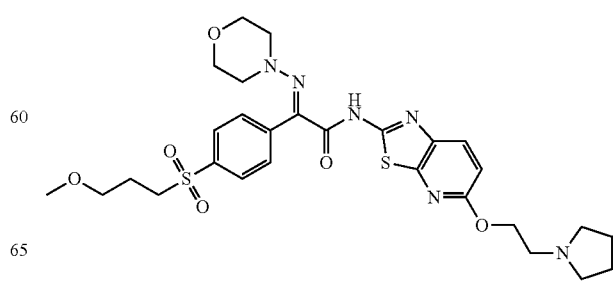

71
-continued
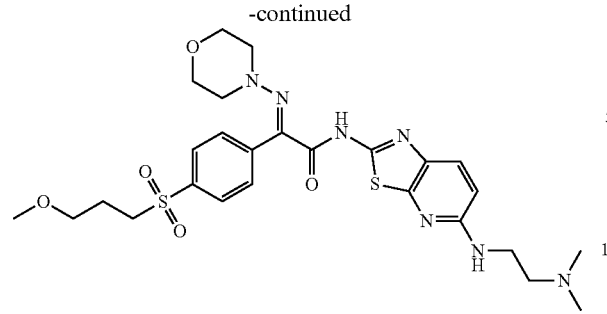
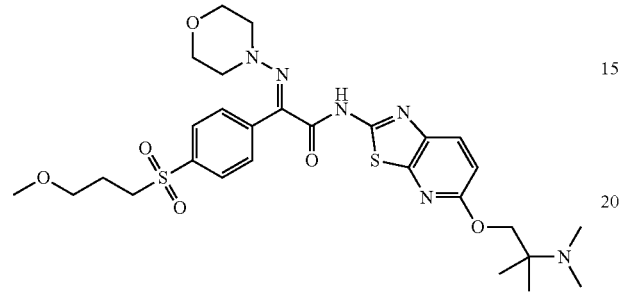
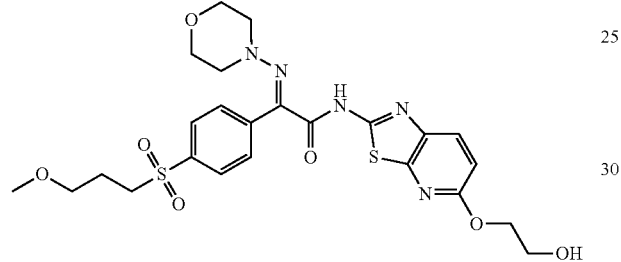
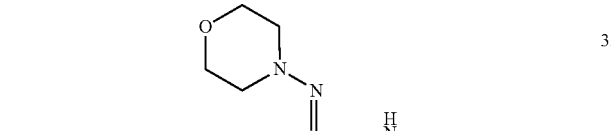
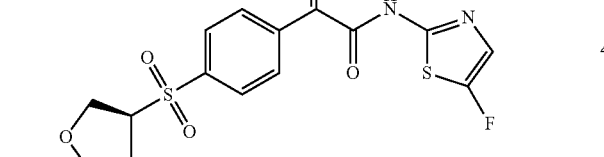
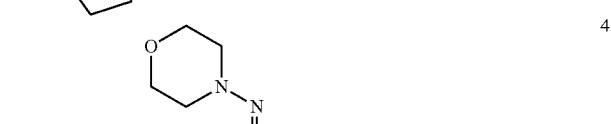
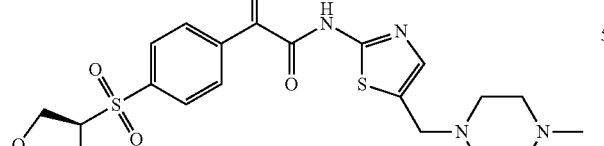
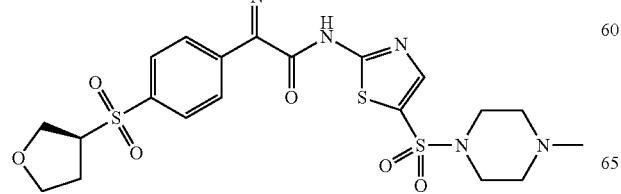
72
-continued
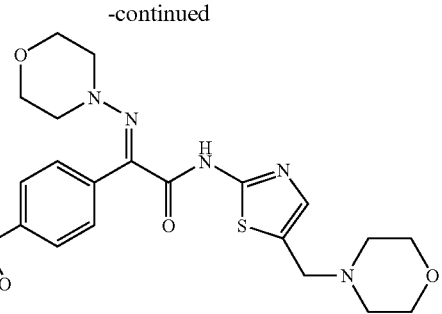
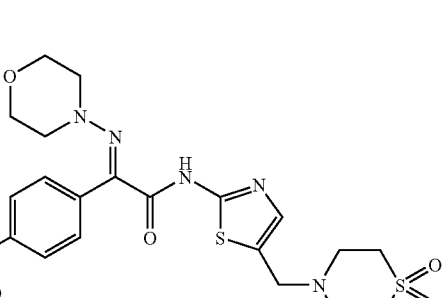
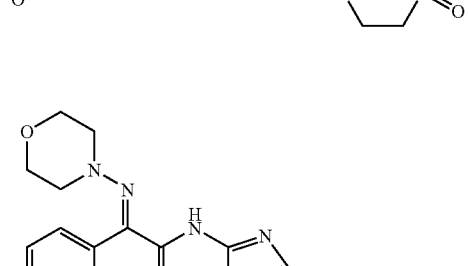
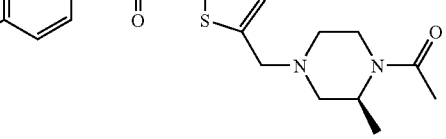
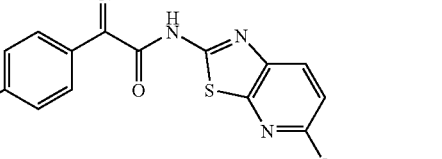
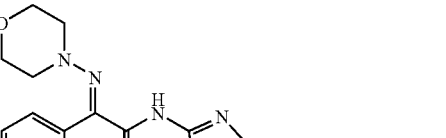
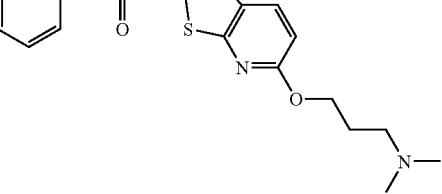

73
-continued
74
-continued
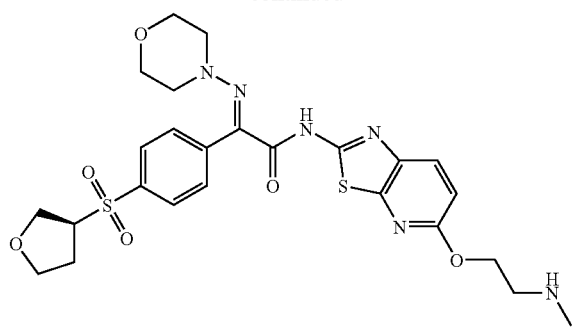
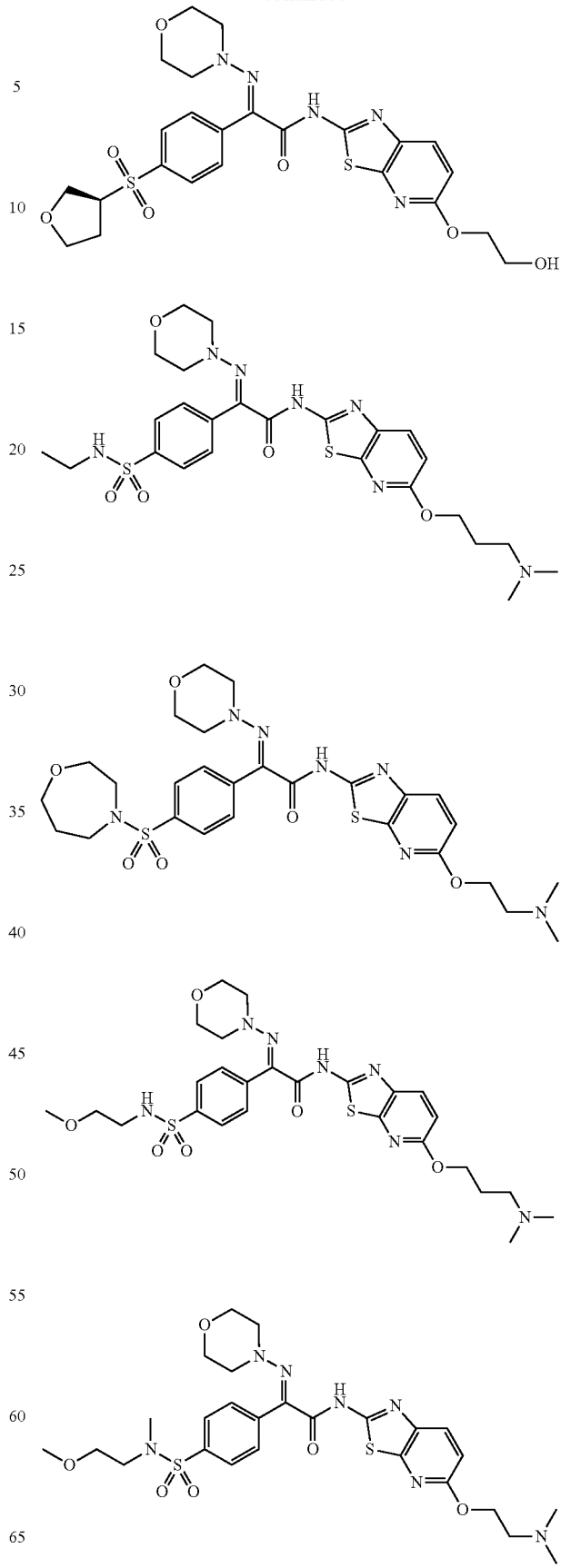

-continued

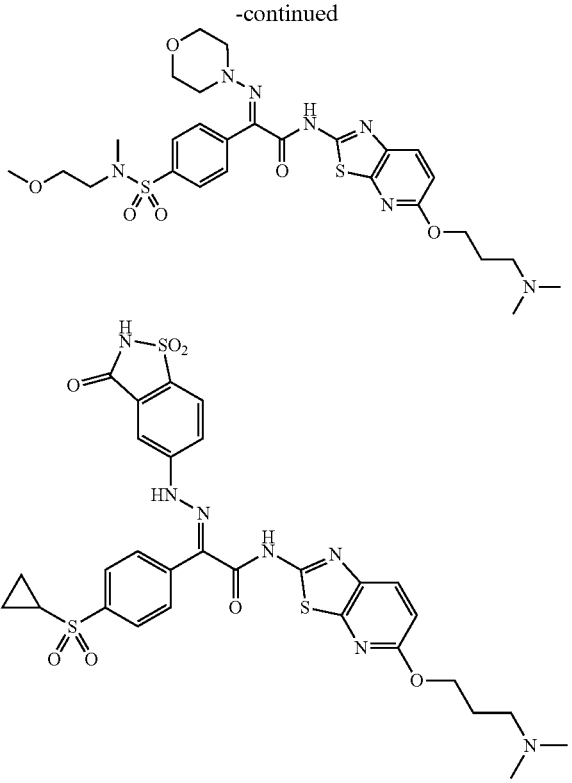

The following compounds were prepared by treatment in the similar manner to the synthetic procedures described herein and EXAMPLES.

Reference Example 1

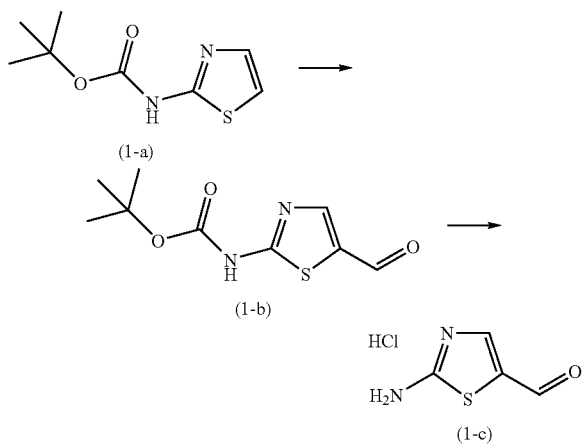

(1) To a solution of the above compound (1-a) (88.0 g, 439 mmol) in THF (1760 ml) was added dropwise a solution of n-butyllithium (1.59M) in hexane (729 ml, 1159 mmol) at −78° C. over 20 minutes, and the mixture was warmed to −10° C. over 1 hour. The mixture was cooled again to −78° C., and then thereto was added DMF (102 ml, 1320 mmol) at a time. An acetone-dry ice bath was removed, and the mixture was stirred for 30 minutes. Then, the reaction mixture was poured into cooled water (1000 ml), and thereto was added ethyl acetate (2000 ml). The organic layer was sequentially washed with water and saturated saline, dried over anhydrous magnesium sulfate and evaporated. The residue was recrystallized with ethyl acetate to give the above compound (1-b) (74.8 g).

MS (m/z) APCI: 229 [M+H]$^+$ (2) To a solution of the above compound (1-b) (64.5 g, 282 mmol) in methylene chloride (322 ml) was added dropwise trifluoroacetic acid (322 ml) under ice-cooling over 20 minutes. The reaction mixture was stirred at room temperature for 2 hours, and evaporated. To the residue was added chloroform (50 ml), and then thereto was added dropwise a solution of 4N hydrogen chloride in dioxane (300 ml) under ice-cooling. The mixture was evaporated, and then the residue was washed with ethyl acetate and dried to give the above compound (1-c) (41.3 g) as a monohydrochloride.

MS (m/z) APCI: Not Determined.

Reference Example 2

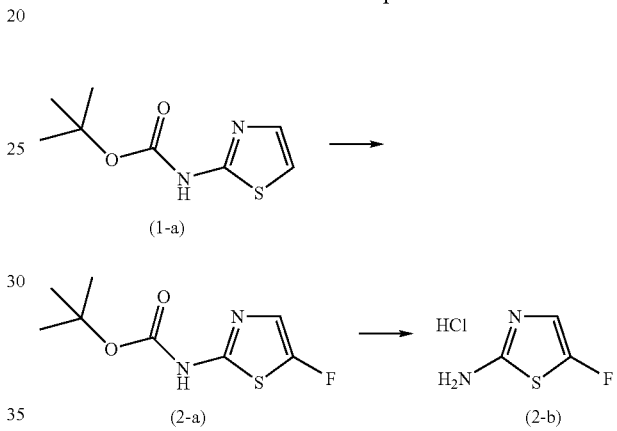

(1) To a solution of the above compound (1-a) (60.0 g, 299 mmol) in THF (1200 ml) was added dropwise a solution of n-butyllithium in hexane (1.59M) (428 ml, 659 mmol) at −78° C. over 20 minutes, and the mixture was warmed to −10° C. over 1 hour. The mixture was cooled again to −78° C., and then thereto was added N-fluorobenzene-sulfonylimide (142 g, 449 mmol) at a time. An acetone-dry ice bath was removed, and the mixture was stirred for 30 minutes. Then, the reaction mixture was poured into cooled water (1000 ml), and thereto was added ethyl acetate (1200 ml). The mixture was separated, and the organic layer was sequentially washed with 2N hydrochloric acid, water and saturated saline, and then dried over anhydrous magnesium sulfate and concentrated. The residue was purified by silica gel column chromatography (15% ethyl acetate:hexane) and recrystallized with diethyl ether to give the above compound (2-a) (45.1 g).

MS (m/z) APCI: 219 [M+H]$^+$ (2) To a solution of the above compound (2-a) (38.0 g, 174 mmol) in methylene chloride (190 ml) was added dropwise trifluoroacetic acid (190 ml) under ice-cooling for 20 minutes, and the mixture was stirred at room temperature for 2.5 hours and concentrated. To the residue was added chloroform (20 ml), and thereto was added dropwise a solution of 4N hydrochloric acid in dioxane (180 ml) under ice-cooling. The mixture was concentrated, and then the residue was washed with ethyl acetate and dried to give the above compound (2-b) (24.6 g) as a mono hydrochloride.

MS (m/z) APCI: 119 [M+H]$^+$

Reference Example 3

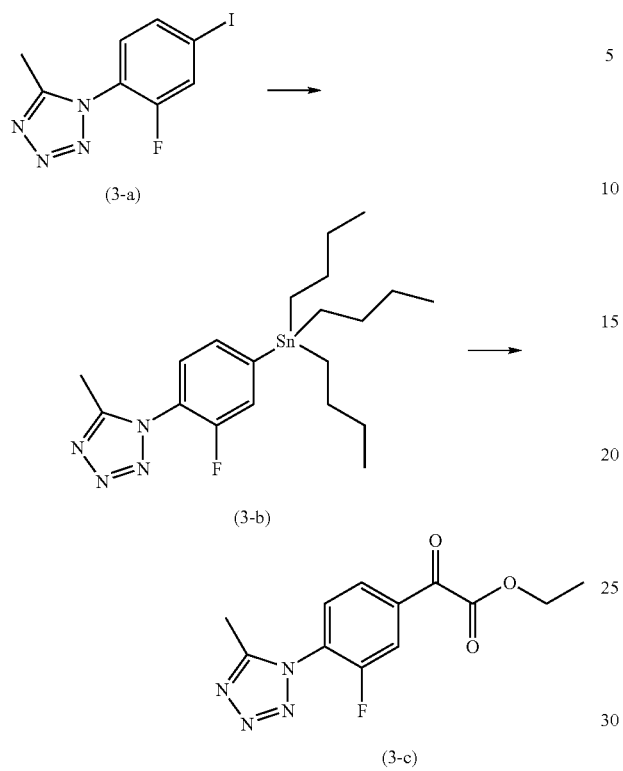

(1) A known compound (WO02/14312) (3-a) (9.30 g, 30.6 mmol) was dissolved in toluene (100 ml) under argon, and thereto were added bis(tributyltin) (35.5 g, 61.2 mmol) and tetrakis(triphenylphosphine)-palladium (0) (1.77 g, 1.53 mmol). The mixture was stirred at 120° C. for 2 days. The reaction mixture was cooled to room temperature, and directly purified by NH-silica gel column chromatography (50% ethyl acetate hexane), then further purified by silica gel chromatography (0 to 17% ethyl acetate hexane) to give tin compound (3-b) (10.70 g, yield 75%) as a pale yellow liquid.

MS (m/z) APCI: 465/467/469 [M+H]$^+$ (2) A mixture of the above tin compound (3-b) (10.7 g, 22.9 mmol), N,N-diisopropylethylamine (5.19 ml, 29.8 mmol), potassium carbonate (189 mg, 1.37 mmol), tris(dibenzylideneacetone)dipalladium (0) (1.05 g, 1.14 mmol) and THF (100 ml) was ice-cooled under argon, and thereto was slowly added dropwise ethyl chloroglyoxylate (3.83 g, 34.3 mmol). An ice bath was removed, and the mixture was stirred at room temperature for 4 hours. To the reaction mixture were added diethyl ether (15 ml), saturated aqueous potassium fluoride solution (50 ml) and water (10 ml), and the mixture was stirred at room temperature overnight and then filtered through Celite®. The filtrate was concentrated in vacuo to remove the organic solvent, and then to the resulting aqueous solution was added diethyl ether. The insoluble was filtered again through Celite®, and the filtrate was separated. The aqueous layer was extracted with diethyl ether 2 times, and the extract was combined with a first organic layer, sequentially washed with water and saturated saline, and then dried over sodium sulfate and concentrated in vacuo. The residue was purified by silica gel chromatography (30% ethyl acetate hexane, then 10% methanol-chloroform) to give keto-ester (3-c) (0.93 g, yield 15%) as a pale yellow powder.

MS (m/z) APCI: 279 [M+H]$^+$

Reference Example 4

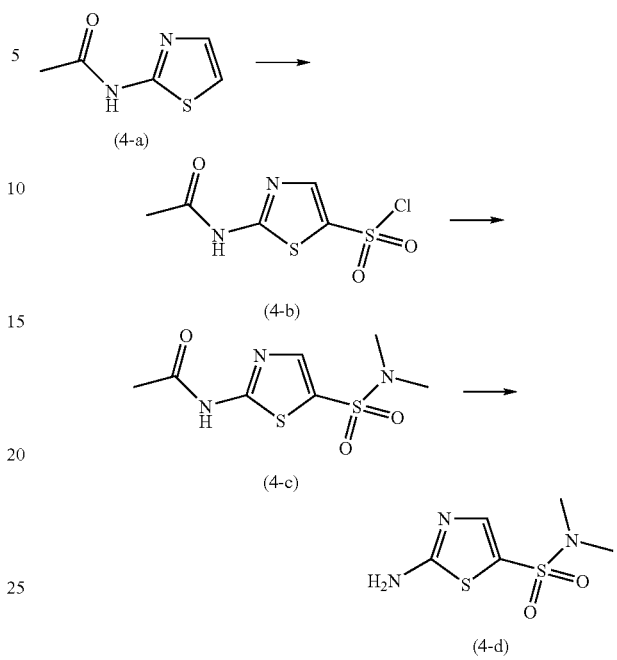

(1) Chlorosulfuric acid (80.0 g, 687 mmol) was ice-cooled, and thereto was added 2-acetamide thiazole (4-a) (20.00 g, 140.6 mmol) in several portions. Then, the mixture was stirred at 100° C. overnight. The reaction mixture was cooled to room temperature, and then poured into ice water and extracted with diethyl ether. The extract was washed with water and saturated saline, dried over sodium sulfate, and then concentrated in vacuo to give a crude product (4-b) (9.41 g) as a yellow solid.

(2) A mixture of an aqueous solution of 2M dimethylamine (7.2 ml, 14 mmol) and pyridine (3 ml) was ice-cooled, and thereto was added compound (4-b) (1.50 g) in several portions. The mixture was stirred at the same temperature for 15 minutes and at room temperature overnight. The reaction mixture was concentrated in vacuo, and the residue was purified by silica gel chromatography (0 to 10% methanol-chloroform) to give a crude product (4-c) (677 mg) as a yellow powder.

(3) To the above compound (4-c) (447 mg) was added 6N hydrochloric acid, and the mixture was stirred at 110° C. for 1 hour. The reaction mixture was cooled to room temperature and concentrated in vacuo. To the residue were added water and ammonia water to be basified, and the precipitated crystal was combined and dried to give compound (4-d) (283 mg, yield 9% in 3 steps) as a yellow powder.

MS (m/z) APCI: 208 [M+H]$^+$

Reference Example 5

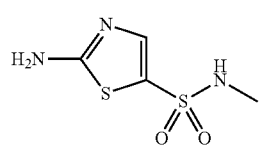

MS (m/z) APCI: 194 [M+H]$^{30}$

The corresponding starting compound was treated in the similar manner to REFERENCE EXAMPLE 4 to give the above compound.

Reference Example 6

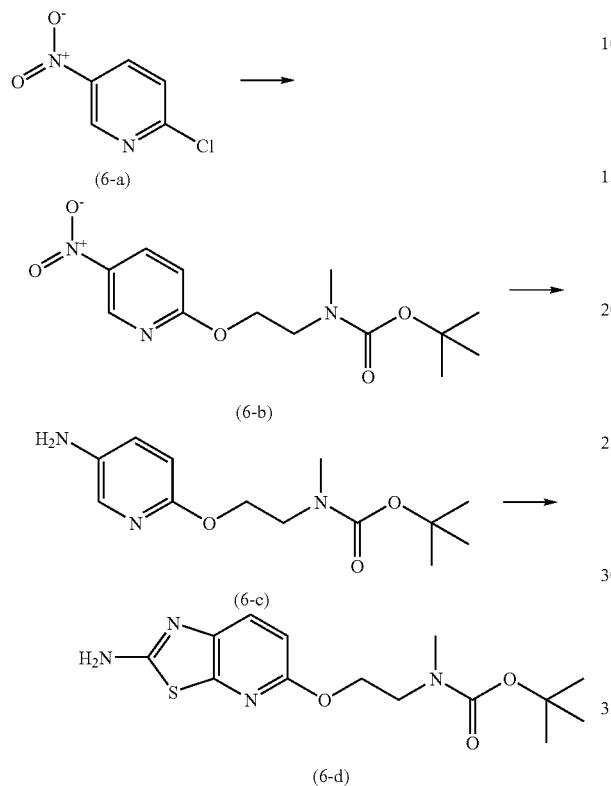

(1) To a solution of compound (6-a) (10.0 g, 63.1 mmol) and N-(-butoxycarbonyl)-N-methylethanolamine (16.55 g, 94.6 mmol) in dimethylsulfoxide (100 ml) was added portionwise potassium t-butoxide (10.6 g, 94.6 mmol) with cooling by an ice-water bath, and the mixture was stirred at room temperature for 50 minutes. The reaction mixture was diluted with ethyl acetate, and then washed with water and saturated saline, dried over sodium sulfate, treated by activated carbon, and then concentrated in vacuo to give a crude product (6-b) (21.8 g).

MS (m/z) APCI: 298 $[M+H]^+$ (2) To a solution of the above compound (6-b) (18.5 g) in ethyl acetate (200 ml) was added 10% palladium carbon (dried) (1.00 g), and the mixture was vigorously stirred at room temperature for 3 hours at normal pressure under hydrogen. The reaction mixture was filtered, and the filtrate was concentrated in vacuo to give a crude amine (6-c) (17.1 g).

MS (m/z) APCI: 268 $[M+H]^+$ (3) To a solution of the above amine (6-c) (20.1 g) in acetic acid (250 ml) were added potassium acetate (31.0 g, 319 mmol) and potassium thiocyanate (36.8 g, 379 mmol), and thereto was added dropwise bromine (3.40 ml, 66.4 mmol) with cooling by an ice-water bath. Then, the mixture was stirred at room temperature for 2 hours. The reaction mixture was diluted with ethyl acetate, washed with water, aqueous sodium sulfite solution and saturated saline, dried over sodium sulfate, treated by activated carbon, and then evaporated in vacuo. The residue was crystallized with ethyl acetate to give the above compound (6-d) (13.36 g, yield 65% in 3 steps).

MS (m/z) APCI: 325 $[M+H]^+$

Reference Example 7

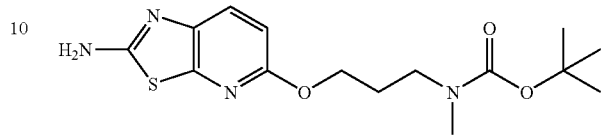

MS (m/z) APCI: 339 $[M+H]^+$

The corresponding starting compound was treated in the similar manner to REFERENCE EXAMPLE 6 to give the above compound.

Reference Example 8

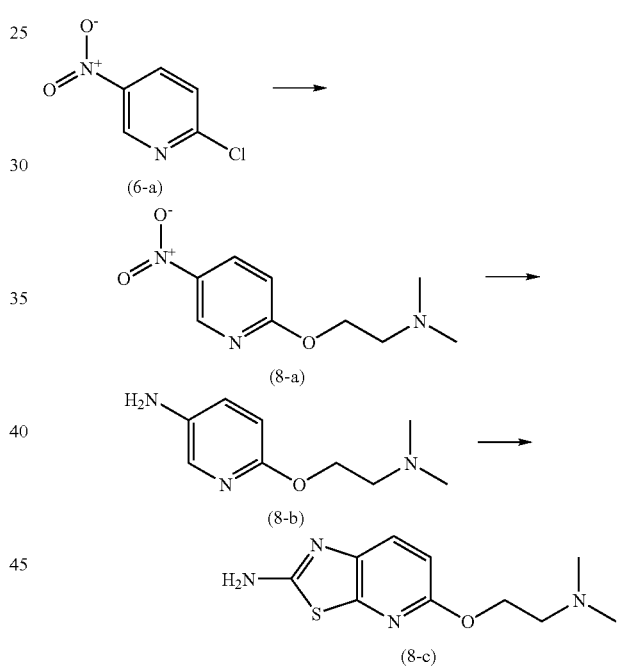

(1) A mixture of the above compound (6-a) (30.0 g, 94.6 mmol), N,N-dimethylethanolamine (22.7 ml, 227.1 mmol), potassium carbonate (52.3 g, 378.5 mmol) and DMF (150 ml) was stirred at 60° C. for 2 hours. The reaction mixture was cooled to room temperature, and then filtered through Celite®. The filtrate was concentrated in vacuo, and to the resulting residue was added water. The mixture was extracted with ethyl acetate 2 times. The extract was combined, washed with saturated saline, dried (sodium sulfate), treated by activated carbon, and then concentrated in vacuo to give a crude nitro compound (8-a) (36.10 g).

(2) To a solution of the above crude nitro compound (8-a) (36.10 g) in methanol (300 ml) was added 10% palladium carbon (dried) (5.0 g), and the mixture was vigorously stirred for 5 hours under hydrogen. The reaction solution was filtered, and the filtrate was concentrated in vacuo to give a crude amine (8-b) (31.96 g).

(3) To a solution of the above crude amine (8-b) (31.96 g) in acetic acid (300 ml) was added potassium thiocyanate (110.3 g, 1135 mmol), and thereto was added dropwise bromine (10.2 ml, 199 mmol) with cooling by an ice bath. Then, the mixture was stirred at room temperature for 2.5 days. The reaction solution was concentrated in vacuo, azeotroped with toluene, and then to the residue were added water and saturated sodium bicarbonate water, then sodium chloride. The mixture was filtered through Celite®, and the aqueous layer was alkalified by adding 28% ammonia water to the filtrate. Then, the mixture was extracted with chloroform 4 times. The extract was combined, dried over sodium sulfate, and evaporated. The residue was dissolved in methanol, treated by activated carbon, and then concentrated in vacuo. The residue was washed with ethyl acetate to give compound (8-c) (22.2 g, yield 49% in 3 steps) as a pale red powdery solid.

MS (m/z) APCI: 239 [M+H]$^+$

Reference Example 9

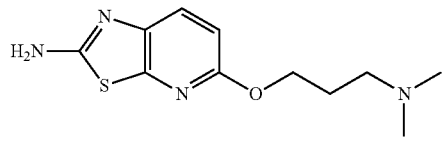

MS (m/z) APCI: 253 [M+H]$^+$

The corresponding starting compound was treated in the similar manner to REFERENCE EXAMPLE 8 to give the above compound.

Reference Example 10

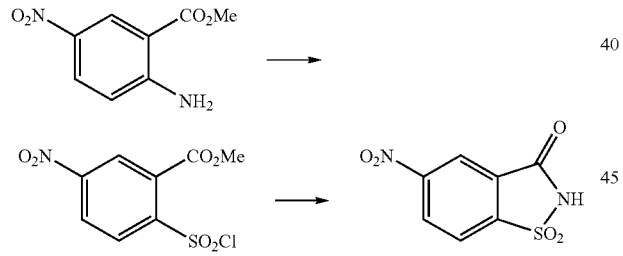

To a mixed solution of methyl 2-amino-4-nitrobenzoate (4.3 g, 22 mmol) in ethyl acetate (21 ml) and concentrated hydrochloric acid (39 ml) was added dropwise an aqueous solution (10 ml) of sodium nitrite (1.61 g, 23 mmol) with cooling by an ice bath, and the mixture was stirred at the same temperature for 30 minutes. Thereto was added dropwise a mixed solution of copper (II) chloride dihydrate (1.76 g, 10 mmol), sodium bisulfite (23 g, 220 mmol), acetic acid (28 ml) and concentrated hydrochloric acid (10 ml), and the mixture was stirred at room temperature for 30 minutes. The reaction solution was poured into ice, and the precipitated sulfonyl chloride was filtered and washed with water. The resulting sulfonyl chloride was added to saturated ammonia water at room temperature, and the mixture was stirred at the same temperature for 2 days. The mixture was adjusted to pH 1 to 2 by concentrated hydrochloric acid, extracted with ethyl acetate, and the extract was washed with water and saturated saline, dried over sodium sulfate, and then concentrated in vacuo. The residue was filtered by ethyl acetate-hexane to give the above compound (3.0 g, yield 60%).

MS (m/z): 227 [M−H]$^+$

Reference Example 11

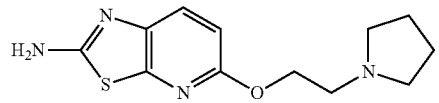

MS (m/z) APCI: 265 [M+H]$^+$

The corresponding starting compound was treated in the similar manner to REFERENCE EXAMPLE 8 to give the above compound.

Reference Example 12

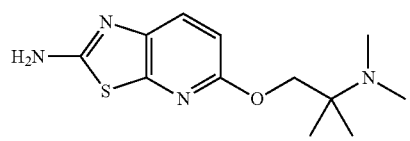

MS (m/z) APCI: 267 [M+H]$^+$

The corresponding starting compound was treated in the similar manner to REFERENCE EXAMPLE 8 to give the above compound.

Reference Example 12-1

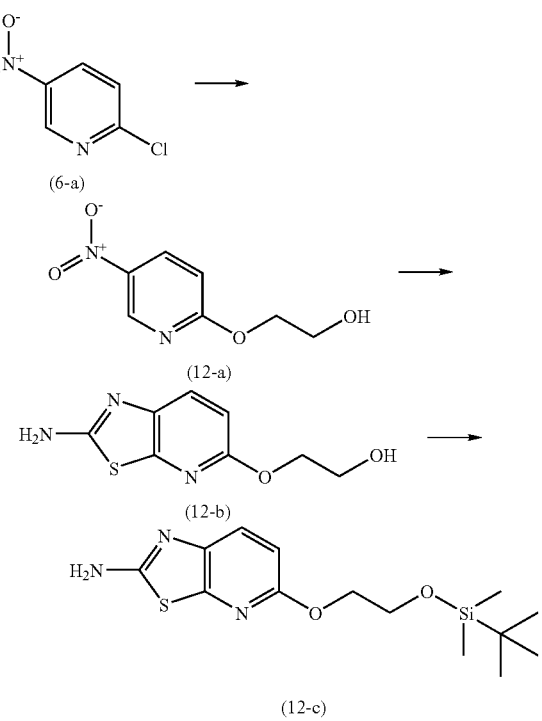

(1) To a solution of compound (6-a) (5.18 g, 32.7 mmol) and ethylene glycol (20.3 g, 327 mmol) in DMF (20 ml) was added potassium carbonate (13.6 g, 98.0 mmol), and the mixture was stirred at room temperature for 2 hours. The reaction mixture was diluted with ethyl acetate, and then the organic layer was washed with water and saturated saline, dried over sodium sulfate, and concentrated in vacuo. The residue was recrystallized with ethyl acetate-hexane to give compound (12-a) (5.59 g, yield 93%) as a yellow crystal.

MS (m/z) APCI: 185 [M+H]⁺

(2) To a solution of compound (12-a) (5.57 g, 30.3 mmol) in ethanol (50 ml) was added 10% palladium carbon (0.50 g), and the mixture was vigorously stirred for 2 hours under hydrogen. The reaction mixture was concentrated in vacuo to give a crude amine.

(3) To a solution of the above amine in acetic acid (100 ml) was added potassium thiocyanate (17.6 g, 182 mmol), and thereto was added dropwise bromine (1.62 ml, 31.8 mmol) with cooling by an ice bath. Then, the mixture was stirred at room temperature overnight. The reaction mixture was concentrated in vacuo, azeotroped with toluene, and then the residue was purified by silica gel chromatography (NH-silica gel; 5 to 9% methanol-chloroform) and triturated with ethyl acetate to give compound (12-b) (5.55 g, yield 87%) as a colorless crystal.

MS (m/z) APCI: 212 [M+H]⁺

(4) To a solution of the above compound (175 mg, 0.833 mmol) and imidazole (188 mg, 2.76 mmol) in DMF (4 ml) was added dropwise a solution of t-butyldimethylchlorosilane (188 mg, 1.25 mmol) in DMF (2 ml) under ice-cooling, and the mixture was stirred at room temperature overnight. The reaction mixture was diluted with ethyl acetate, washed with water and saturated saline, and then dried over sodium sulfate. The mixture was concentrated in vacuo, and then the residue was purified by silica gel chromatography (40 to 70% ethyl acetate-hexane) to give compound (12-c) (172 mg) as a colorless crystal.

MS (m/z) APCI: 326 [M+H]⁺

Reference Example 13 monohydrate (313 mg, 1.64 mmol) in toluene (30 ml) was heated to reflux for 6 hours with removing water by Dean-Stark instrument. The reaction mixture was cooled to room temperature, and then diluted with ethyl acetate. The mixture was washed with saturated sodium bicarbonate water and saturated saline, dried over sodium sulfate, and concentrated in vacuo. Then, the residue was purified by silica gel chromatography (9% ethyl acetate-hexane) to give compound (13-b) (3.84 g, yield 89%) as a pale brown crystal.

MS (m/z) APCI: 264/266 [M+h]⁺

(2) A mixture of the above compound (13-b) (1.00 g, 3.79 mmol) and N,N-dimethylethylenediamine (3.34 g, 37.0 mmol) was stirred at 120° C. for 15 hours. The reaction mixture was cooled to room temperature, and purified by NH-silica gel chromatography (30 to 60% ethyl acetate-hexane) to give compound (13-c) as a yellow powder.

MS (m/z) APCI: 316 [M+H]⁺

(3) A mixture of the above compound (13-c) (500 mg, 1.59 mmol), methanol (2.0 ml) and 10% hydrochloric acid (3.3 ml) was stirred at 60° C. for 19 hours. The reaction mixture was cooled to room temperature, neutralized by adding sodium bicarbonate powder, and then concentrated in vacuo. The residue was diluted with chloroform, dried over magnesium sulfate, and then concentrated in vacuo. Then, the residue was washed with a mixed solvent of ethyl acetate-diethyl ether to give the above compound (13-d) as a brown powder.

MS (m/z) APCI: 238 [M+h]⁺

INDUSTRIAL APPLICABILITY

The present invention may provide a novel compound having an excellent glucokinase activation effect, which is useful as an active ingredient of a medicine for preventing and/or treating diseases involving glucokinase such as diabetes, complication of diabetes or obesity.

The invention claimed is:
1. A hydrazone derivative of the formula [I]:

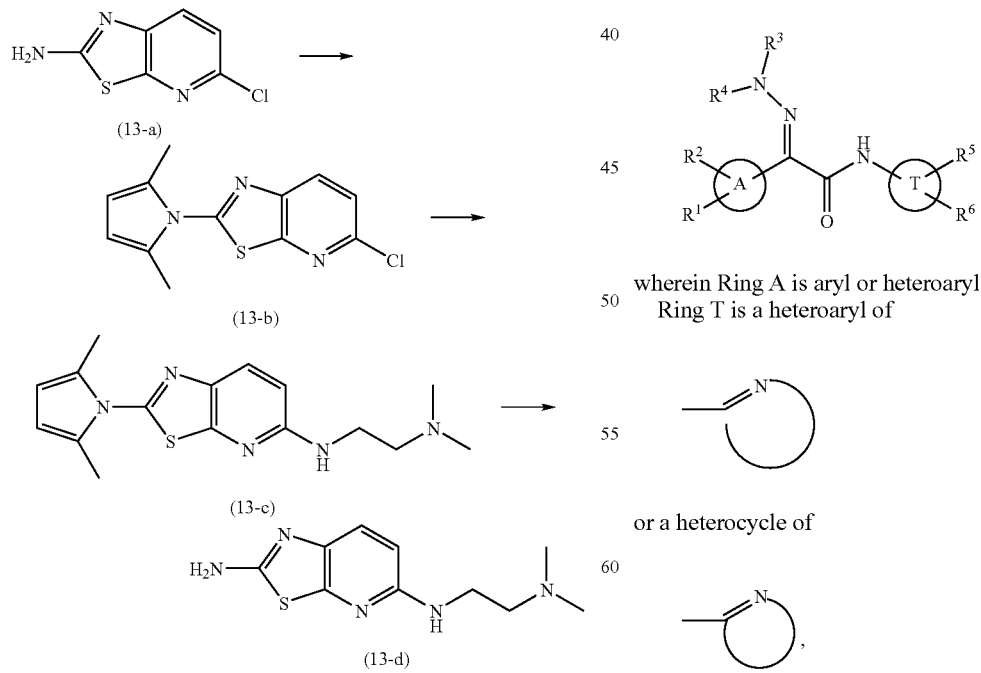

wherein Ring A is aryl or heteroaryl;
Ring T is a heteroaryl of or a heterocycle of

, wherein the heteroaryl or heterocycle of Ring T is selected from the group consisting of thiazolyl, thiazolopyridinyl, pyridyl, pyrazinyl, benzothiazolyl, quinolyl, thiadiazolyl, pyrazolyl, thiazolopyrazinyl, thiazolopyrimidinyl, cyclohexanothiazolyl and dihydropyrazolopyridinyl;

$R^1$ is hydrogen atom, halogen atom, cycloalkylsulfonyl, alkylsulfonyl, alkylsulfinyl, alkylthio, substituted or unsubstituted tetrazolyl, —$COR^{10}$ or —$CR^{12}(OH)R^{10}$;

$R^2$ is hydrogen atom, halogen atom, cycloalkylsulfonyl, substituted or unsubstituted alkylsulfonyl, substituted or unsubstituted alkylthio, nitro, substituted or unsubstituted amino, substituted or unsubstituted aminosulfonyl, substituted or unsubstituted heterocyclyl-thio, substituted or unsubstituted heterocyclyl-sulfinyl, substituted or unsubstituted heterocyclyl-sulfonyl, substituted or unsubstituted heteroarylsulfonyl, alkenyloxy, substituted or unsubstituted alkoxy, substituted or unsubstituted alkylsulfinyl, substituted or unsubstituted heteroaryl, substituted or unsubstituted heteroarylthio, —$COR^{11}$ or —$CR^{13}(OH)R^{11}$;

$R^{10}$ is alkyl, cycloalkyl, heteroaryl or heterocycle;

$R^{11}$ is substituted or unsubstituted alkyl, substituted or unsubstituted cycloalkyl, substituted or unsubstituted heteroaryl or heterocycle;

$R^{12}$ is hydrogen atom or alkyl;

$R^{13}$ is hydrogen atom or alkyl;

$R^3$ and $R^4$ are independently hydrogen atom, substituted or unsubstituted alkyl or substituted or unsubstituted heteroaryl; or $R^3$ and $R^4$ combine each other together with the adjacent nitrogen atom to form substituted or unsubstituted heterocycle;

$R^5$ is hydrogen atom, formyl, halogen atom, oxo, substituted or unsubstituted alkoxy, substituted or unsubstituted aminosulfonyl, substituted or unsubstituted alkylthio, cyano, substituted or unsubstituted heterocyclyl-sulfonyl, nitro, substituted or unsubstituted cycloalkyl, alkoxycarbonyl, alkenyl, alkylsulfonyl, substituted or unsubstituted carbamoyl, substituted or unsubstituted heteroarylthio, substituted or unsubstituted amino, carboxy, substituted or unsubstituted heteroaryl, substituted or unsubstituted alkynyl, substituted or unsubstituted heterocyclyl-carbonyl, substituted or unsubstituted heterocyclyl-oxy, substituted or unsubstituted heterocycle, substituted or unsubstituted heterocyclyl-thio, substituted or unsubstituted cycloalkyloxy, alkanoyl, or substituted or unsubstituted alkyl;

$R^6$ is hydrogen atom, substituted or unsubstituted alkyl, halogen atom, or carboxy;

or a pharmaceutically acceptable salt thereof.

2. The hydrazone derivative as claimed in claim 1, wherein Ring T is thiazolyl, thiazolopyridinyl, pyridyl, pyrazinyl, benzothiazolyl, thiadiazolyl, thiazolopyrazinyl, thiazolopyrimidinyl, cyclohexanothiazolyl or dihydropyrazolopyridinyl, or a pharmaceutically acceptable salt thereof.

3. The hydrazone derivative as claimed in claim 1, wherein Ring T is thiazolyl, thiazolopyridinyl, pyrazinyl, thiadiazolyl, thiazolopyrazinyl or thiazolopyrimidinyl, or a pharmaceutically acceptable salt thereof.

4. The hydrazone derivative as claimed in claim 1, wherein Ring T is thiazolyl or thiazolopyridinyl, or a pharmaceutically acceptable salt thereof.

5. The hydrazone derivative as claimed in claim 1, wherein Ring A is aryl, or a pharmaceutically acceptable salt thereof.

6. The hydrazone derivative as claimed in claim 1, wherein Ring A is phenyl or pyridyl, or a pharmaceutically acceptable salt thereof.

7. The hydrazone derivative as claimed in claim 1, wherein $R^1$ is hydrogen atom or halogen atom, or a pharmaceutically acceptable salt thereof.

8. The hydrazone derivative as claimed in claim 1, wherein $R^1$ is hydrogen atom, or a pharmaceutically acceptable salt thereof.

9. The hydrazone derivative as claimed in claim 1, wherein $R^2$ is cycloalkylsulfonyl, substituted or unsubstituted alkylsulfonyl, substituted or unsubstituted alkylthio, nitro, substituted or unsubstituted amino, substituted or unsubstituted aminosulfonyl, substituted or unsubstituted heterocyclyl-thio, substituted or unsubstituted heterocyclyl-sulfonyl, substituted or unsubstituted heteroarylsulfonyl, substituted or unsubstituted alkylsulfinyl, substituted or unsubstituted heteroaryl, or substituted or unsubstituted heteroarylthio, or a pharmaceutically acceptable salt thereof.

10. The hydrazone derivative as claimed in claim 1, wherein $R^2$ is cycloalkylsulfonyl, substituted or unsubstituted alkylsulfonyl, substituted or unsubstituted aminosulfonyl, or substituted or unsubstituted heterocyclyl-sulfonyl, or a pharmaceutically acceptable salt thereof.

11. The hydrazone derivative as claimed in claim 1, wherein $R^2$ is cycloalkylsulfonyl, substituted or unsubstituted alkylsulfonyl, or substituted or unsubstituted aminosulfonyl, or a pharmaceutically acceptable salt thereof.

12. The hydrazone derivative as claimed in claim 1, wherein $R^2$ is cycloalkylsulfonyl, or substituted or unsubstituted alkylsulfonyl, or a pharmaceutically acceptable salt thereof.

13. The hydrazone derivative as claimed in claim 1, wherein the substituent of the "substituted aminosulfonyl" in $R^2$ is substituted or unsubstituted alkyl, cycloalkyl, alkoxy, or substituted or unsubstituted heterocycle, or a pharmaceutically acceptable salt thereof.

14. The hydrazone derivative as claimed in claim 1, wherein the substituent of the "substituted alkylsulfonyl" in $R^2$ is alkoxy, or a pharmaceutically acceptable salt thereof.

15. The hydrazone derivative as claimed in claim 1, wherein $R^3$ and $R^4$ combine each other together with the adjacent nitrogen atom to form substituted or unsubstituted heterocycle, or a pharmaceutically acceptable salt thereof.

16. The hydrazone derivative as claimed in claim 1, wherein the heterocycle in the "substituted or unsubstituted heterocycle which $R^3$ and $R^4$ combine each other together with the adjacent nitrogen atom to form" is pyrrolidine, piperidine, piperazine, morpholine, thiomorpholine, azetidine, homopiperazine, homomorpholine or homothiomorpholine, or a pharmaceutically acceptable salt thereof.

17. The hydrazone derivative as claimed in claim 1, wherein the substituent of substituted heterocycle in the "substituted or unsubstituted heterocycle which $R^3$ and $R^4$ combine each other together with the adjacent nitrogen atom to form" is alkyl, alkoxy, hydroxy or oxo, or a pharmaceutically acceptable salt thereof.

18. The hydrazone derivative as claimed in claim 1, wherein $R^5$ is hydrogen atom, formyl, halogen atom, oxo, substituted or unsubstituted alkoxy, substituted or unsubstituted aminosulfonyl, substituted or unsubstituted alkylthio, cyano, substituted or unsubstituted heterocyclyl-sulfonyl, nitro, substituted or unsubstituted cycloalkyl, alkoxycarbonyl, alkenyl, substituted or unsubstituted carbamoyl, substituted or unsubstituted heteroarylthio, substituted or unsubstituted amino, substituted or unsubstituted heteroaryl, substituted or unsubstituted alkynyl, substituted or unsubstituted heterocyclyl-oxy, alkanoyl, or substituted or unsubstituted alkyl, or a pharmaceutically acceptable salt thereof.

19. The hydrazone derivative as claimed in claim 1, wherein $R^5$ is hydrogen atom, halogen atom, substituted or unsubstituted alkoxy, substituted or unsubstituted alkylthio, cyano, substituted or unsubstituted cycloalkyl, substituted or unsubstituted carbamoyl, substituted or unsubstituted amino, substituted or unsubstituted heterocyclyl-oxy, alkanoyl, or substituted or unsubstituted alkyl, or a pharmaceutically acceptable salt thereof.

20. The hydrazone derivative as claimed in claim 1, wherein $R^5$ is halogen atom, substituted or unsubstituted alkoxy, substituted or unsubstituted alkylthio, substituted or unsubstituted amino, substituted or unsubstituted heterocyclyl-oxy, or substituted or unsubstituted alkyl, or a pharmaceutically acceptable salt thereof.

21. The hydrazone derivative as claimed in claim 1, wherein $R^5$ is substituted or unsubstituted alkoxy, substituted or unsubstituted amino, substituted or unsubstituted heterocyclyl-oxy, or substituted or unsubstituted alkyl, or a pharmaceutically acceptable salt thereof.

22. The hydrazone derivative as claimed in claim 1, wherein $R^5$ is substituted or unsubstituted alkyl, or a pharmaceutically acceptable salt thereof.

23. The hydrazone derivative as claimed in claim 1, wherein the substituent of the "substituted alkyl" in $R^5$ is substituted or unsubstituted heterocycle, substituted or unsubstituted amino, substituted or unsubstituted alkoxy, substituted or unsubstituted carbamoyl, hydroxy, trialkylsilyloxy, alkylthio, alkylsulfonyl, substituted or unsubstituted heterocyclyl-oxy, heteroaryl, substituted or unsubstituted hydroxyimino, halogen atom, carboxy, alkoxycarbonyl, or alkanoyloxy, or a pharmaceutically acceptable salt thereof.

24. The hydrazone derivative as claimed in claim 1, wherein $R^5$ is substituted or unsubstituted alkoxy, or a pharmaceutically acceptable salt thereof.

25. The hydrazone derivative as claimed in claim 1, wherein the substituent of the "substituted alkoxy" in $R^5$ is amino optionally substituted by 1 or 2 group(s) selected from alkyl or alkoxycarbonyl; alkoxycarbonyl; carbamoyl optionally substituted by mono- or di-alkyl; carboxyl; hydroxy; heterocycle optionally substituted by oxo; trialkylsilyloxy; or alkoxy; or a pharmaceutically acceptable salt thereof.

26. The hydrazone derivative as claimed in claim 1, wherein $R^6$ is hydrogen atom, or substituted or unsubstituted alkyl, or a pharmaceutically acceptable salt thereof.

27. The hydrazone derivative as claimed in claim 1, wherein $R^6$ is hydrogen atom, or a pharmaceutically acceptable salt thereof.

28. A pharmaceutical composition comprising:
the hydrazone derivative as claimed in claim 1, or a pharmaceutically acceptable salt thereof; and
a pharmaceutically acceptable carrier.

29. A method of treating diabetes, comprising:
administering to a patient in need of such treatment a pharmaceutically acceptable amount of a pharmaceutical composition comprising:
(i) a hydrazone derivative of the formula [I]:

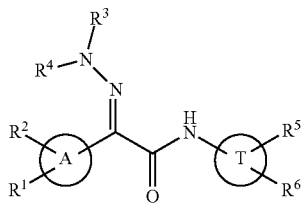

wherein Ring A is aryl or heteroaryl;

Ring T is a heteroaryl of

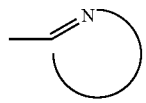

or a heterocycle of

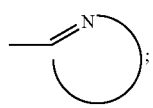;

$R^1$ is hydrogen atom, halogen atom, cycloalkylsulfonyl, alkylsulfonyl, alkylsulfinyl, alkylthio, substituted or unsubstituted tetrazolyl, —$COR^{10}$ or —$CR^{12}(OH)R^{10}$;

$R^2$ is hydrogen atom, halogen atom, cycloalkylsulfonyl, substituted or unsubstituted alkylsulfonyl, substituted or unsubstituted alkylthio, nitro, substituted or unsubstituted amino, substituted or unsubstituted aminosulfonyl, substituted or unsubstituted heterocyclyl-thio, substituted or unsubstituted heterocyclyl-sulfinyl, substituted or unsubstituted heterocyclyl-sulfonyl, substituted or unsubstituted heteroarylsulfonyl, alkenyloxy, substituted or unsubstituted alkoxy, substituted or unsubstituted alkylsulfinyl, substituted or unsubstituted heteroaryl, substituted or unsubstituted heteroarylthio, —$COR^{11}$ or —$CR^{13}(OH)R^{11}$;

$R^{10}$ is alkyl, cycloalkyl, heteroaryl or heterocycle;

$R^{11}$ is substituted or unsubstituted alkyl, substituted or unsubstituted cycloalkyl, substituted or unsubstituted heteroaryl or heterocycle;

$R^{12}$ is hydrogen atom or alkyl;

$R^{13}$ is hydrogen atom or alkyl;

$R^3$ and $R^4$ are independently hydrogen atom, substituted or unsubstituted alkyl or substituted or unsubstituted heteroaryl; or $R^3$ and $R^4$ combine each other together with the adjacent nitrogen atom to form substituted or unsubstituted heterocycle;

$R^5$ is hydrogen atom, formyl, halogen atom, oxo, substituted or unsubstituted alkoxy, substituted or unsubstituted aminosulfonyl, substituted or unsubstituted alkylthio, cyano, substituted or unsubstituted heterocyclyl-sulfonyl, nitro, substituted or unsubstituted cycloalkyl, alkoxycarbonyl, alkenyl, alkylsulfonyl, substituted or unsubstituted carbamoyl, substituted or unsubstituted heteroarylthio, substituted or unsubstituted amino, carboxy, substituted or unsubstituted heteroaryl, substituted or unsubstituted alkynyl, substituted or unsubstituted heterocyclyl-carbonyl, substituted or unsubstituted heterocyclyl-oxy, substituted or unsubstituted heterocycle, substituted or unsubstituted heterocyclyl-thio, substituted or unsubstituted cycloalkyloxy, alkanoyl, or substituted or unsubstituted alkyl;

$R^6$ is hydrogen atom, substituted or unsubstituted alkyl, halogen atom, or carboxy;

or a pharmaceutically acceptable salt thereof; and (ii) a pharmaceutically acceptable carrier.

30. A method of treating chronic complication associated with diabetes including retinopathy, nephropathy, neuropathy, ischemic heart disease or arteriosclerosis, comprising:
administering to a patient in need of such treatment a pharmaceutically acceptable amount of a pharmaceutical composition comprising:

(i) a hydrazone derivative of the formula [I]:

wherein Ring A is aryl or heteroaryl;
Ring T is a heteroaryl of or a heterocycle of $R^1$ is hydrogen atom, halogen atom, cycloalkylsulfonyl, alkylsulfonyl, alkylsulfinyl, alkylthio, substituted or unsubstituted tetrazolyl, —$COR^{10}$ or —$CR^{12}(OH)R^{10}$;
$R^2$ is hydrogen atom, halogen atom, cycloalkylsulfonyl, substituted or unsubstituted alkylsulfonyl, substituted or unsubstituted alkylthio, nitro, substituted or unsubstituted amino, substituted or unsubstituted aminosulfonyl, substituted or unsubstituted heterocyclyl-thio, substituted or unsubstituted heterocyclyl-sulfinyl, substituted or unsubstituted heterocyclyl-sulfonyl, substituted or unsubstituted heteroarylsulfonyl, alkenyloxy, substituted or unsubstituted alkoxy, substituted or unsubstituted alkylsulfinyl, substituted or unsubstituted heteroaryl, substituted or unsubstituted heteroarylthio, —$COR^{11}$ or —$CR^{13}(OH)R^{11}$;
$R^{10}$ is alkyl, cycloalkyl, heteroaryl or heterocycle;
$R^{11}$ is substituted or unsubstituted alkyl, substituted or unsubstituted cycloalkyl, substituted or unsubstituted heteroaryl or heterocycle;
$R^{12}$ is hydrogen atom or alkyl;
$R^{13}$ is hydrogen atom or alkyl;
$R^3$ and $R^4$ are independently hydrogen atom, substituted or unsubstituted alkyl or substituted or unsubstituted heteroaryl; or $R^3$ and $R^4$ combine each other together with the adjacent nitrogen atom to form substituted or unsubstituted heterocycle;
$R^5$ is hydrogen atom, formyl, halogen atom, oxo, substituted or unsubstituted alkoxy, substituted or unsubstituted aminosulfonyl, substituted or unsubstituted alkylthio, cyano, substituted or unsubstituted heterocyclyl-sulfonyl, nitro, substituted or unsubstituted cycloalkyl, alkoxycarbonyl, alkenyl, alkylsulfonyl, substituted or unsubstituted carbamoyl, substituted or unsubstituted heteroarylthio, substituted or unsubstituted amino, carboxy, substituted or unsubstituted heteroaryl, substituted or unsubstituted alkynyl, substituted or unsubstituted heterocyclyl-carbonyl, substituted or unsubstituted heterocyclyl-oxy, substituted or unsubstituted heterocycle, substituted or unsubstituted heterocyclyl-thio, substituted or unsubstituted cycloalkyloxy, alkanoyl, or substituted or unsubstituted alkyl;
$R^6$ is hydrogen atom, substituted or unsubstituted alkyl, halogen atom, or carboxy;
or a pharmaceutically acceptable salt thereof; and
(ii) a pharmaceutically acceptable earlier.

31. A method of treating obesity, comprising:
administering to a patient in need of such treatment a pharmaceutically acceptable amount of a pharmaceutical composition comprising:
(i) a hydrazone derivative of the formula [I]:

wherein Ring A is aryl or heteroaryl;
Ring T is a heteroaryl of or a heterocycle of $R^1$ is hydrogen atom, halogen atom, cycloalkylsulfonyl, alkylsulfonyl, alkylsulfinyl, alkylthio, substituted or unsubstituted tetrazolyl, —$COR^{10}$ or —$CR^{12}(OH)R^{10}$;
$R^2$ is hydrogen atom, halogen atom, cycloalkylsulfonyl, substituted or unsubstituted alkylsulfonyl, substituted or unsubstituted alkylthio, nitro, substituted or unsubstituted amino, substituted or unsubstituted aminosulfonyl, substituted or unsubstituted, heterocyclyl-thio, substituted or unsubstituted heterocyclyl-sulfinyl, substituted or unsubstituted heterocyclyl-sulfonyl, substituted or unsubstituted heteroarylsulfonyl, alkenyloxy, substituted or unsubstituted alkoxy, substituted or unsubstituted alkylsulfinyl, substituted or unsubstituted heteroaryl, substituted or unsubstituted heteroarylthio, —$COR^{11}$ or —$CR^{13}(OH)R^{11}$;
$R^{10}$ is alkyl, cycloalkyl, heteroaryl or heterocycle;
$R^{11}$ is substituted or unsubstituted alkyl, substituted or unsubstituted cycloalkyl, substituted or unsubstituted heteroaryl or heterocycle;
$R^{12}$ is hydrogen atom or alkyl;
$R^{13}$ is hydrogen atom or alkyl;
$R^3$ and $R^4$ are independently hydrogen atom, substituted or unsubstituted alkyl or substituted or unsubstituted heteroaryl; or $R^3$ and $R^4$ combine each other together with the adjacent nitrogen atom to form substituted or unsubstituted heterocycle;

$R^5$ is hydrogen atom, formyl, halogen atom, oxo, substituted or unsubstituted alkoxy, substituted or unsubstituted aminosulfonyl, substituted or unsubstituted alkylthio, cyano, substituted or unsubstituted heterocyclylsulfonyl, nitro, substituted or unsubstituted cycloalkyl, alkoxycarbonyl, alkenyl, alkylsulfonyl, substituted or unsubstituted carbamoyl, substituted or unsubstituted heteroarylthio, substituted or unsubstituted amino, carboxy, substituted or unsubstituted heteroaryl, substituted or unsubstituted alkynyl, substituted or unsubstituted heterocyclyl-carbonyl, substituted or unsubstituted heterocyclyl-oxy, substituted or unsubstituted heterocycle, substituted or unsubstituted heterocyclyl-thio, substituted or unsubstituted cycloalkyloxy, alkanoyl, or substituted or unsubstituted alkyl;

$R^6$ is hydrogen atom, substituted or unsubstituted alkyl, halogen atom, or carboxy;

or a pharmaceutically acceptable salt thereof; and (ii) a pharmaceutically acceptable carrier.

* * * * *